US012509441B2

(12) United States Patent
Li et al.

(10) Patent No.: US 12,509,441 B2
(45) Date of Patent: Dec. 30, 2025

(54) COMPOUNDS USED AS KINASE INHIBITORS AND APPLICATION THEREOF

(71) Applicants: TYK MEDICINES (ZHENGZHOU), INC., Henan (CN); TYK MEDICINES, INC., Zhejiang (CN)

(72) Inventors: Jun Li, Henan (CN); Chengshan Niu, Henan (CN); Apeng Liang, Henan (CN); Zhongwei Guo, Henan (CN); Yusheng Wu, Henan (CN)

(73) Assignees: TYK MEDICINES (ZHENGZHOU), INC., Henan (CN); TYK MEDICINES, INC., Zhejiang (CN)

( * ) Notice: Subject to any disclaimer, the term of this patent is extended or adjusted under 35 U.S.C. 154(b) by 663 days.

(21) Appl. No.: 17/911,138

(22) PCT Filed: Mar. 15, 2021

(86) PCT No.: PCT/CN2021/080892
§ 371 (c)(1),
(2) Date: Sep. 13, 2022

(87) PCT Pub. No.: WO2021/180238
PCT Pub. Date: Sep. 16, 2021

(65) Prior Publication Data

US 2023/0150975 A1 May 18, 2023

(30) Foreign Application Priority Data

Mar. 13, 2020 (CN) ......................... 202010175791.7

(51) Int. Cl.

| | |
|---|---|
| ***C07D 401/14*** | (2006.01) |
| ***C07D 403/04*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 491/048*** | (2006.01) |

(52) U.S. Cl.
CPC ......... *C07D 401/14* (2013.01); *C07D 403/04* (2013.01); *C07D 413/14* (2013.01); *C07D 417/14* (2013.01); *C07D 471/04* (2013.01); *C07D 487/04* (2013.01); *C07D 491/048* (2013.01)

(58) Field of Classification Search
CPC .. C07D 401/14; C07D 403/04; C07D 413/14; C07D 417/14; C07D 471/04; C07D 487/04; C07D 491/048; C07D 403/14; A61P 35/00
See application file for complete search history.

(56) References Cited

FOREIGN PATENT DOCUMENTS

| | | | |
|---|---|---|---|
| CN | 104761544 | 7/2015 | |
| CN | 105085489 | 11/2015 | |
| CN | 106559991 | 4/2017 | |
| CN | 108017633 | 5/2018 | |
| CN | 108069939 | 5/2018 | |
| CN | 108191861 | 6/2018 | |
| CN | 108503627 | 9/2018 | |
| CN | 106559991 B * | 9/2019 | ........... A61K 31/437 |
| CN | 110790749 | 2/2020 | |
| CN | 112292378 | 1/2021 | |
| CN | 114174269 | 3/2022 | |
| EP | 3205650 | 8/2017 | |
| EP | 3409669 | 12/2018 | |
| WO | 2016015453 | 2/2016 | |
| WO | 2020233669 | 11/2020 | |
| WO | 2021018017 | 2/2021 | |

OTHER PUBLICATIONS

"International Search Report (Form PCT/ISA/210) of PCT/CN2021/080892," mailed on Jun. 17, 2021, with English translation thereof, pp. 1-8.
"Search Report of Taiwan Counterpart Application", issued on Apr. 20, 2022, pp. 1.
"Partial Supplementary Search Report of Europe Counterpart Application", issued on Aug. 21, 2023, p. 1-p. 15.
"Search Report of China Counterpart Application", issued on Feb. 22, 2023, p. 1-p. 3.

* cited by examiner

*Primary Examiner* — Joseph K Mckane
*Assistant Examiner* — Meghan C Heasley
(74) *Attorney, Agent, or Firm* — JCIPRNET

(57) ABSTRACT

A kinase inhibitor compound of formula I or a pharmaceutically acceptable salt, solvate, or prodrug thereof. The compound has good inhibitory activity on EGFR and Her2 exon 20 insertion mutation, EGFR exon 19 deletion and L858R point mutation of exon 21.

Formula I

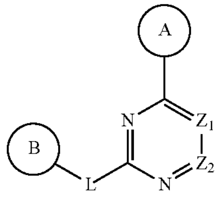

2 Claims, No Drawings

COMPOUNDS USED AS KINASE INHIBITORS AND APPLICATION THEREOF

CROSS-REFERENCE TO RELATED APPLICATION

This is a 371 application of the International PCT application serial no. PCT/CN2021/080892, filed on Mar. 15, 2021, which claims the priority benefits of China Application No. 202010175791.7, filed on Mar. 13, 2020.

TECHNICAL FIELD

The disclosure relates to a class of compounds used as kinase inhibitors and an application thereof, which belongs to the technical field of drugs.

DESCRIPTION OF RELATED ART

The epidermal growth factor receptor belongs to the receptor tyrosine kinase (RTK) family, which includes EGFR/ERBB1, HER2/ERBB2/NEU, HER3/ERBB3, and HER4/ERBB4. The epidermal growth factor receptor activates the tyrosine kinase activity thereof through homodimerization or heterodimerization, which in turn phosphorylates the substrate thereof, thereby activating multiple downstream pathways associated therewith in cells, such as the PI3K-AKT-mTOR pathway involved in cell survival and the RAS-RAF-MEK-ERK pathway involved in cell proliferation. Mutation or amplification of the epidermal growth factor receptor may lead to the activation of the epidermal growth factor receptor kinase, thereby leading to the occurrence of various human diseases, such as malignant tumors. For example, among patients with non-small cell lung cancer, more than 10% of patients in the United States have EGFR mutations, while the proportion of patients with the EGFR mutations in Asian patients can reach nearly 50%. Meanwhile, among the patients with non-small cell lung cancer, the incidence of Her2 mutation is about 2-4%.

The EGFR mutations mainly include deletion, insertion, and point mutation, among which exon 19 deletion and L858R point mutation of exon 21 account for nearly 90% of the EGFR mutations. For tumor patients with the EGFR mutations, currently marketed EGFR-TKIs include the first-generation Iressa, Tarceva, and Conmana, the second-generation afatinib and dacomitinib, and the third-generation osimertinib. The other 10% of the EGFR mutations mainly involve EGFR exon 18 and 20, and EGFR exon 20 insertion mutation accounts for about 9% of all the EGFR mutations. Among tumor patients with Her2 mutations, the most common Her2 mutation is Her2 exon 20 insertion mutation. For EGFR and Her2 exon 20 insertion mutations, there are currently no drugs on the market.

Recently, TAK-788 has been reported to have some activity on clinical EGFR exon 20 insertion mutation. Judging from the reported clinical trial results, the clinical response rate is only about 40%, and the curative effect is not satisfactory. Currently, the compound is still under clinical research.

SUMMARY

In order to meet the medication requirements of patients with EGFR and Her2 mutations, especially patients with EGFR and Her2 exon 20 insertion mutations, the disclosure has developed a series of compounds with excellent inhibitory activity on EGFR and Her2 exon 20 insertion mutations, EGFR exon 19 deletion, and L858R point mutation of exon 21, which have great potential to be developed into drugs for treating related diseases.

A first objective of the disclosure is to provide a class of compounds used as kinase inhibitors, which have good inhibitory activity on EGFR, Her2 exon 20 insertion mutation, EGFR exon 19 deletion, and L858R point mutation of exon 21.

A second objective of the disclosure is to provide an application of the compounds in the preparation of drugs for treating related diseases caused by EGFR mutations and/or Her2 mutation.

In order to solve the above issues, the technical solution adopted by the compounds used as the kinase inhibitors of the disclosure is as follows.

A compound used as a kinase inhibitor is a compound represented by Formula I or a pharmaceutically acceptable salt, solvate, or prodrug thereof:

Formula I

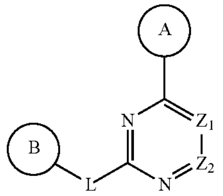

In Formula I, A is selected from:

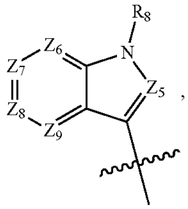 ,

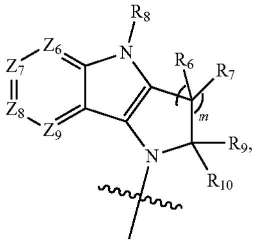

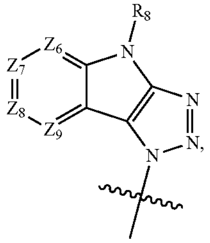

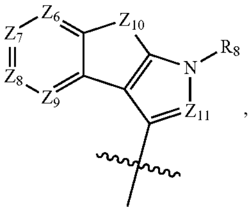 ,

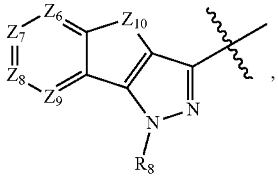 ,

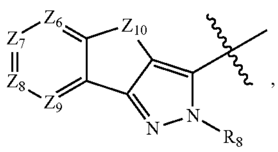 ,

-continued

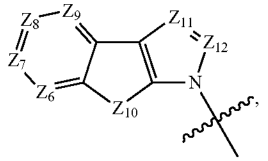, 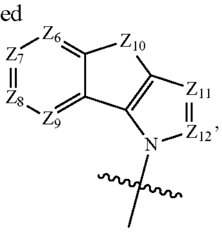,

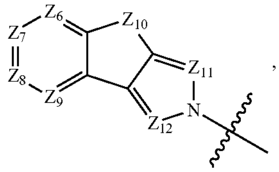, 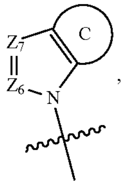, or

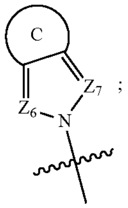;

wherein $Z_5$, $Z_6$, $Z_7$, $Z_8$, $Z_9$, $Z_{11}$, and $Z_{12}$ are each independently selected from N and $CR_4$; $Z_{10}$ is selected from

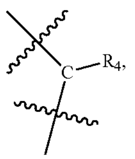 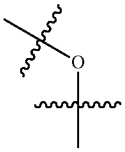, 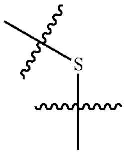,

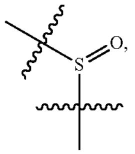 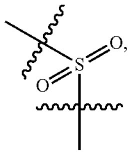 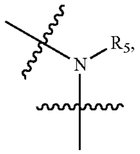

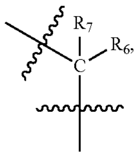 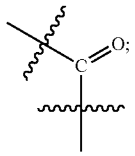

$R_8$ is selected from H, amino, ester, $C_{1-6}$ alkyl, deuterium of $C_{1-6}$ alkyl, $C_{1-6}$ alkoxy, deuterium of $C_{1-6}$ alkoxy, $C_{3-6}$ cycloalkyl, $C_{3-6}$ cycloalkoxy, $C_{6-10}$ aryl, 5-10 membered heteroaryl; or amino, ester, $C_{1-6}$ alkyl, $C_{1-6}$ alkoxy, $C_{3-6}$ cycloalkyl, $C_{3-6}$ cycloalkoxy, $C_{6-10}$ aryl, 5-10 membered heteroaryl substituted by 1 to 3 Rs; the 5-10 membered heteroaryl contains at least one heteroatom, the heteroatom is selected from N, O, S, or P; m is 0, 1, 2, or 3; C is selected as 4-7 membered ring;

$Z_1$ and $Z_2$ are each independently selected from N or $CR_4$;

L is selected from single bond,

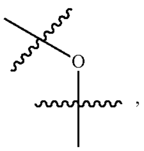, 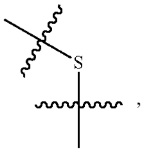,

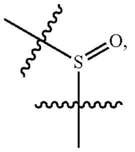 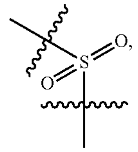

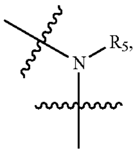 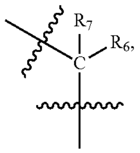

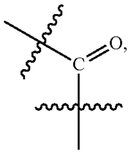 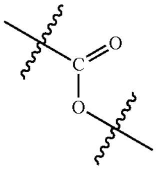, or

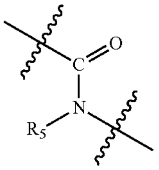;

B is selected from $C_{6-10}$ aryl, 5-10 membered heteroaryl, $C_{6-10}$ aryl substituted by 1 to 3 substituents, 5-10 membered heteroaryl substituted by 1 to 3 substituents; the substituents are each independently selected from H, halogen, cyano, amino, ester, urea, carbamate, amide, $C_{1-6}$ alkyl, $C_{1-6}$ alkoxy, $C_{3-6}$ cycloalkyl, $C_{3-6}$ cycloalkoxy, $C_{1-6}$ alkylamino, $C_{3-12}$ cycloalkylamino, $C_{1-6}$ haloalkyl, $C_{1-6}$ haloalkoxy, $C_{3-6}$ halocycloalkyl, $C_{3-6}$ halocycloalkoxy, $C_{1-6}$ haloalkylamino, $C_3$-12 halocycloalkylamino, $C_{6-10}$ aryl, 5-10 membered heteroaryl; or amino, ester, urea, carbamate, amide, $C_{1-6}$ alkyl, $C_{1-6}$ alkoxy, $C_{3-6}$ cycloalkyl, $C_{3-6}$ cycloalkoxy, $C_{1-6}$ alkylamino, $C_{3-12}$ cycloalkylamino, $C_{1-6}$ haloalkyl, $C_{1-6}$ haloalkoxy, $C_{3-6}$ halocycloalkyl, $C_{3-6}$ halocycloalkoxy, $C_{1-6}$ haloalkylamino, $C_{3-12}$ halocycloalkylamino, $C_{6-10}$ aryl, 5-10 membered heteroaryl substituted by 1 to 3 Rs;

The Rs are each independently selected from halogen, cyano, amino, hydroxyl, ester, urea, carbamate, amide, $C_{1-6}$ alkyl, $C_{1-6}$ alkoxy, $C_{3-6}$ cycloalkyl, $C_{3-6}$ cycloalkoxy, $C_{1-12}$ alkylamino, $C_{6-10}$ aryl, 5-10 membered heteroaryl,

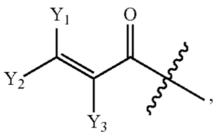, 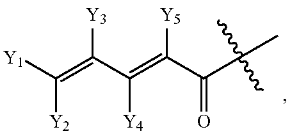,

-continued

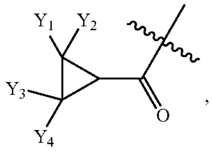
,
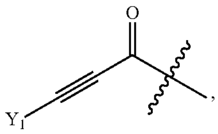
,

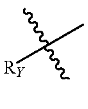
,
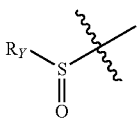
, or
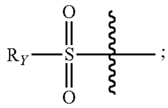
;

wherein $Y_1$, $Y_2$, $Y_3$, $Y_4$, $Y_5$ are each independently selected from hydrogen, halogen, $C_{1-12}$ alkyl, $C_{3-12}$ cycloalkyl, $C_{1-12}$ alkylamino, $R_Y$ is selected from $C_{1-12}$ alkyl, $C_{3-12}$ cycloalkyl, a group formed by substituting one or more carbon atoms in $C_{1-12}$ alkyl with one or more heteroatoms in N, O, S, a group formed by substituting one or more carbon atoms in $C_{3-12}$ cycloalkyl with one or more heteroatoms in N, O, S;

$R_4$, $R_6$, $R_7$, $R_9$, and $R_{10}$ are each independently selected from H, halogen, cyano, amino, ester, sulfone, urea, carbamate, amide, phosphoroxy, $C_{1-6}$ alkyl, deuterium of $C_{1-6}$ alkyl, $C_{1-6}$ alkoxy, $C_{3-6}$ cycloalkyl, $C_{3-6}$ cycloalkoxy, $C_{6-10}$ aryl, 5-10 membered heteroaryl, 5-10 membered aliphatic heterocyclyl, or amino, ester, sulfone, urea, carbamate, amide, $C_{1-6}$ alkyl, $C_{1-6}$ alkoxy, $C_{3-6}$ cycloalkyl, $C_{3-6}$ cycloalkoxy, $C_{6-10}$ aryl, 5-10 membered heteroaryl, 5-10 membered aliphatic heterocyclyl substituted by 1 to 3 of the Rs;

$R_5$ is selected from H, $C_{1-6}$ alkyl, $C_{1-6}$ alkoxy, $C_{3-6}$ cycloalkyl, $C_{3-6}$ cycloalkoxy, $C_{6-10}$ aryl, 5-10 membered heteroaryl;

wherein when $Z_1$ and $Z_2$ are both selected as CH, A is selected as

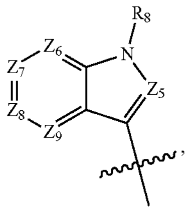
,

B is selected from $C_{6-10}$ aryl substituted by 1 to 3 substituents, and 5-10 membered heteroaryl substituted by 1 to 3 substituents, at least one of the 1 to 3 substituents in B is

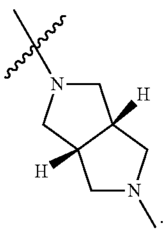 [SMILES: *N1C[C@@H]2CN(C)C[C@@H]2C1]
.

The compound used as the kinase inhibitor provided by the disclosure has good inhibitory activity on EGFR and Her2 exon 20 insertion mutations, EGFR exon 19 deletion, and L858R point mutation of exon 21, and has great potential to be developed into drugs for treating related diseases.

In order to further optimize the inhibitory effect on EGFR and Her2 exon 20 insertion mutations, preferably, the compound used as the kinase inhibitor is a compound represented by Formula II or a pharmaceutically acceptable salt, solvate, or prodrug thereof:

Formula II

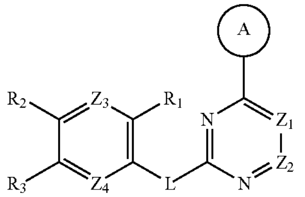

In the formula, $Z_3$ and $Z_4$ are each independently selected from N, $CR_4$;

$R_1$ and $R_2$ are each independently selected from H, halogen, cyano, amino, ester, urea, carbamate, amide, $C_{1-6}$ alkyl, $C_{1-6}$ alkoxy, $C_{3-6}$ cycloalkyl, $C_{3-6}$ cycloalkoxy, $C_{1-6}$ alkylamino, $C_{3-12}$ cycloalkylamino, $C_{1-6}$ haloalkyl, $C_{1-6}$ haloalkoxy, $C_{3-6}$ halocycloalkyl, $C_{3-6}$ halocycloalkoxy, $C_{1-6}$ haloalkylamino, $C_{3-12}$ halocycloalkylamino, $C_{6-10}$ aryl, 5-10 membered heteroaryl, or amino, ester, urea, carbamate, amide, $C_{1-6}$ alkyl, $C_{1-6}$ alkoxy, $C_{3-6}$ cycloalkyl, $C_{3-6}$ cycloalkoxy, $C_{1-6}$ alkylamino, $C_{3-12}$ cycloalkylamino, $C_{1-6}$ haloalkyl, $C_{1-6}$ haloalkoxy, $C_{3-6}$ halocycloalkyl, $C_{3-6}$ halocycloalkoxy, $C_{1-6}$ haloalkylamino, $C_{3-12}$ halocycloalkylamino, $C_{6-10}$ aryl, 5-10 membered heteroaryl substituted by 1 to 3 of the Rs;

$R_3$ is selected from

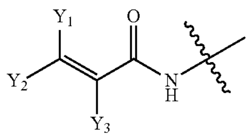
,
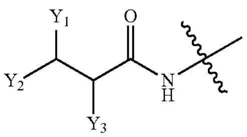
,

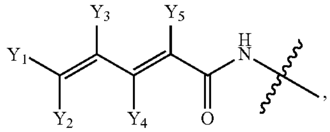
,

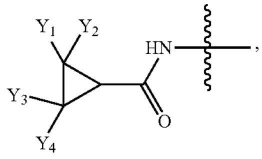
,

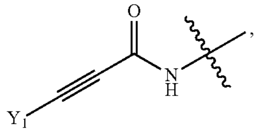
, or

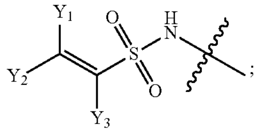
;

wherein $Y_1$, $Y_2$, $Y_3$, $Y_4$, $Y_5$ are each independently selected from hydrogen, halogen, $C_{1-12}$ alkyl, $C_{1-12}$ alkoxy, $C_{3-12}$ cycloalkyl, $C_{1-12}$ alkylamino, $C_{1-12}$ alkylamino substituted by the R.

In order to further optimize the inhibitory effect on EGFR and Her2 exon 20 insertion mutations, preferably, $Z_1$ is $CR_4$, $Z_2$ is CH, wherein $R_4$ is selected from H, 5-9 membered heteroaromatic ring containing one or more nitrogen atoms, 5-9 membered heteroaryl containing one or more nitrogen atoms with 1 to 3 substituents $R_{12}$, cyano,

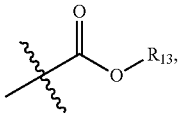
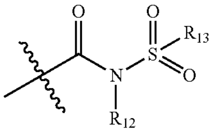
,
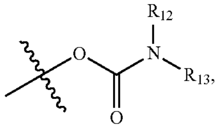
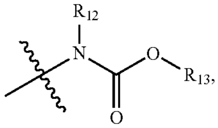
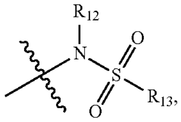
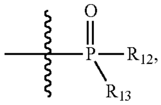
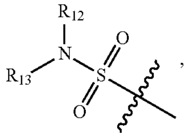
, or
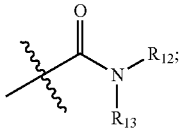

$R_{12}$ and $R_{13}$ are each independently selected from H, ester, acyl, $C_{1-6}$ alkyl, $C_{3-6}$ cycloalkyl, $C_{3-6}$ cycloalkoxy, $C_{6-10}$ aryl, 5-9 membered heteroaryl, or ester, acyl, $C_{1-6}$ alkyl, $C_{3-6}$ cycloalkyl, $C_{3-6}$ cycloalkoxy, $C_{6-10}$ aryl, 5-9 membered heteroaryl substituted by 1 to 3 of the Rs.

In order to further optimize the inhibitory effect on EGFR and Her2 exon 20 insertion mutations, preferably, a compound represented by Formula III is used:

Formula III

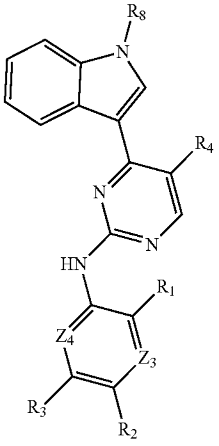

In Formula III, $R_8$ is hydrogen, $C_{3-6}$ cycloalkyl, $C_{1-3}$ alkyl, deuterium of $C_{1-3}$ alkyl, $C_{1-3}$ haloalkyl;

$R_4$ is selected from H,

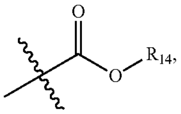
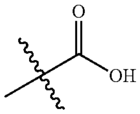
,
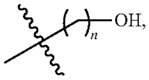
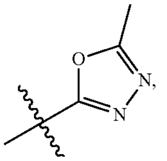
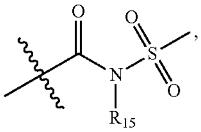
,
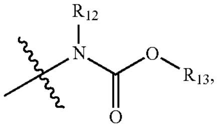
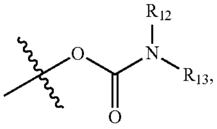
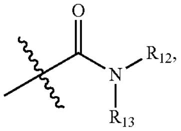
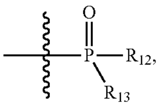
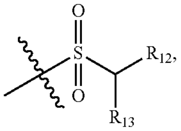
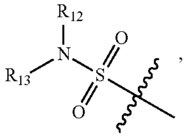
,
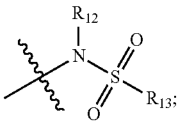

wherein $R_{14}$ is $C_{1-3}$ alkyl, n is an integer of 1 to 3, $R_{12}$, $R_{13}$, $R_{15}$ are each independently selected from H or $C_{1-3}$ alkyl;

$Z_3$ and $Z_4$ are each independently selected from CH or N;

$R_1$ is selected from hydrogen, $C_{1-3}$ alkoxy, $C_{1-3}$ haloalkoxy, deuterium of $C_{1-3}$ alkoxy, $C_{3-6}$ cycloalkyl;

$R_2$ is selected from

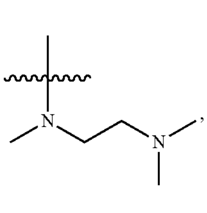
,
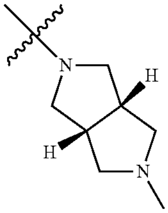
,
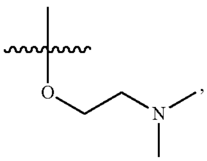
,
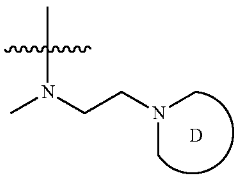
, where D ring is 4-6 membered cycloalkylamino;

$R_3$ is selected from

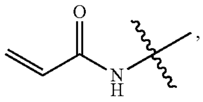
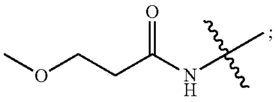

wherein when $R_4$ is selected from

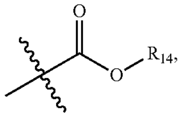
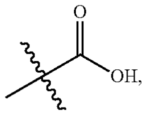
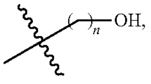
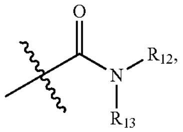
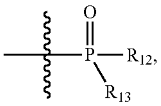
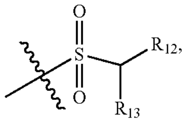
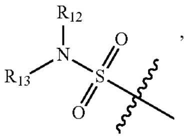
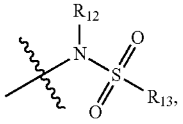

and $Z_3$ and $Z_4$ are selected as CH at the same time, $R_2$ is selected as

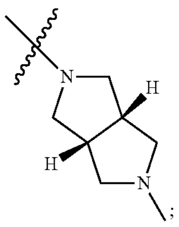 [SMILES: *N1C[C@@H]2CN(C)C[C@@H]2C1]

When $R_4$ is selected as H, $R_2$ is selected as

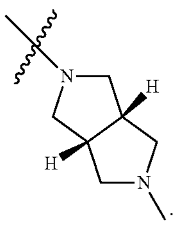 [SMILES: *N1C[C@@H]2CN(C)C[C@@H]2C1]

Preferably, a compound represented by Formula III' is used:

Formula III'

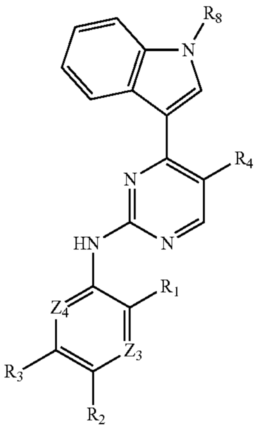

In Formula III', $R_8$ is hydrogen, $C_{3-6}$ cycloalkyl, $C_{1-3}$ alkyl, deuterium of $C_{1-3}$ alkyl, $C_{1-3}$ haloalkyl;

$R_4$ is selected from

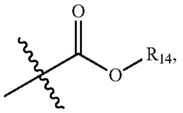
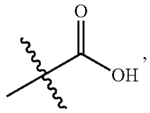
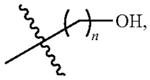
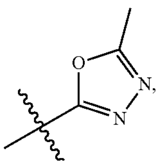
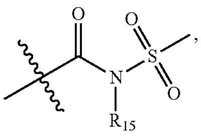
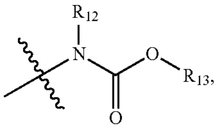
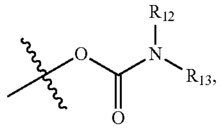
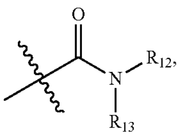
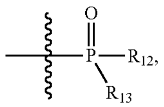
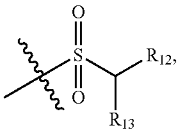
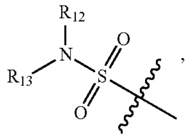
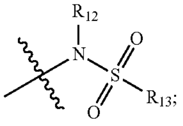

wherein $R_{14}$ is $C_{1-3}$ alkyl, n is an integer of 1 to 3, $R_{12}$, $R_{13}$, $R_{15}$ are each independently selected from H or $C_{1-3}$ alkyl;

$Z_3$ and $Z_4$ are each independently selected from CH or N, and at least one thereof is selected from N;

$R_1$ is selected from hydrogen, $C_{1-3}$ alkoxy, $C_{1-3}$ haloalkoxy, deuterium of $C_{1-3}$ alkoxy, $C_{3-6}$ cycloalkyl;

$R_2$ is selected from
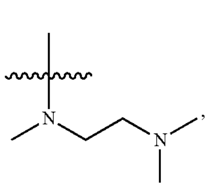
,
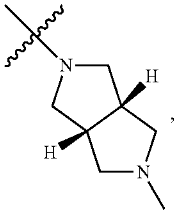
,
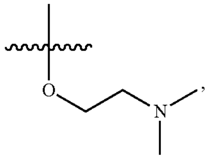
,
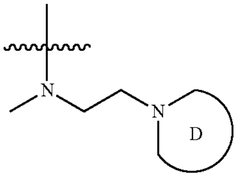
,
wherein D ring is 4-6 membered cycloalkylamino;
$R_3$ is selected as
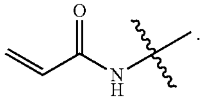 [SMILES: *NC(=O)C=C]
.
In order to further optimize the inhibitory effect on EGFR and Her2 exon 20 insertion mutations, preferably, a compound represented by Formula IV, Formula V, Formula VI, Formula VII, Formula VIII, Formula IX is used:
Formula IV
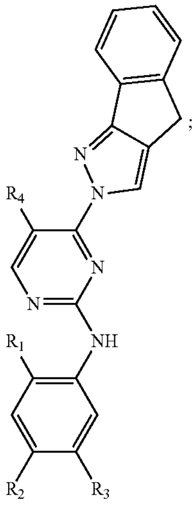
;
-continued
Formula V
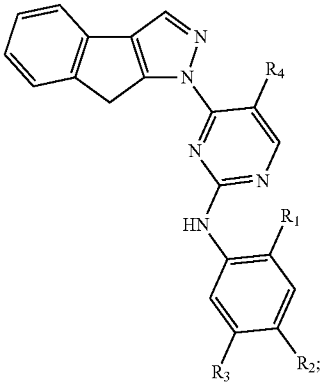
;
Formula VI
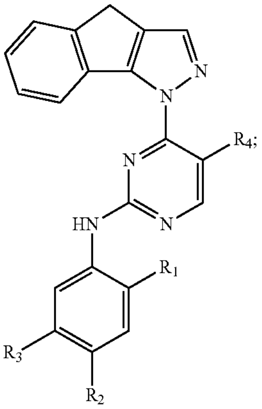
;
Formula VII
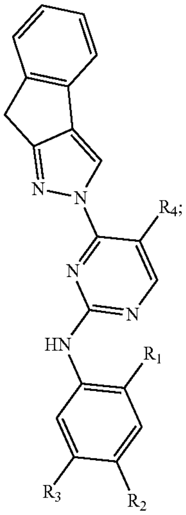
;

-continued

Formula VIII

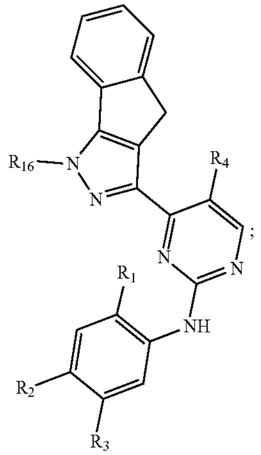

Formula IX

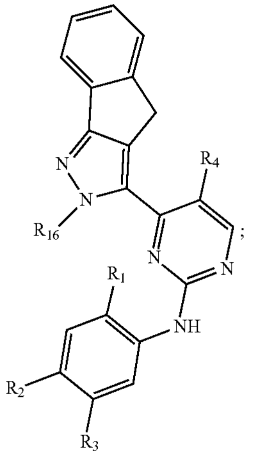

In Formula IV, Formula V, Formula VI, Formula VII, Formula VIII, and Formula IX, $R_1$ is selected from hydrogen, $C_{1-3}$ alkoxy, $C_{1-3}$ haloalkoxy, deuterium of $C_{1-3}$ alkoxy, $C_{3-6}$ cycloalkyl;

$R_2$ is selected from

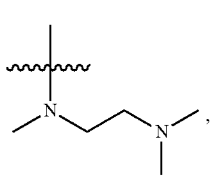

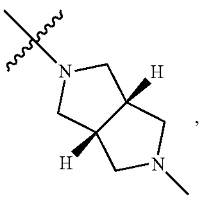

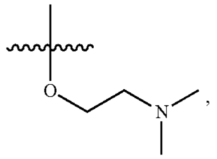

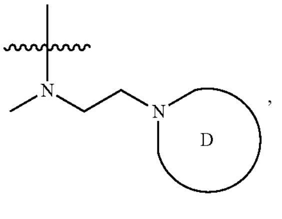

wherein D ring is 4-6 membered cycloalkylamino;

$R_3$ is selected from

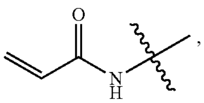

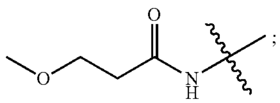

$R_4$ is selected from H,

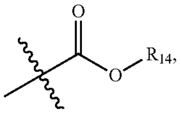

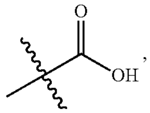

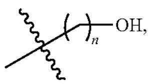

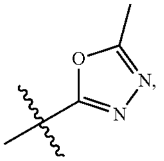

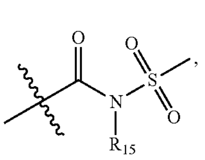

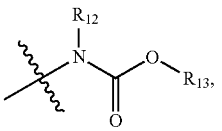

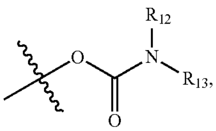

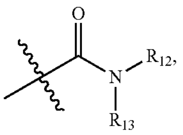

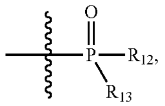

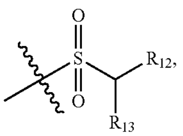

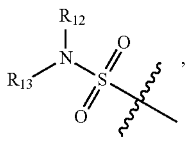

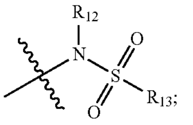

wherein $R_{14}$ is $C_{1-3}$ alkyl, n is an integer of 1 to 3, $R_{12}$, $R_{13}$, $R_{15}$ are each independently selected from H or $C_{1-3}$ alkyl;

$R_{16}$ is selected from H or $C_{1-3}$ alkyl.

In order to further optimize the inhibitory effect on EGFR and Her2 exon 20 insertion mutations, preferably, a structural formula of the compound used as the kinase inhibitor is selected from the following structures:

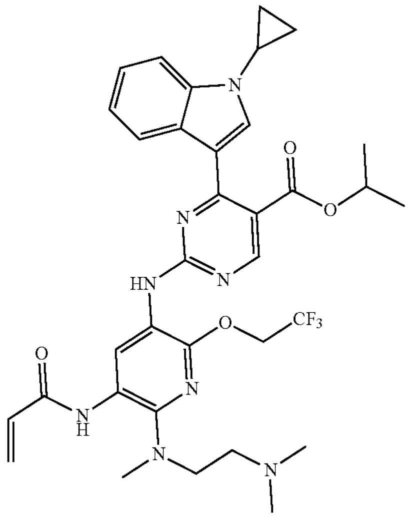
,
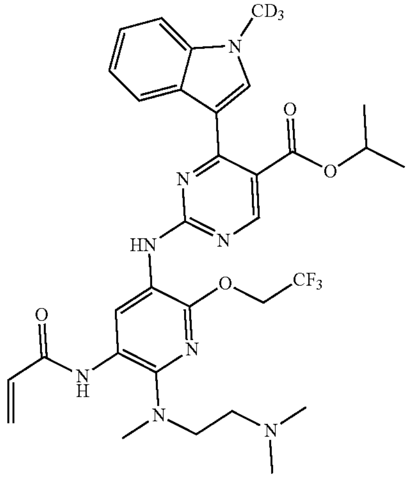
,
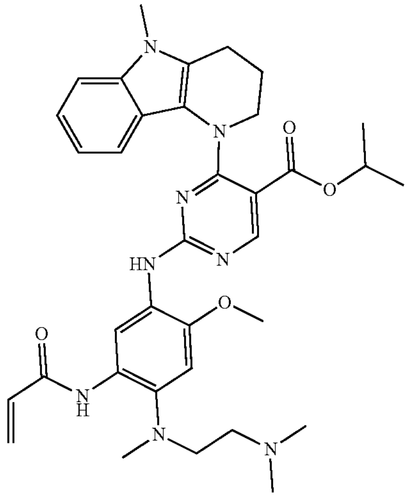
,
-continued
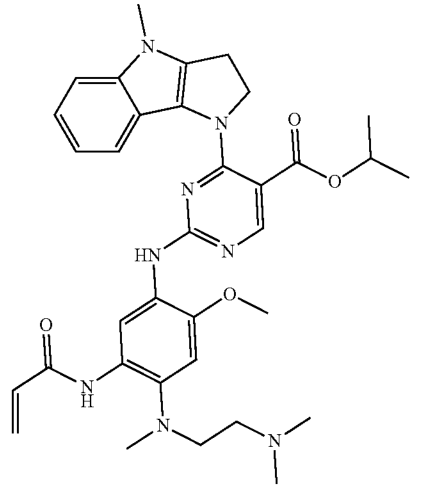
,
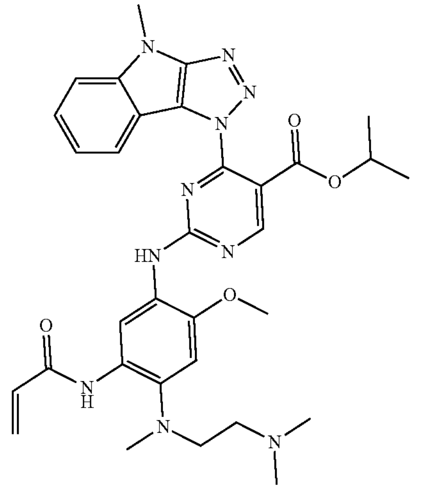
,
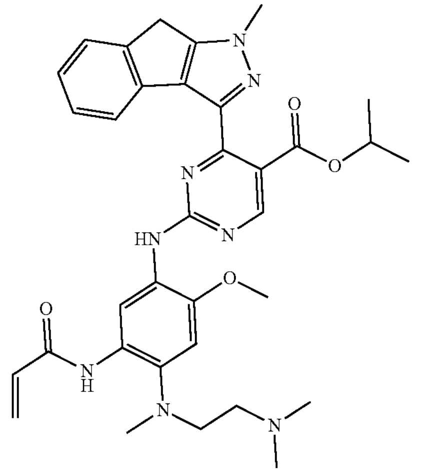
, -continued
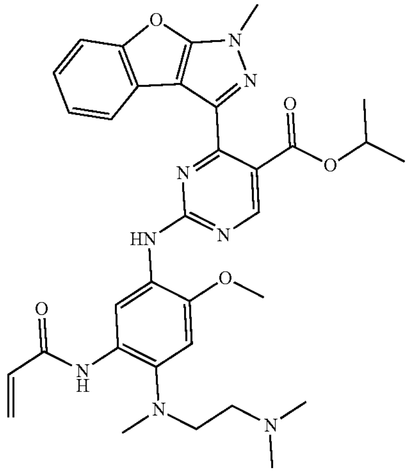
,
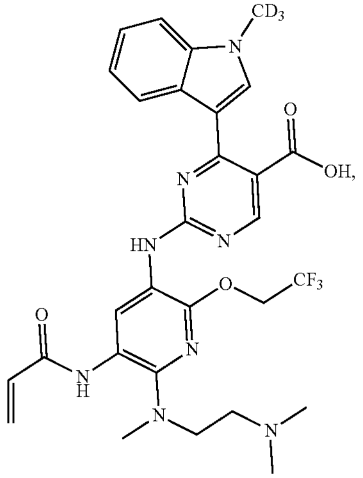
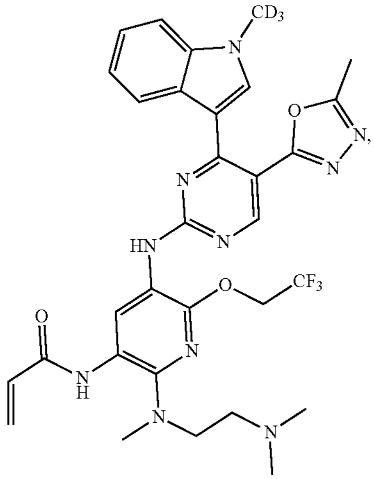
-continued
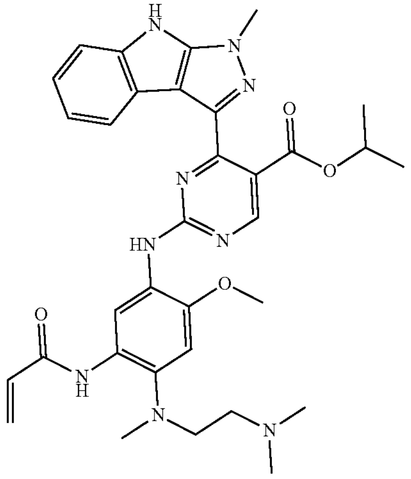
,
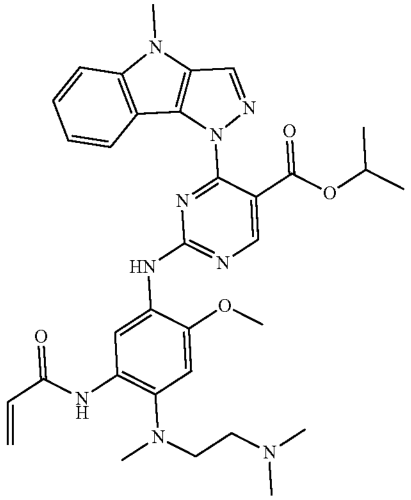
,
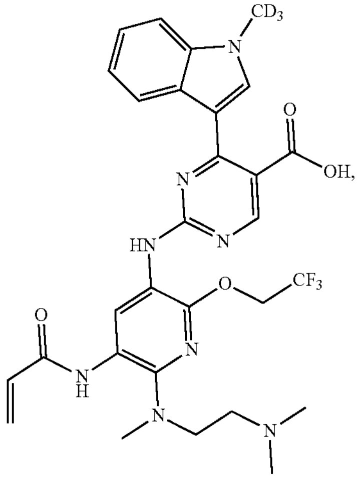

-continued
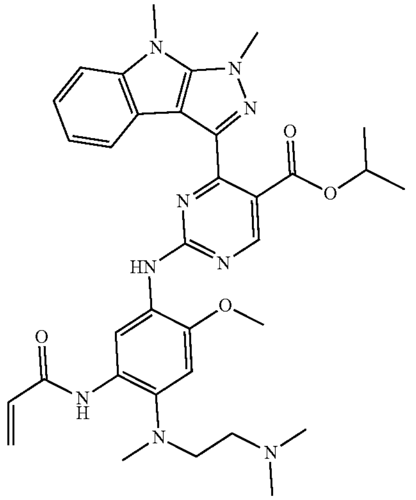
,
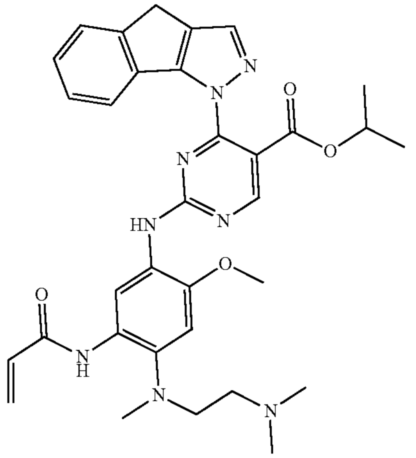
,
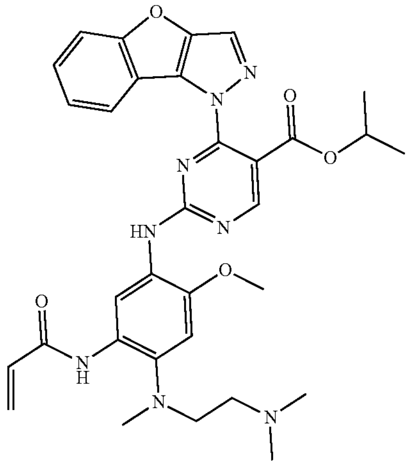
,
-continued
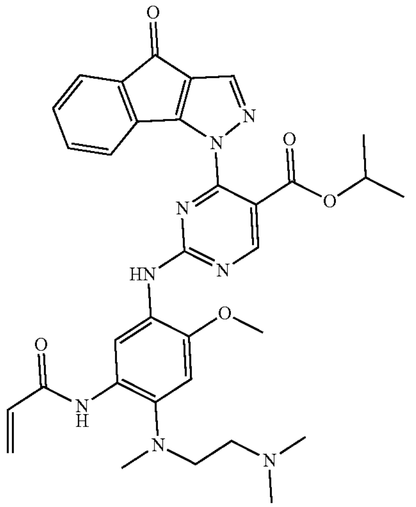
,
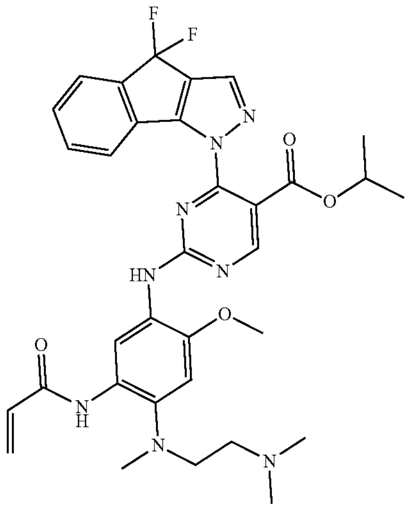
,
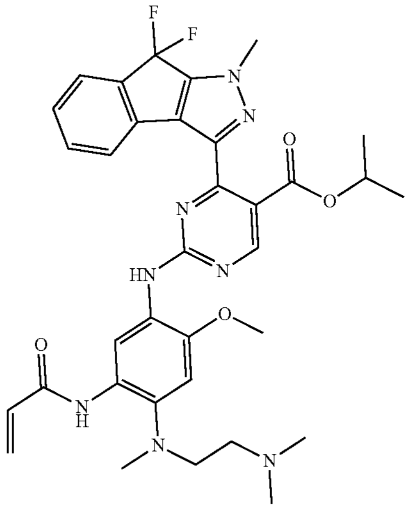
, -continued
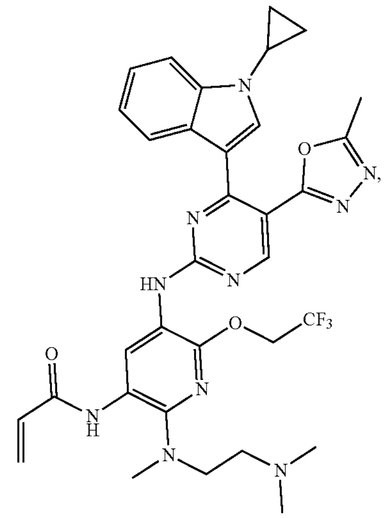
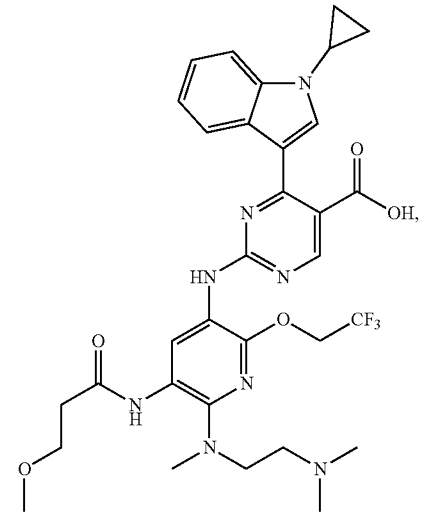
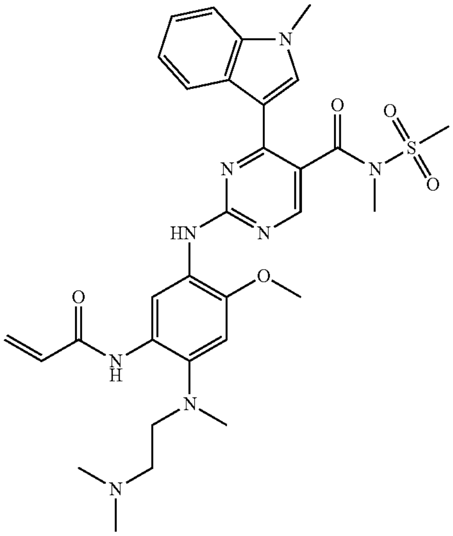
,
-continued
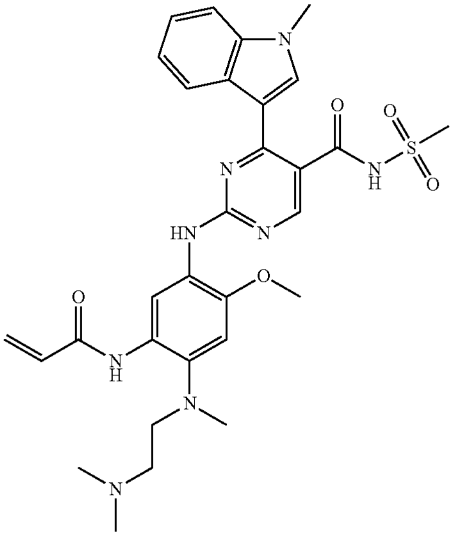
,
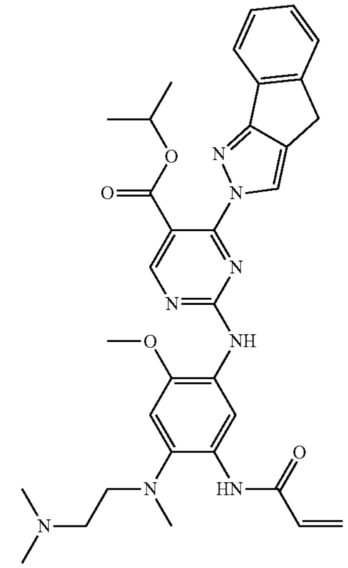
,
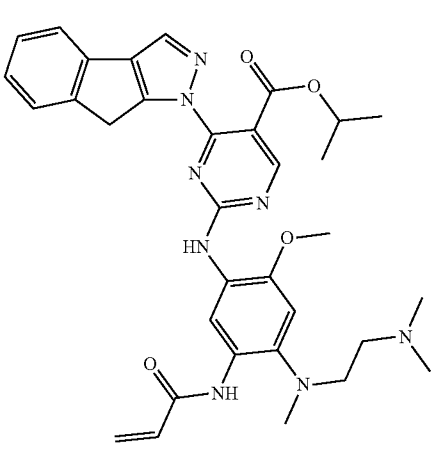
, -continued
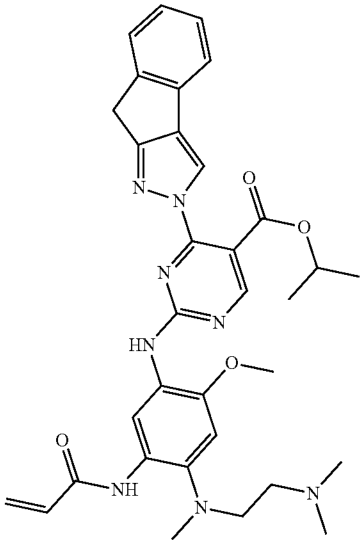
,
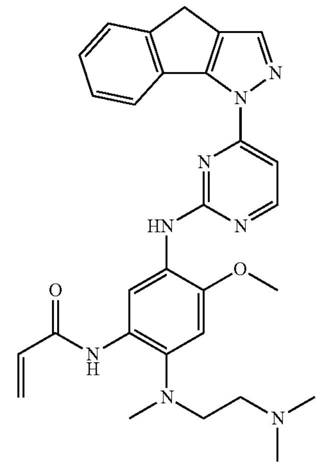
,
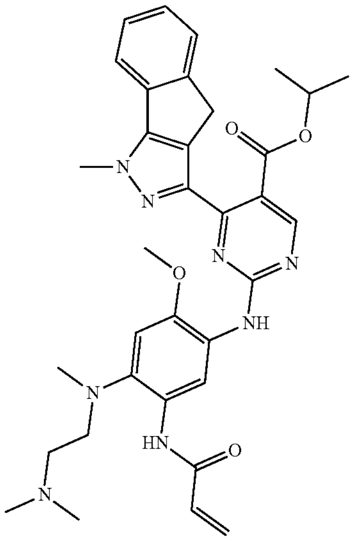
,
-continued
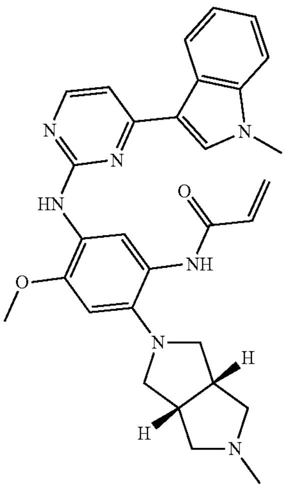
,
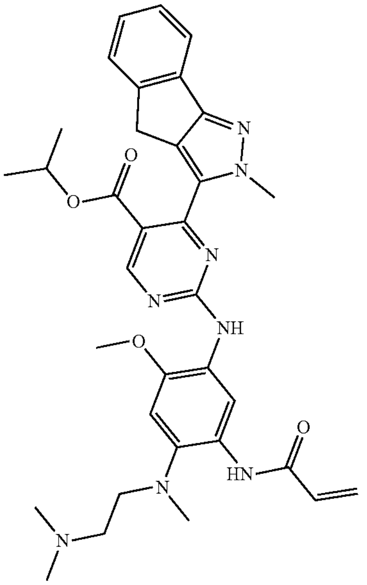
,
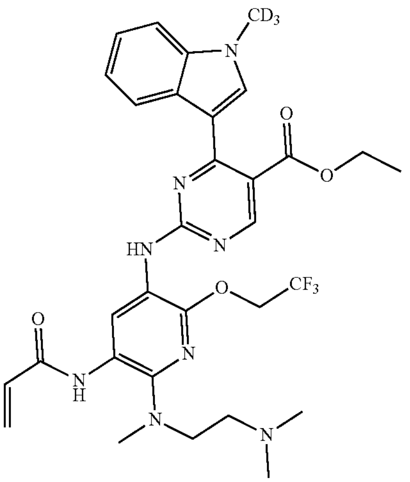
, -continued
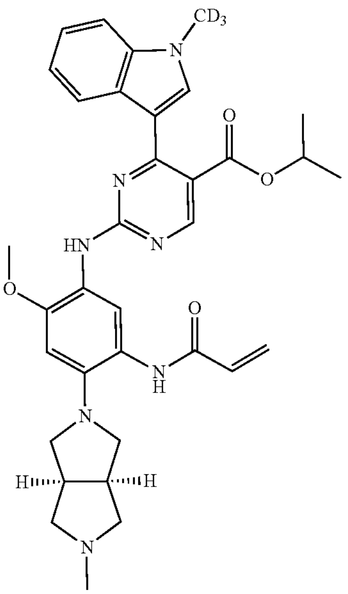
,
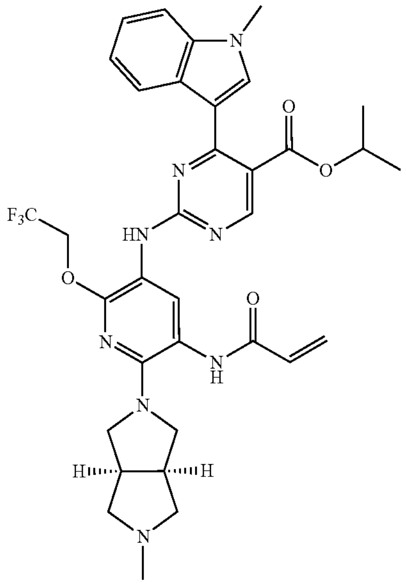
,
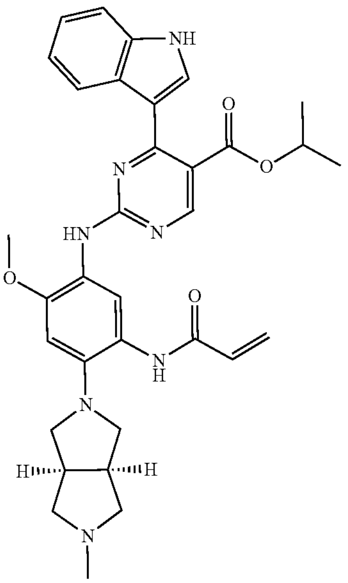
,
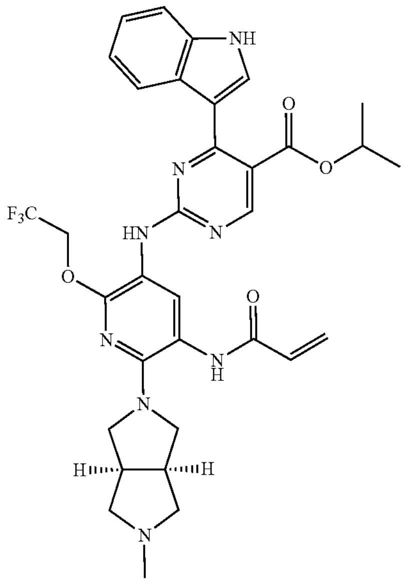
, -continued
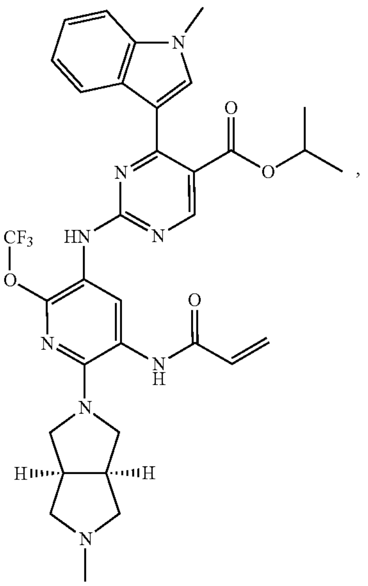
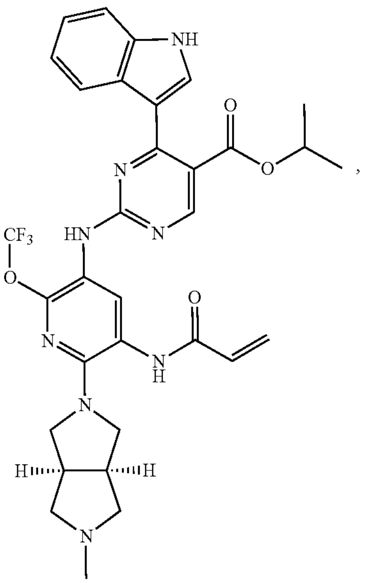
-continued
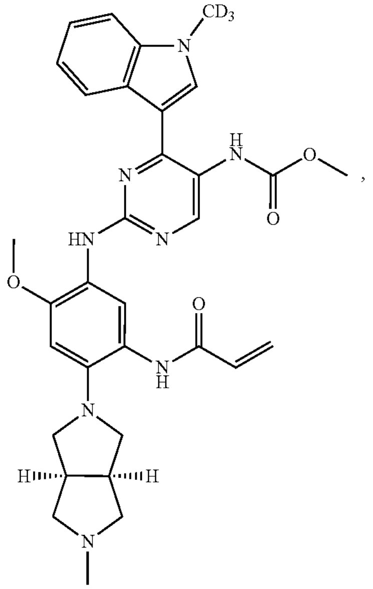
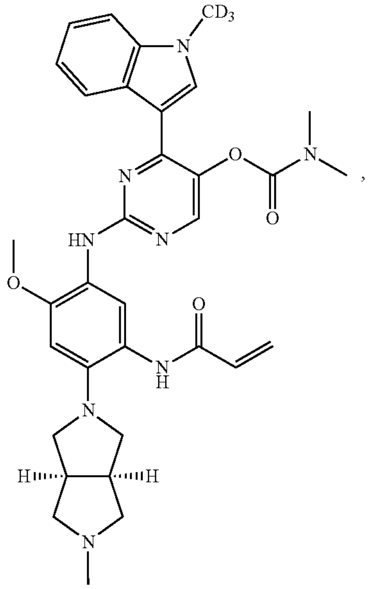

-continued
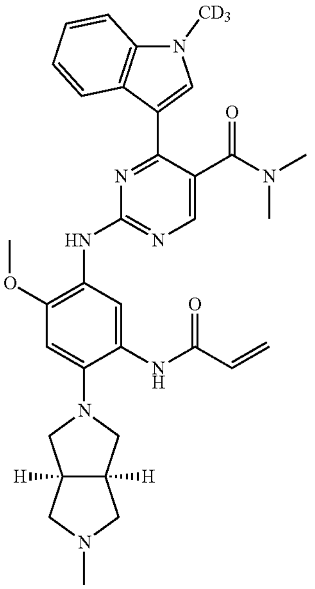
,
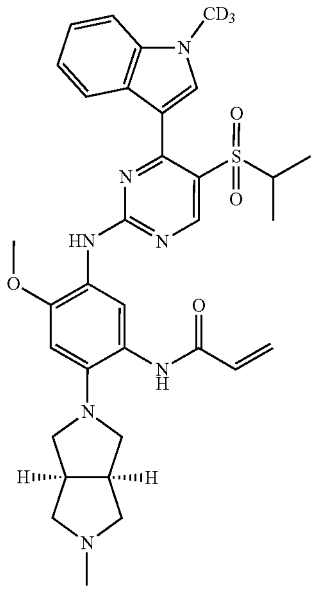
,
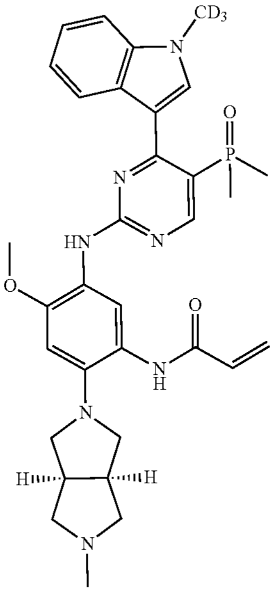
,
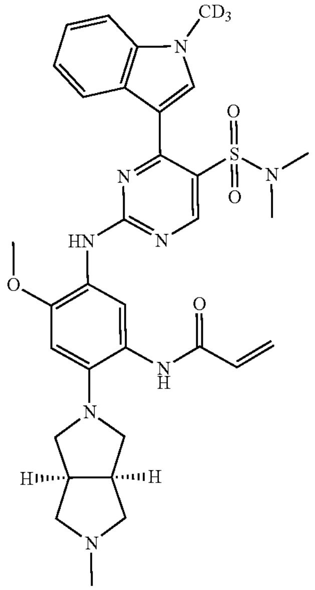
,

-continued

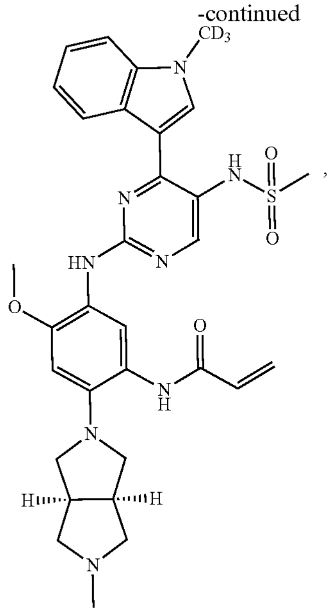,

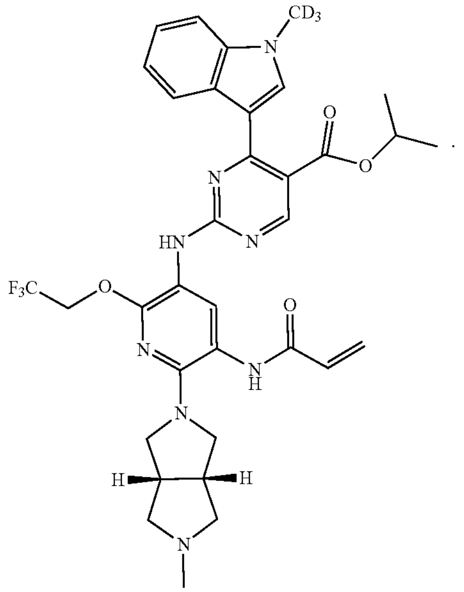 [SMILES: [2H]C([2H])([2H])n1cc(-c2nc(Nc3cc(NC(=O)C=C)c(N4C[C@H]5CN(C)C[C@H]5C4)nc3OCC(F)(F)F)ncc2C(=O)OC(C)C)c2ccccc21].

In addition to EGFR exon 20 insertion mutation, the compound of the following structure also has good inhibitory effect on exon 19 deletion and L858R point mutation of exon 21.

Preferably, the compound has a structure represented by Formula X:

Formula X

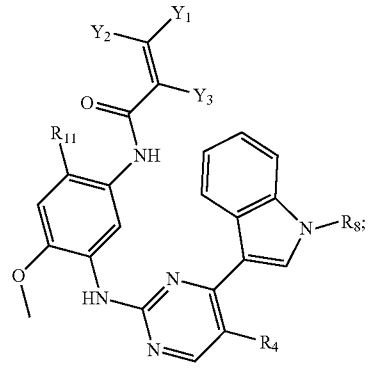

In Formula X, $R_8$ is selected from H, $C_{1-4}$ alkyl, deuterium of $C_{1-4}$ alkyl, $C_{1-4}$ haloalkyl;

$Y_1$, $Y_2$, $Y_3$ are each independently selected from H, D, halogen, $C_{1-4}$ haloalkyl, deuterium of $C_{1-4}$ alkyl, $-CH_2NR_{111}R_{112}$, or

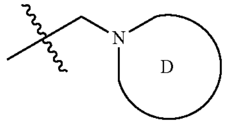, wherein D ring is 4-6 membered cycloalkylamino or 4-6 membered heterocycloalkylamino, the heterocycloalkylamino is that 1 to 3 ring carbon atoms in cycloalkylamino are substituted by heteroatoms, heteroatoms are selected from O, S, or N;

$R_4$ is selected from

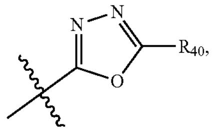

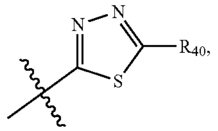

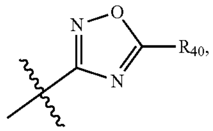

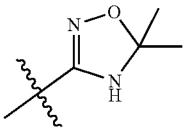,

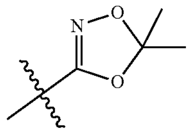,

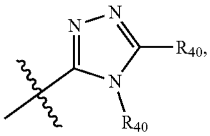

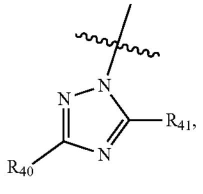

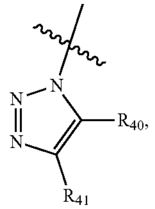

-continued

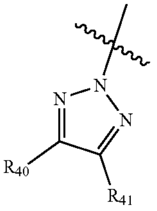,

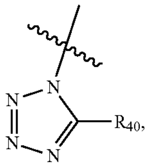

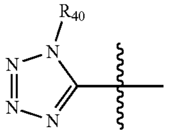;

wherein $R_{40}$ is selected from H, $C_{1-4}$ alkyl, deuterium of $C_{1-4}$ alkyl, or $C_{1-4}$ haloalkyl;

$R_{11}$ is selected from

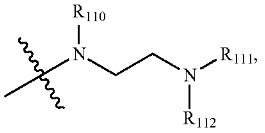

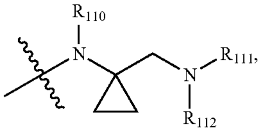

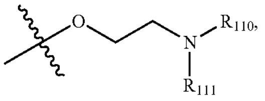

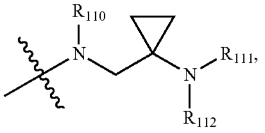

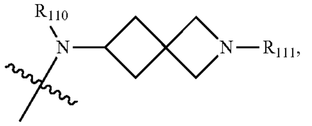

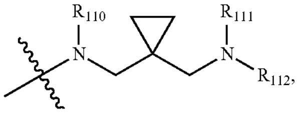

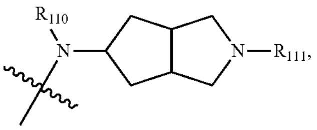

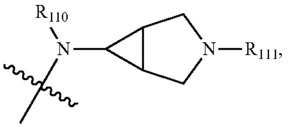

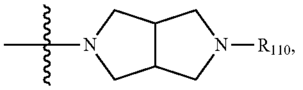

-continued

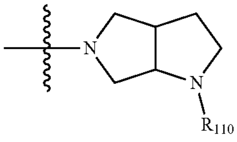;

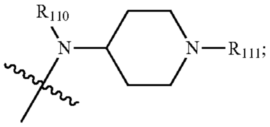

wherein $R_{110}$, $R_{111}$, $R_{112}$ are each independently selected from H, $C_{1-4}$ alkyl, deuterium of $C_{1-4}$ alkyl, or haloalkyl;

wherein when $R_{11}$ is selected as

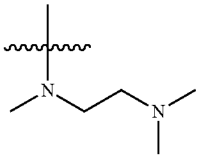, $Y_1$, $Y_2$, $Y_3$ are all H, $R_8$ is methyl, $R_4$ is

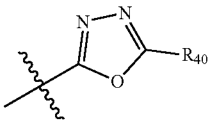

or

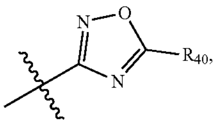

$R_{40}$ is selected from H, $C_{2-4}$ alkyl, deuterium of $C_{1-4}$ alkyl, or $C_{1-4}$ haloalkyl.

More preferably, a compound represented by Formula XI, Formula XII is used:

Formula XI

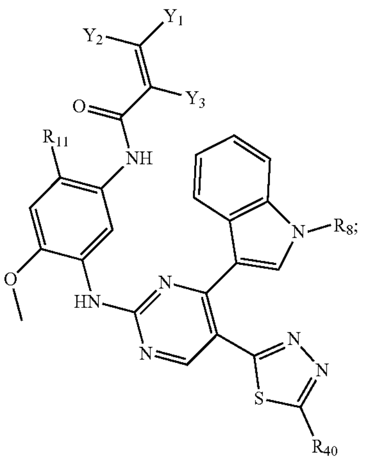

-continued
Formula XII
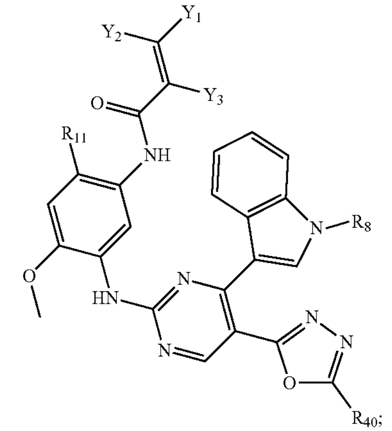
In Formula XI, Formula XII, $R_{11}$ is selected from
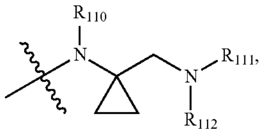
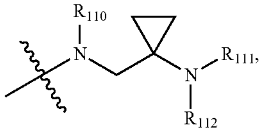
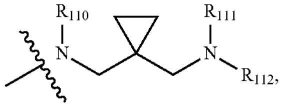
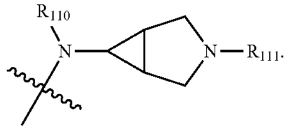
Preferably, a compound of the following structural formulae is used:
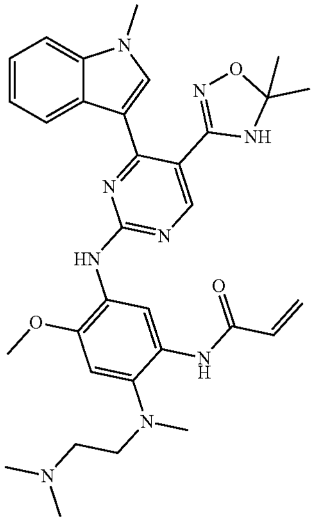
-continued
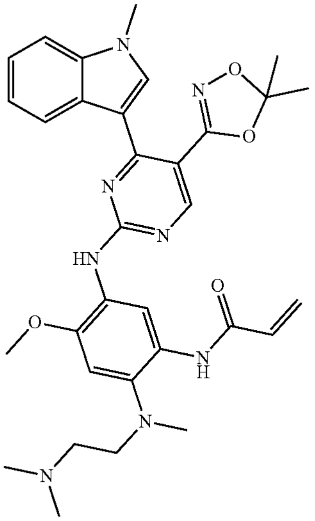
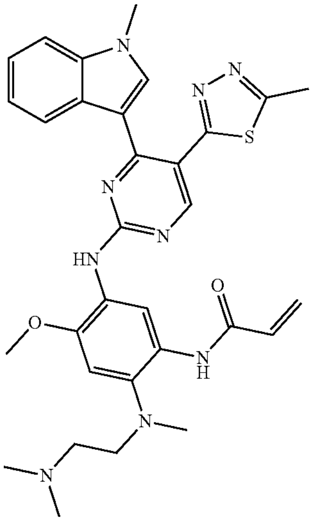
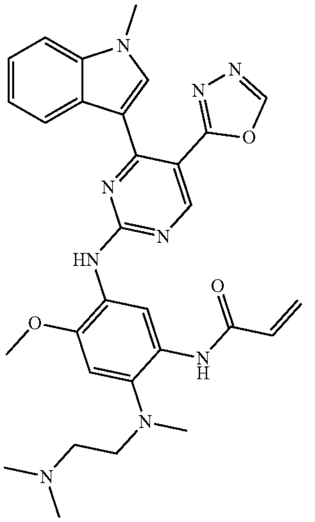

-continued
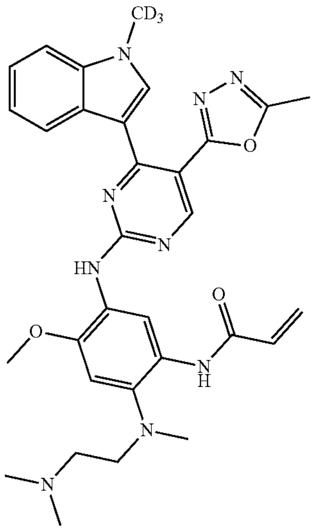
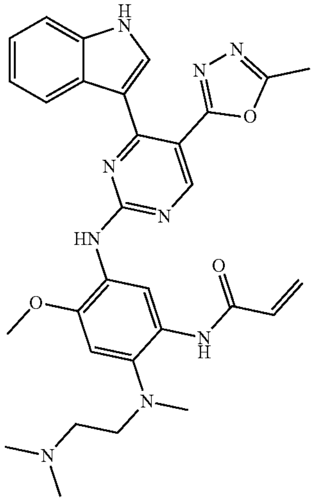
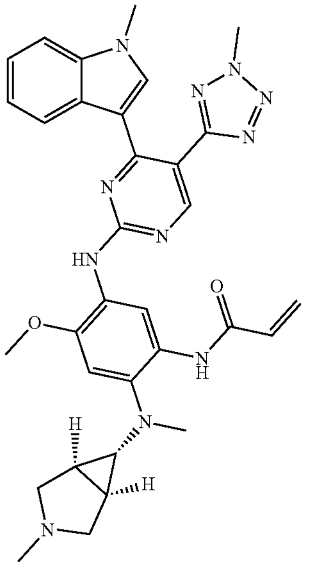
-continued
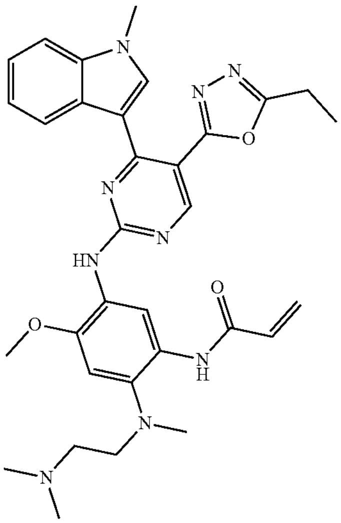
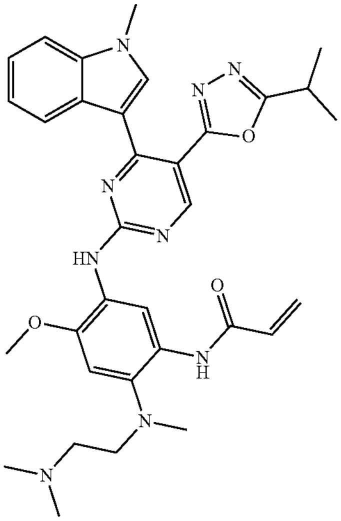
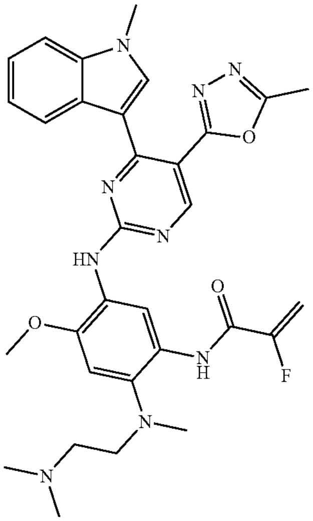

-continued
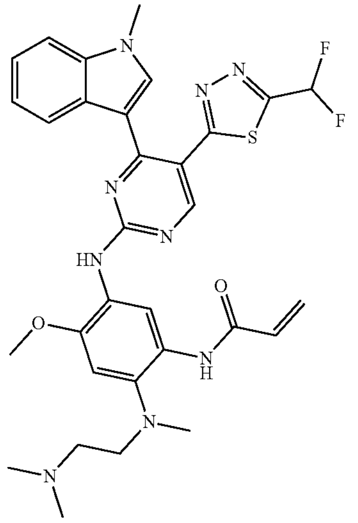
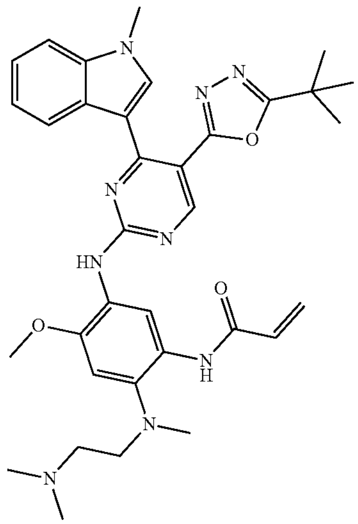
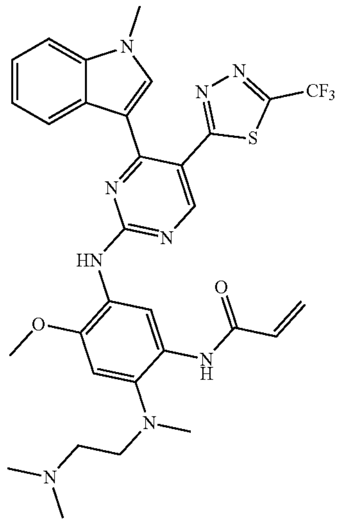
-continued
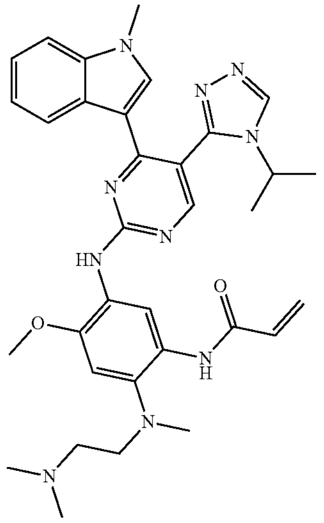
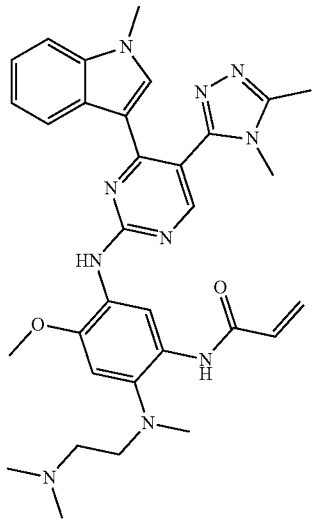
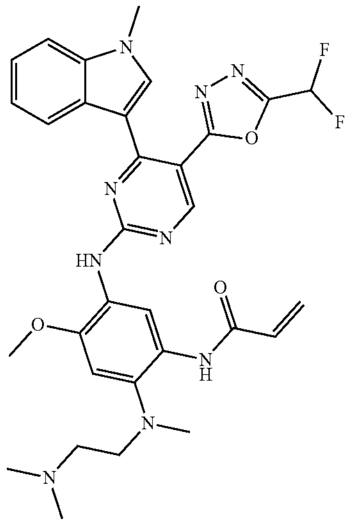

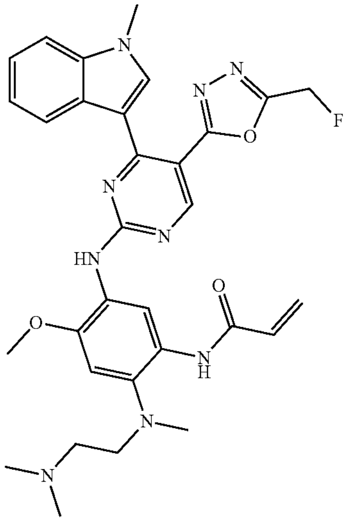
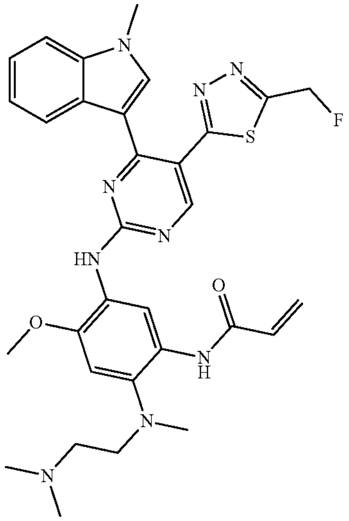
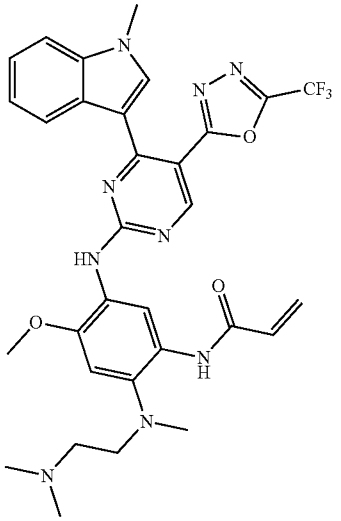
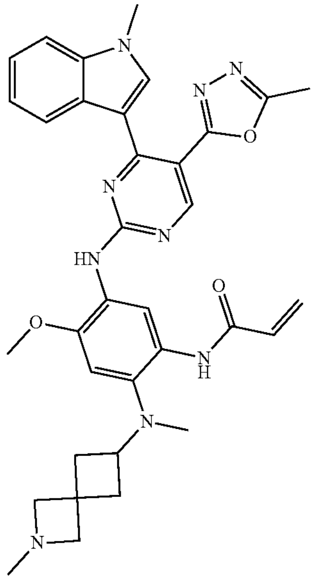
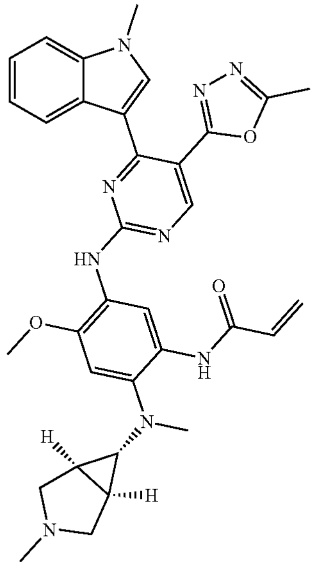

-continued
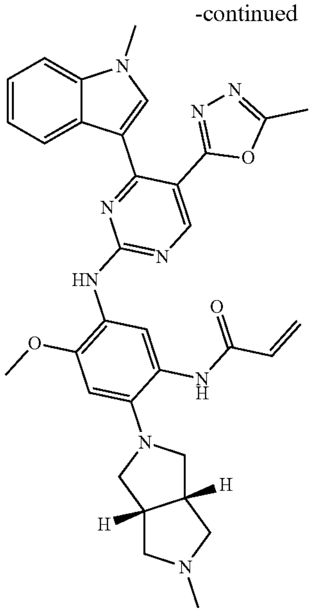
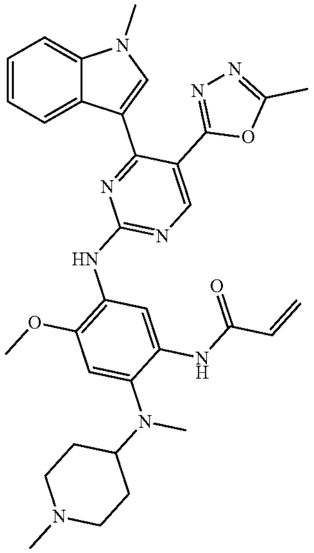
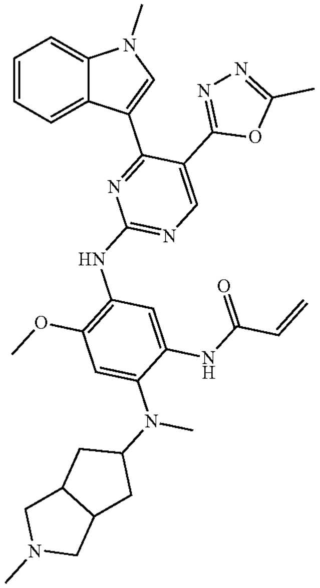
-continued
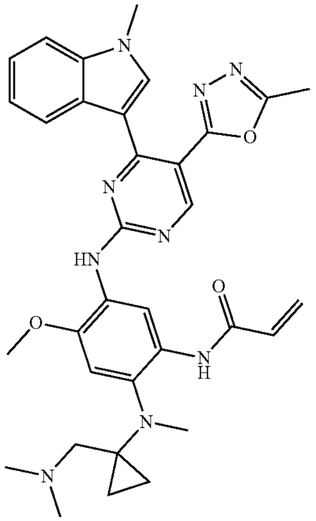
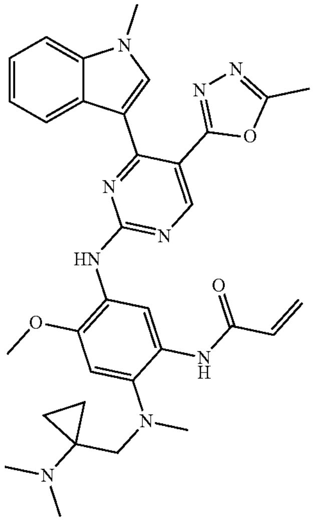
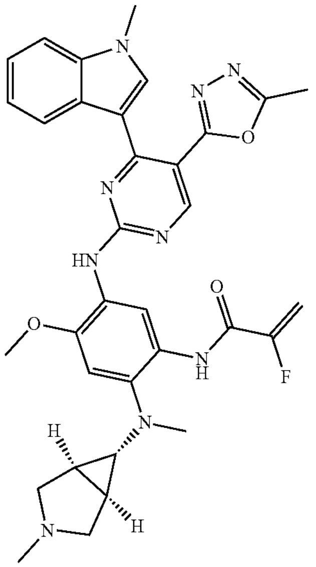

-continued
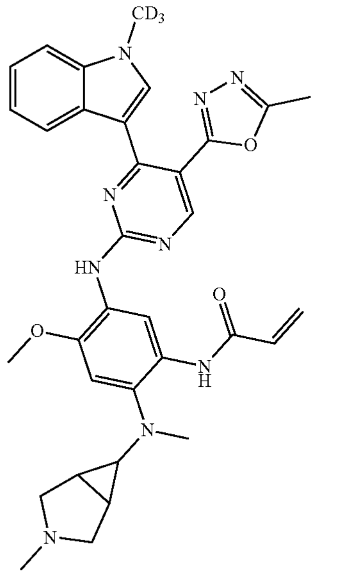
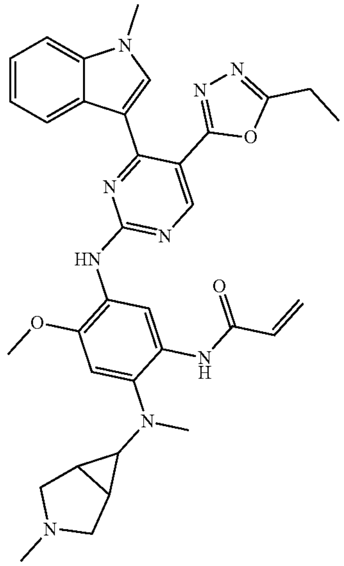
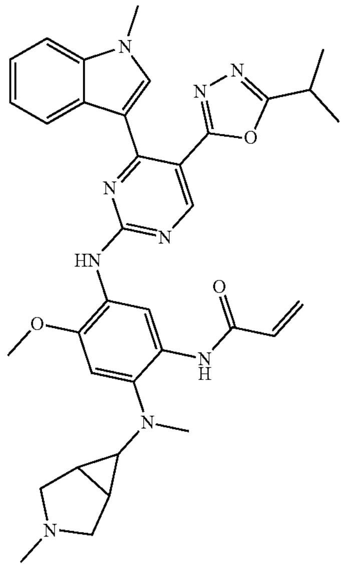
-continued
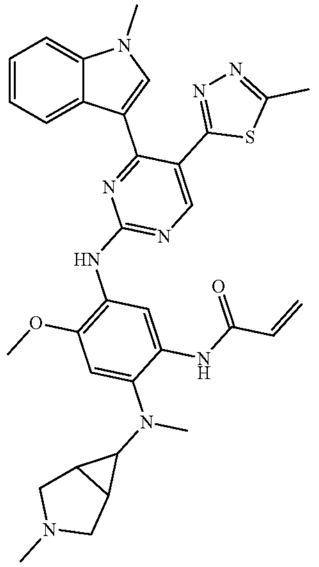
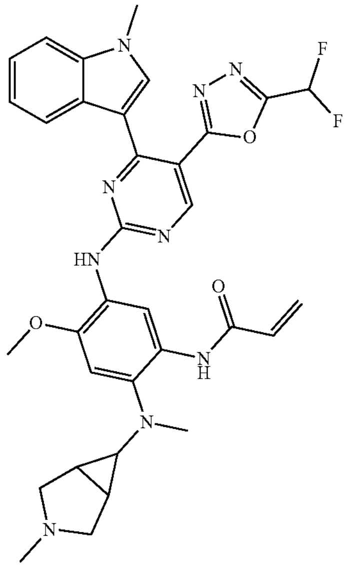
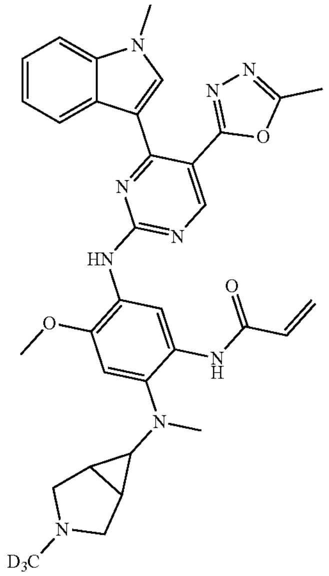

-continued
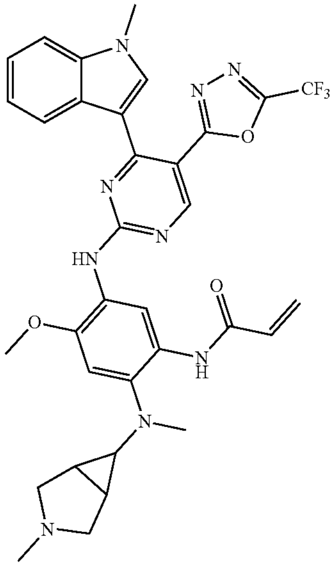
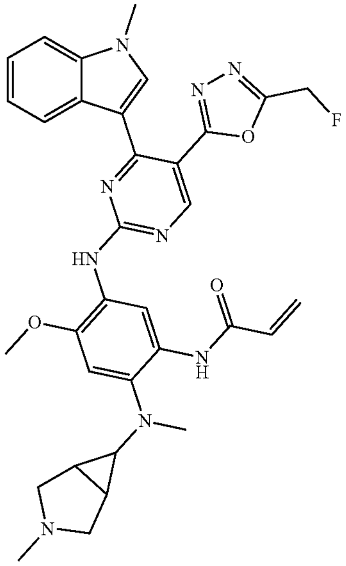
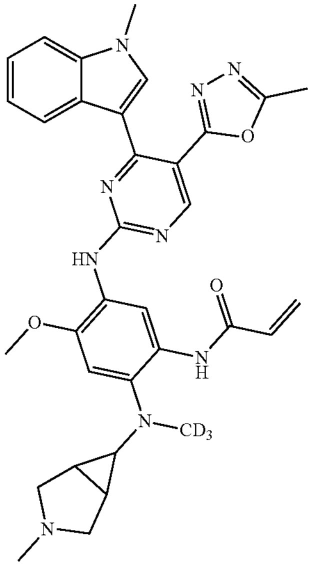
-continued
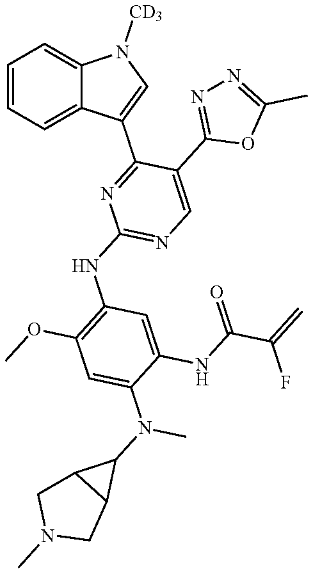
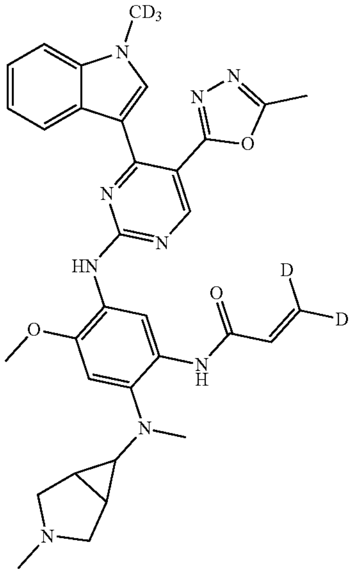
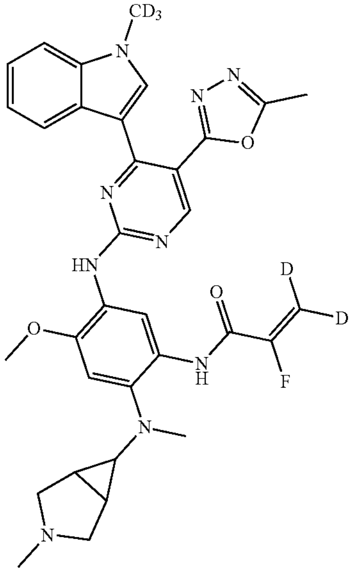

-continued
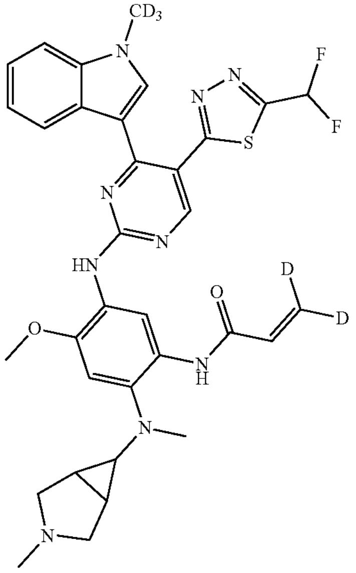
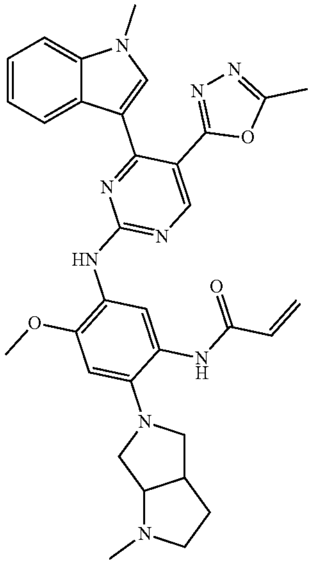
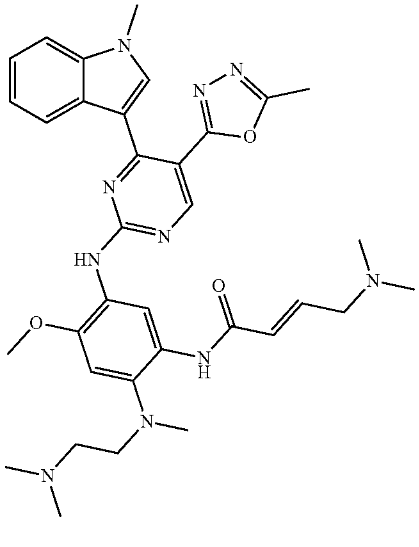
-continued
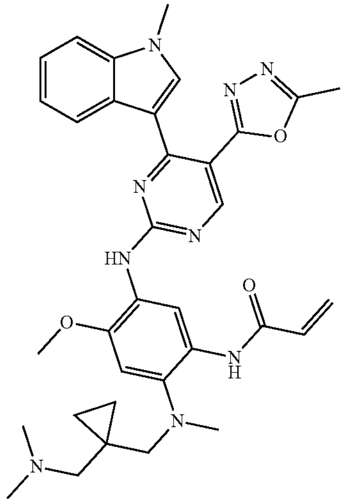
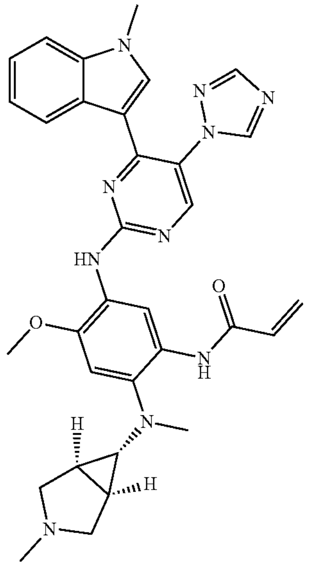
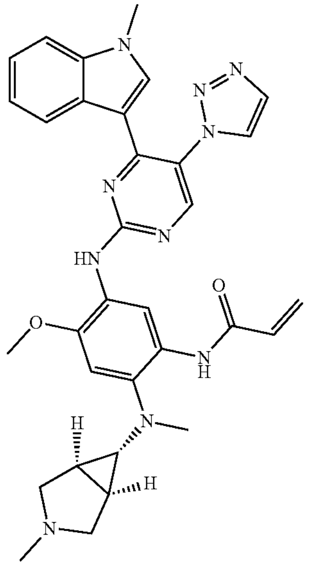

-continued

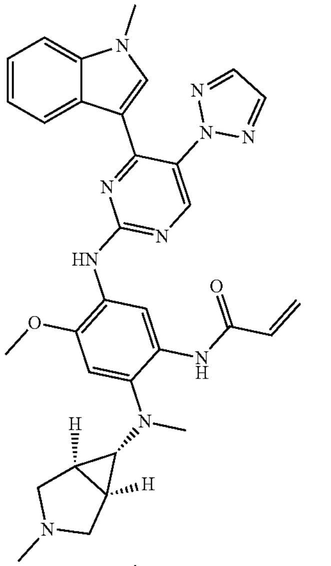

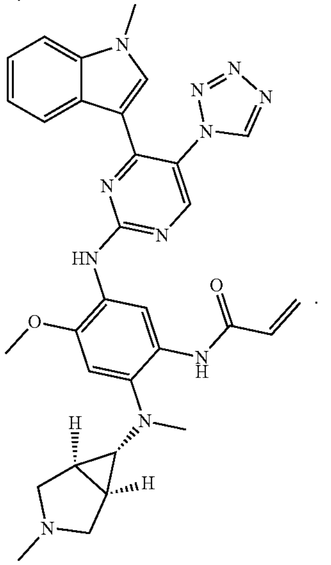

Preferably, a compound represented by Formula X is used:

Formula X'

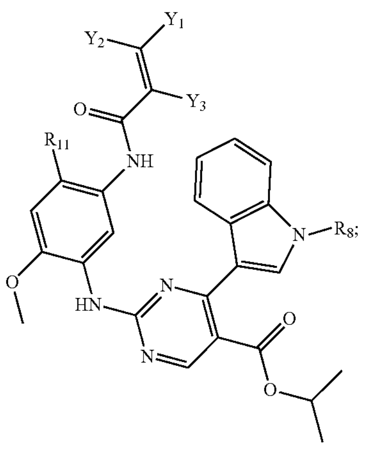

In Formula X', $R_8$ is selected from H, $C_{1-4}$ alkyl, deuterium of $C_{1-4}$ alkyl, $C_{1-4}$ haloalkyl;

$Y_1$, $Y_2$, $Y_3$ are each independently selected from H, D, halogen, $C_{1-4}$ haloalkyl, deuterium of $C_{1-4}$ alkyl, $—CH_2NR_{111}R_{112}$, or

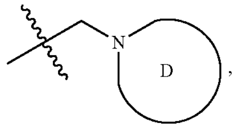

wherein D ring is 4-6 membered cycloalkylamino or 4-6 membered heterocycloalkylamino, the heterocycloalkylamino is that 1 to 3 ring carbon atoms in cycloalkylamino are substituted by heteroatoms, heteroatoms are selected from O, S, or N;

$R_{11}$ is selected from

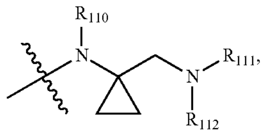

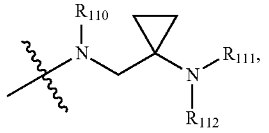

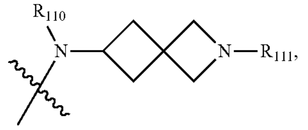

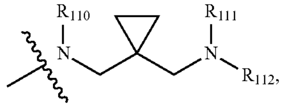

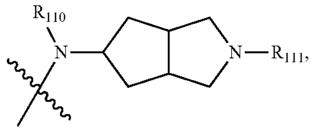

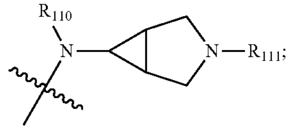

wherein $R_{110}$, $R_{111}$, $R_{112}$ are each independently selected from H, $C_{1-4}$ alkyl, deuterium of $C_{1-4}$ alkyl, or $C_{1-4}$ haloalkyl.

More preferably, a compound of the following structural formulae is used:

-continued

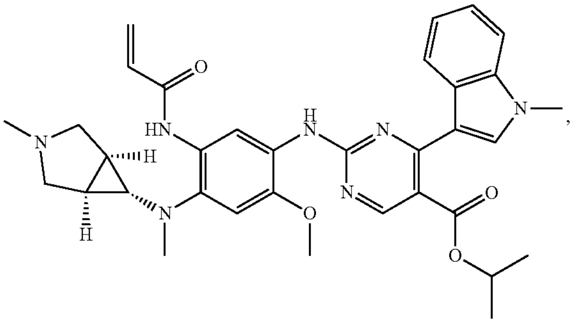
,

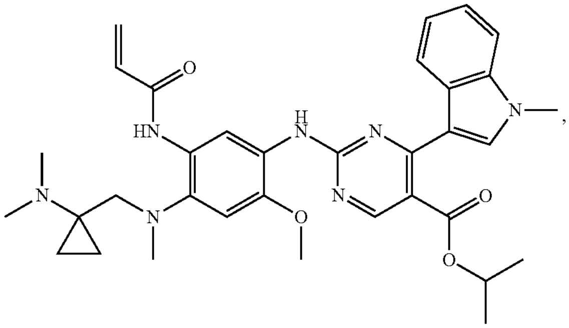
,

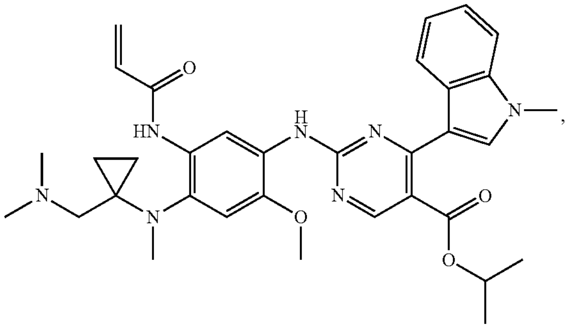
,

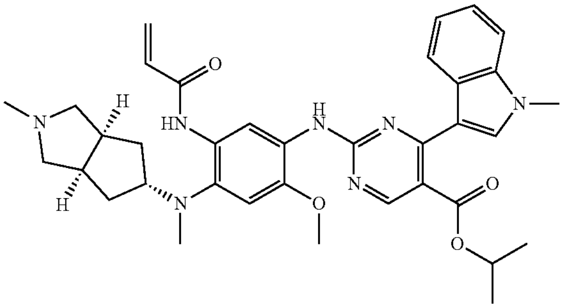
,

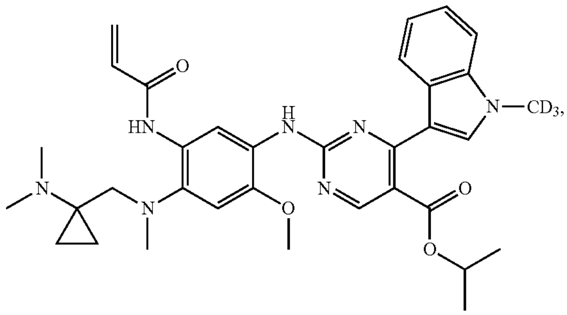
,

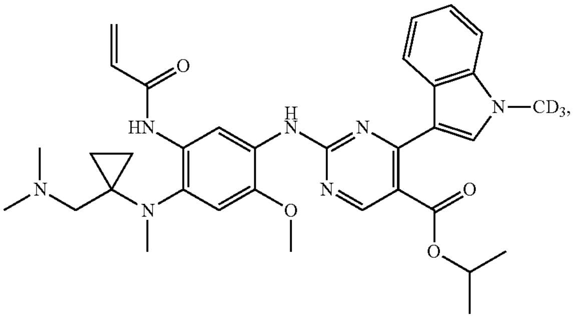
,

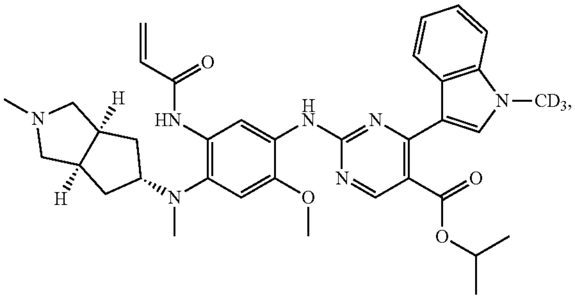
,

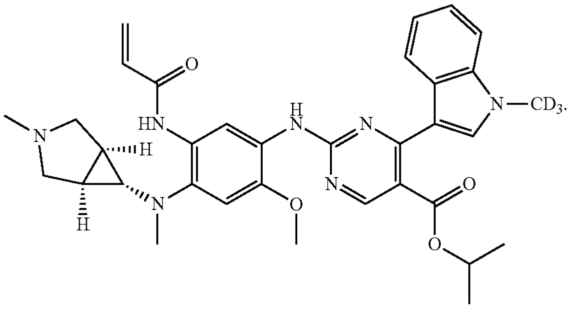
.

Unless otherwise specified, the following terms used in the specification and the claims have the following meanings:

$C_{6-10}$ aryl is a monocyclic or bicyclic aromatic hydrocarbon with 6 to 10 ring atoms, such as phenyl or naphthyl.

5-10 membered heteroaryl refers to a monocyclic or bicyclic aromatic group with 5 to 10 ring atoms, wherein one or more, preferably one, two, or three ring atoms are heteroatoms selected from N, O, S, the remaining ring atoms are carbon. A representative example includes, but is not limited to, pyrrolyl, thienyl, thiazolyl, imidazolyl, furanyl, indolyl, isoindolyl, oxazolyl, isoxazolyl, benzothiazolyl, benzoxazole, quinolinyl, isoquinolinyl, pyridyl, pyrimidinyl, pyrazinyl, pyridazinyl, triazolyl, tetrazolyl, etc.

5-10 membered aliphatic heterocyclyl refers to a monocyclic or bicyclic non-aromatic group with 5 to 10 ring atoms, wherein one or more, preferably one, two, or three, ring atoms are heteroatoms selected from N, O, S, the remaining ring atoms are carbon.

Alkylamino refers to a —NR'R" group, wherein R' and R" are selected from hydrogen or alkyl, and R' and R" are not hydrogen at the same time, such as methylamino, ethylamino, propylamino, dimethylamino, diethylamino, ethylmethylamino, propylmethylamino, etc.

Cycloalkylamino refers to having the following structures of

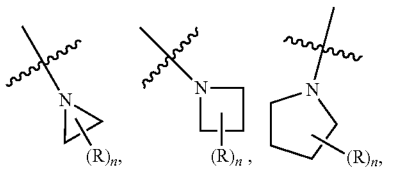

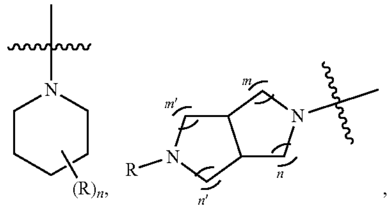

,

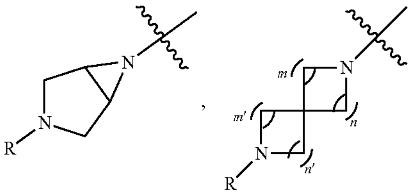

, etc., wherein R is alkyl, m, n, m', and n' are each independently selected from 0, 1, 2, 3, or 4, but m and n are not 0 at the same time, m' and n' are not 0 at the same time.

Phosphoroxy is a group with a structure of

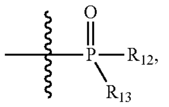

and the meanings of $R_{12}$, $R_{13}$ are as described above.

Haloalkyl, haloalkoxy, halocycloalkyl, halocycloalkoxy, haloalkylamino, halocycloalkylamino are groups formed by substituting hydrogen in corresponding groups, such as alkyl, by halogen, the number of specific substitutions may be one or more.

Haloalkyl may be mono-, di-, or tri-substituted, substituted halogen is preferably fluorine. The number of deuterium in deuterium of alkyl may be one, two, three, . . . , or all.

"" represents the chemical bond connection position.

The above compounds are confirmed through biological activity experiments to have good inhibitory activity on EGFR and Her2 exon 20 insertion mutations, exon 19 deletion, and L858R point mutation of exon 21, and may be used as an original drug of related drugs.

On the basis of the original drug, a "pharmaceutically acceptable salt" of the original drug refers to a salt that is pharmaceutically acceptable and possesses the desired pharmacological activity of the parent compound. Such salt includes the following.

An acid addition salt formed with an inorganic acid. The inorganic acid is, for example, hydrochloric acid, hydrobromic acid, hydroiodic acid, sulfuric acid, nitric acid, phosphoric acid, etc. A typical inorganic acid salt is selected from hydrochloride, hydrobromide, hydroiodide, sulfate, bisulfate, nitrate, phosphate, acid phosphate. An acid addition salt with an organic acid. The organic acid is, for example, formic acid, acetic acid, propionic acid, caproic acid, cyclopentane propionic acid, ethanol acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethyl acetic acid, tert-butyl acetic acid, dodecyl sulfuric acid, gluconic acid, glutamic acid, xinafoic acid, salicylic acid, stearic acid, muconic acid, etc.; or a salt formed by coordinating an acidic proton present in the parent compound with an organic base (for example, ethanol amine, diethanol amine, triethanol amine, tromethamine, N-methylglucamine, etc.). A typical organic acid salt is selected from formate, acetate, trifluoroacetate, propionate, pyruvate, glycolate, oxalate, malonate, fumarate, maleate, lactate, malate, citrate, tartrate, mesylate, ethanesulfonate, isethionate, besylate, salicylate, picrate, glutamate, ascorbate, camphorate, camphorsulfonate. It is readily understood that the pharmaceutically acceptable salt is non-toxic.

A solvate is a compound containing a solvent, such as hydrate, dimethyl sulfoxide, etc.

A prodrug refers to a compound, which is chemically transformed through metabolism or a chemical process to produce the compound, the salt, or the solvate in the disclosure when treating related diseases.

The technical solution of the application of the compound of the disclosure is as follows.

The application of the compound used as the kinase inhibitor in the preparation of a drug for treating related diseases caused by EGFR mutation and/or Her2 mutation.

Based on the good inhibitory activity of the compound on EGFR and Her2 exon 20 insertion mutations, and the expected good inhibitory activity on EGFR exon 19 deletion and L858R point mutation of exon 21, the drug based on the compound is expected to have preferred treatment effect for related diseases.

Preferably, the EGFR mutation and/or the Her2 mutation is exon 20 insertion mutation, EGFR exon 19 deletion, or L858R point mutation of EGFR exon 21. The compound is confirmed through the biological activity experiments to have good inhibitory effect on the above mutation types of exon 20 of the above two kinases.

The compound may also be used in combination with other drugs for treating cancer. The other combined drugs may be an ERK inhibitor or an MEK inhibitor. The cancer is preferably lung cancer, more preferably lung cancer caused by EGFR and Her2 exon 20 insertion mutations, EGFR exon 19 deletion, and L858R point mutation of exon 21.

DETAILED DESCRIPTION OF DISCLOSED EMBODIMENTS

The technical solutions of the disclosure are further described below, but the protection scope of the disclosure is not limited thereto. The following mainly includes the chemical experiment part and the biological experiment part.

I. Chemical Experiment Part

1. Intermediates Involved in the Embodiments Will be Described Below.

Intermediate 1

Synthetic Route:

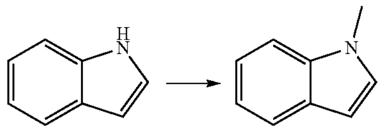

INT 1

Indole (20 g, 170.9 mmol), iodomethane (48.5 g, 341.8 mmol), and cesium carbonate (111 g, 341.8 mmol) were added to N,N-dimethylformamide, reacted for 16 h at room temperature, monitored by TLC. After the raw materials were reacted, water and ethyl acetate were added to the reaction system, the aqueous phase was extracted three times, spin-dried, and 22 g of product was obtained after chromatographic column purification. $^1$HNMR (400 MHz, $CDCl_3$) δ 7.62 (dt, J=8.0, 1.2 Hz, 1H), 7.29 (dt, J=8.0, 1.2 Hz, 1H), 7.21 (ddd, J=8.0, 6.8, 1.2 Hz, 1H), 7.10 (ddd, J=8.0, 6.8, 1.2 Hz, 1H), 7.00 (d, J=3.2 Hz, 1H), 6.47 (dd, J=3.2, 0.8 Hz, 1H), 3.72 (s, 3H).

Intermediate 2

Synthetic Route:

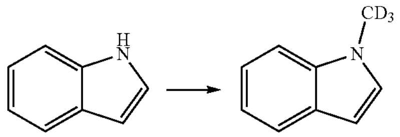

INT 2

Indole (5 g, 42.7 mmol), deuterated iodomethane (9.3 g, 64.1 mmol), and cesium carbonate (21 g, 64.6 mmol) were added to N,N-dimethylformamide and reacted for 16 h at room temperature, monitored by TLC. After the raw materials were reacted, water and ethyl acetate were added to the reaction system, the aqueous phase was extracted three times, spin-dried, and 5.3 g of product was obtained after chromatographic column purification. $^1$HNMR (400 MHz, $CDCl_3$) δ 7.63 (dq, J=8.1, 1.1 Hz, 1H), 7.27 (dt, J=8.2, 1.0 Hz, 1H), 7.21 (ddd, J=8.3, 6.8, 1.2 Hz, 1H), 7.11 (ddd, J=8.2, 6.8, 1.2 Hz, 1H), 6.97 (d, J=3.1 Hz, 1H), 6.47 (dd, J=3.0, 1.3 Hz, 1H).

Intermediate 3

Synthetic Route:

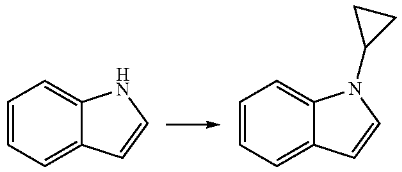

INT 3

Indole (5.3 g, 45.3 mmol), bromocyclopropane (9.8 g, 81.5 mmol), and potassium hydroxide (5.4 g, 81.5 mmol) were added to N,N-dimethylformamide and reacted for 2 h at 0° C., monitored by TLC. After the raw materials were reacted, ice water and ethyl acetate were added to the reaction system, the aqueous phase was extracted three times, spin-dried, and 2.8 g of product was obtained after chromatographic column purification.

Intermediate 4

Synthetic Route:

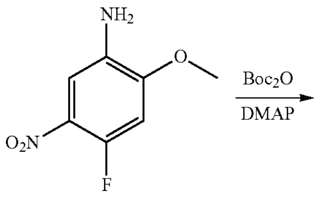

1

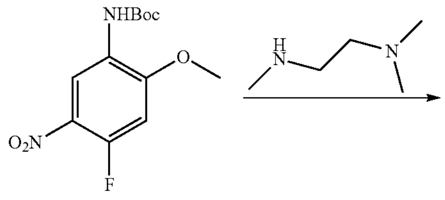

2

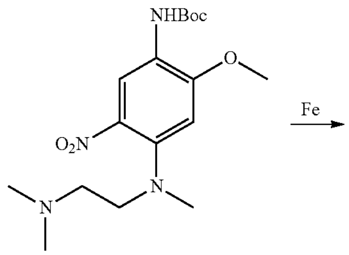

3

-continued

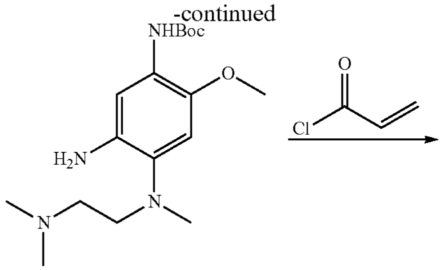

4

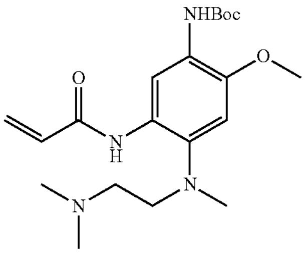

INT 4

Synthesis of Compound 2: Compound 1 (20 g, 107.5 mmol) and DMAP (2.62 g, 21.5 mmol) were dissolved in dichloromethane, temperature was lowered to 0° C. under nitrogen protection, a dichloromethane solution of $Boc_2O$ (25.78 g, 118.2 mmol) was then slowly added dropwise. After the dropwise addition, temperature was raised to room temperature, reacted for 16 h. After the raw materials were reacted, spin-dried, 25 g of product was obtained after chromatographic column purification. $^1$HNMR (400 MHz, $CDCl_3$) δ 8.88 (d, J=8.4 Hz, 1H), 6.99 (s, 1H), 6.72 (d, J=12.0 Hz, 1H), 3.98 (s, 3H), 1.54 (s, 9H).

Synthesis of Compound 3: Compound 2 (20 g, 69.9 mmol), N,N,N-trimethylethylenediamine (10.68 g, 104.8 mmol), and DIPEA (18.16 g, 139.8 mmol) were dissolved in N,N-dimethylacetamide, temperature was raised to 90° C., reacted for 16 h. After reacting, water and ethyl acetate were added to the reaction system for extraction, the organic phase was combined, dried and spin-dried to obtain 30 g of product.

Synthesis of Compound 4: Compound 3 (30 g, 81.3 mmol), iron powder (31.8 g, 56.9 mmol), and ammonium chloride (30.4 g, 56.9 mmol) were dissolved in ethanol/water, temperature was raised to 85° C., reacted for 3 h. After reacting, filter, most of the solvent was spun off, ammonia water was then added to the reaction system, pH was adjusted to 9-10, extracted with dichloromethane three times, 24 g of product was obtained after spin-drying. $^1$HNMR (400 MHz, $CDCl_3$) δ 7.54 (s, 1H), 6.97 (s, 1H), 6.62 (s, 1H), 3.79 (s, 3H), 3.54 (m, 4H), 3.09 (t, J=6.4 Hz, 2H), 2.68 (d, J=6.4 Hz, 2H), 2.65 (s, 3H), 2.50 (s, 6H), 1.50 (s, 9H).

Synthesis of INT 4: Compound 4 (5 g, 14.7 mmol) and triethylamine (4.48 g, 44.3 mmol) were dissolved in dichloromethane, temperature was lowered to 0° C. under nitrogen protection. A dichloromethane solution of acryloyl chloride (1.48 g, 16.2 mmol) was then slowly added dropwise, reacted for 2 h while maintaining at 0° C., after reacting, water and dichloromethane were added to the reaction system, extracted, spin-dried, 3.3 g of product was obtained after chromatographic column purification. $^1$HNMR (400 MHz, $CDCl_3$) δ 10.05 (s, 1H), 9.12 (s, 1H), 6.91 (s, 1H), 6.71 (s, 1H), 6.43 (dd, J=17.2, 1.6 Hz, 1H), 6.27 (dd, J=16.8, 10.0 Hz, 1H), 5.66 (dd, J=10.0, 1.6 Hz, 1H), 3.82 (s, 3H), 2.89-2.82 (m, 2H), 2.66 (s, 3H), 2.30-2.26 (m, 2H), 2.25 (s, 6H), 1.52 (s, 9H).

Intermediate 5

Synthetic Route:

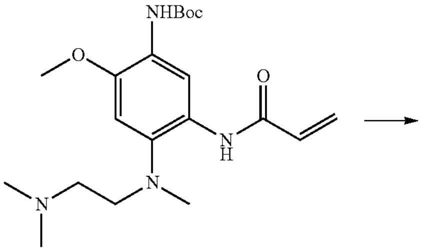

INT 4

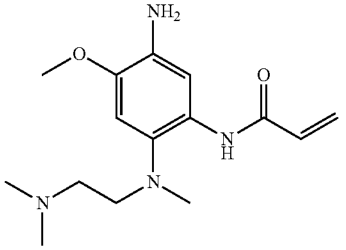

INT 5

23 g of raw material INT 4 was dissolved in 50 ml of THF. An ice-salt bath was cooled to −5° C., added dropwise to 100 ml of concentrated hydrochloric acid, temperature was T<10° C., after stirring for 2 hours, dot plate reaction was completed. Processed, passed through a chromatographic column. 5.2 g of product was obtained. $^1$HNMR ($CDCl_3$) δ 10.10 (s, 1H), 7.97 (s, 1H), 6.68 (s, 1H), 6.41-6.21 (m, 2H), 5.65 (m, 1H), 3.81 (s, 3H), 3.76 (s, 2H), 2.82 (m, 2H), 2.65 (s, 3H), 2.20 (s, 6H).

Intermediate 6

Synthetic Route is as Follows:

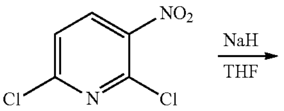

1

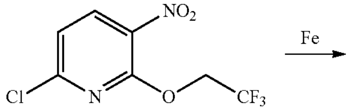

2

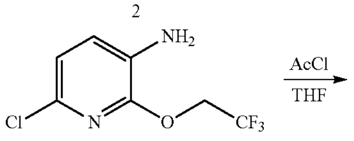

3

-continued

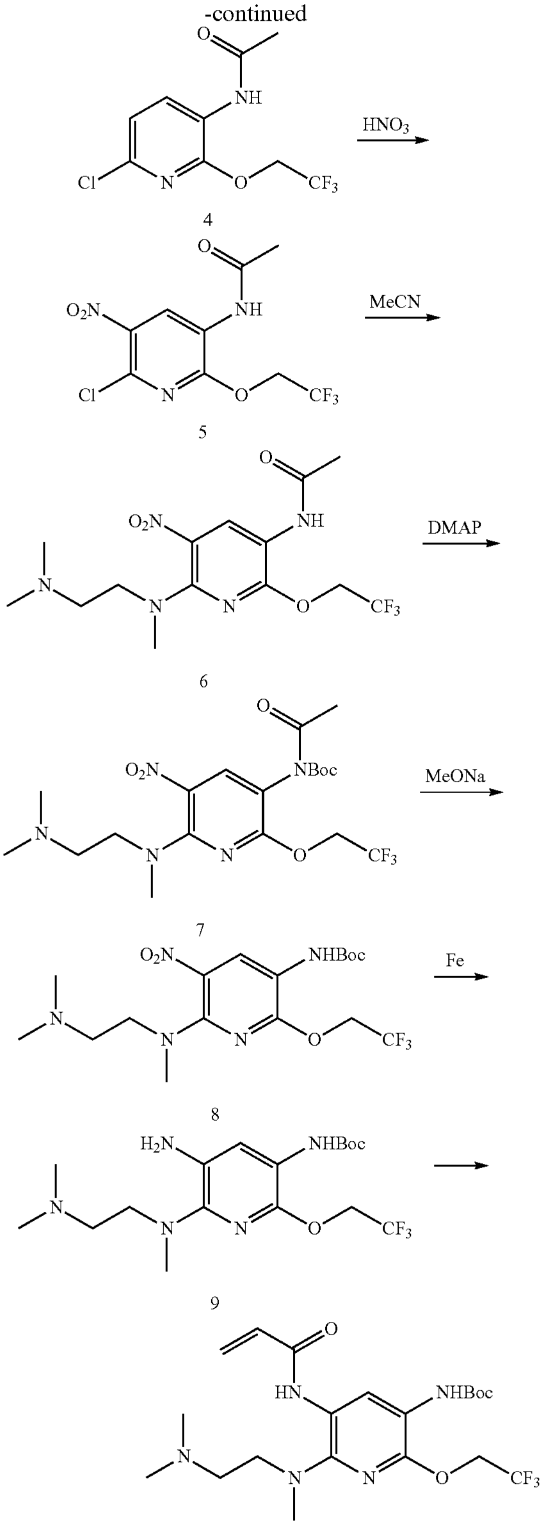

4

5

6

7

8

9

INT 6

Synthesis of Compound 2: in a 2000 mL three-necked flask, Compound 1 (50 g, 0.26 mol), trifluoroethanol (29.61 g, 0.26 mol), and 700 mL of dry THF were respectively added, at 0° C., under nitrogen protection condition, NaH (12 g, 0.286 mol) was added in batches, then stirred at room temperature overnight. After TLC detected completion of reaction, a saturated aqueous ammonium chloride solution was added, extracted with ethyl acetate three times, washed with saturated brine, dried, spin-dried, passed through a chromatographic column to obtain 53 g of product. $^1$HNMR: ($CDCl_3$, 400 MHz) δ 8.36 (d, J=8.0 Hz, 1H), 7.19 (d, J=8.4 Hz, 1H), 4.94-4.88 (m, 2H).

Synthesis of Compound 3: in a 2000 mL three-necked flask, Compound 2 (40 g, 0.156 mol), $NH_4Cl$ (42 g, 0.78 mol), 600 mL of ethanol, and 200 mL of water were added, temperature was raised to 80° C. under nitrogen protection, iron powder (44 g, 0.78 mol) was added in batches, stir-reacted for 2 h after adding, TLC showed that the reaction was completed. Cooled to room temperature, filtered, the filtrate was spin-dried, 1000 mL of ethyl acetate was added, washed with water, dried, spin-dried to obtain 30 g of product. $^1$HNMR: ($CDCl_3$, 400 MHz) δ 6.93 (d, J=7.6 Hz, 1H), 6.83 (d, J=8.0 Hz, 1H), 4.78-4.74 (m, 2H), 3.82 (s, 2H).

Synthesis of Compound 4: in a 1000 mL three-necked flask, Compound 3 (30 g, 0.132 mol), DIPEA (33 mL, 0.192 mol), 600 mL of dichloromethane were added, under nitrogen protection, temperature was lowered to 0° C. Acetyl chloride (12 g, 0.169 mol) was added dropwise, after the dropwise addition, stir-reacted for 3 h at 0° C., tracked and monitored with dot plate. After reacting, 100 mL of water and 400 mL of 1N hydrochloric acid aqueous solution were added, extracted with dichloromethane three times, the organic phase was combined, washed with water, dried, and spin-dried to obtain 24 g of product. $^1$HNMR: ($CDCl_3$, 400 MHz) δ 8.67 (d, J=8.0 Hz, 1H), 7.43 (s, 1H), 7.03 (d, J=8.4 Hz, 1H), 4.85-4.79 (m, 2H), 2.24 (s, 3H).

Synthesis of Compound 5: in a 500 mL three-necked flask, trifluoroacetic anhydride (200 mL), Compound 4 (20 g, 75 mmol) were added, temperature was then lowered to −10° C., fuming nitric acid (3.5 mL) was slowly added, temperature was maintained at −5° C., under such temperature condition, stirred for 1 h, tracked with dot plate until reaction was completed. The reaction solution was poured into crushed ice, extracted with ethyl acetate three times, dried, spin-dried, passed through a chromatographic column to obtain 16 g of product. $^1$HNMR: (DMSO-d6, 400 MHz) δ 9.95 (s, 1H), 9.18 (s, 1H), 5.17-5.15 (m, 2H), 2.18 (s, 3H).

Synthesis of Compound 6: in a 250 mL single-necked flask, Compound 5 (10.4 g, 33.2 mmol), N,N,N-trimethylethylenediamine (5.08 g, 49.8 mmol), 100 mL of acetonitrile were added. Temperature was then raised to 80° C. under nitrogen protection, stirred overnight. Tracked with dot plate, after reaction was completed, the reaction solution was spin-dried, methyl tert-butyl ether was added and pulped, filtered, dried to obtain 8.6 g of product. $^1$HNMR: (DMSO-d6, 400 MHz) δ 9.50 (s, 1H), 8.60 (s, 1H), 5.17-5.15 (m, 2H), 4.05 (t, d=7.6 Hz, 2H), 3.36 (t, d=7.4 Hz, 2H), 2.83 (s, 3H), 2.79 (s, 6H), 2.08 (s, 3H).

Synthesis of Compound 7: in a 250 mL single-necked flask, 160 mL of THF, Compound 6 (8 g, 20.8 mmol), DMAP (0.72 g, 2.08 mmol), $Boc_2O$ (44.8 g, 208 mmol) were added, temperature was then raised to 80° C. under nitrogen protection, stir-reacted for 2 h, tracked with dot plate until reaction was completed. Processed, passed through a chromatographic column to obtain 8 g of product with a yield of 83%.

Synthesis of Compound 8: in a 250 mL three-necked flask, 150 mL of anhydrous methanol, Compound 7 (8 g, 16.6 mmol) were added, under nitrogen protection, temperature was lowered to 0° C., sodium methoxide (1.18 g, 21.9 mmol) was added in batches, then stir-reacted for 1 h under such condition, tracked with dot plate until reaction was completed. Water was added, extracted with ethyl acetate three times, the organic phase was combined, washed with water, dried, spin-dried to obtain 7.2 of product with a yield of 90%.

Synthesis of Compound 9: in a 250 mL three-necked flask, Compound 8 (6.1 g, 14 mmol), $NH_4Cl$ (3.7 g, 53.4 mmol), 90 mL of ethanol, and 30 mL of water were added, temperature was raised to 80° C. under nitrogen protection, iron powder (3.9 g, 70 mmol) was added in batches. After addition was completed, stir-reacted for 2 h under such condition. Tracked with dot plate until reaction was completed. Cooled to room temperature, filtered, the filtrate was spin-dried, ethyl acetate and brine were added, processed, spin-dried to obtain 3.6 g of product with a yield of 64%.

Synthesis of INT6: in a 250 mL three-necked flask, 100 mL of dichloromethane, Compound 9 (3.5 g, 8.6 mmol), triethylamine (1.74 g, 17.2 mmol) were added, under nitrogen protection, temperature was lowered to −5° C., acryloyl chloride (0.851 g, 9.4 mmol) was added in batches, stir-reacted for 0.5 h, tracked with dot plate. After reacting, a saturated aqueous sodium bicarbonate solution was added, extracted with dichloromethane three times, washed with water, dried, spin-dried through a chromatographic column to obtain 1.9 g of product. $^1$HNMR: ($CDCl_3$, 400 MHz) δ 10.13 (s, 1H), 9.38 (s, 1H), 6.60 (s, 1H), 6.43 (d, J=5.6 Hz, 1H) 5.17-5.15 (m, 2H), 4.05 (t, d=7.6 Hz, 2H), 3.36 (t, d=7.4 Hz, 2H), 2.83 (s, 3H), 2.79 (s, 6H), 2.08 (s, 3H).

Intermediate 7

Synthetic Route:

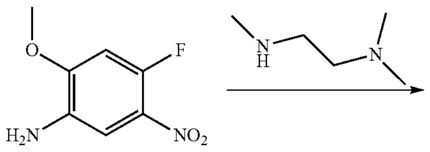

1

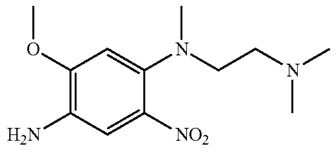

INT 7

Compound 1 (20 g, 107.5 mmol), N,N,N-trimethylethylenediamine (12 g, 118.2 mmol), and potassium carbonate (30 g, 215 mmol) were added to acetonitrile, temperature was then raised to 80° C., reacted for 16 h. After reacting, filtered, the filter cake was washed with ethyl acetate three times, the filtrate was combined, dried, 37 g of product was obtained after spin-drying. $^1$HNMR (400 MHz, $CDCl_3$) δ 7.25 (s, 1H), 6.59 (s, 1H), 3.89 (s, 3H), 3.75 (s, 2H), 3.18-3.09 (m, 2H), 2.79 (s, 3H), 2.50-2.43 (m, 2H), 2.21 (s, 6H).

Intermediate 8

Synthetic Route:

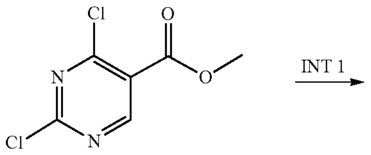

1

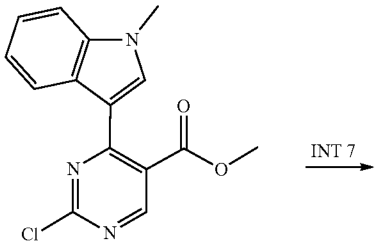

2

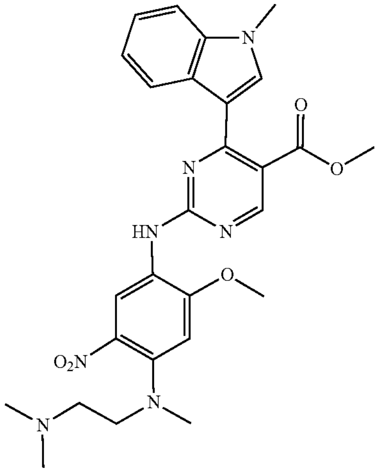

INT 8

Synthesis of Compound 2: Compound 1 (13 g, 62.8 mmol) and aluminum trichloride (9.9 g, 94.2 mmol) were dissolved in 200 mL of dry THF, temperature was raised to 80° C. under nitrogen protection, reacted for 1 h, a THF solution (12.5 g, 75.3 mmol) of INT-1 was slowly added dropwise while stirring, reaction was continued for 3 h at 80° C. after adding, tracked with dot plate. Reaction was completed, processed, passed through a chromatographic column to obtain 8.6 g of product. $^1$HNMR (400 MHz, $CDCl_3$) δ 8.83 (d, J=0.8 Hz, 1H), 8.19-8.13 (m, 1H), 7.98 (s, 1H), 7.40-7.28 (m, 3H), 3.89 (s, 3H), 3.86 (s, 3H).

Synthesis of INT 8: Compound 2 (8.6 g, 28.5 mmol) and Intermediate 7 (9.2 g, 34.2 mmol) were dissolved in dioxane and water, p-toluenesulfonic acid monohydrate (8.14 g, 42.8 mmol) was added while stirring, temperature was raised to 80° C., reacted for 16 h. Tracked with dot plate, after reaction was completed, the reaction solution was spin-dried, 2N aqueous sodium hydroxide solution was added to adjust alkali, then extracted with ethyl acetate three times, dried, spin-dried, passed through a chromatographic column to obtain 9 g of product. $^1$HNMR (400 MHz, $CDCl_3$) δ 9.44 (s, 1H), 8.90 (s, 1H), 8.07 (s, 1H), 7.78 (s, 1H), 7.68 (s, 1H), 7.41-7.35 (m, 1H), 7.30 (d, J=1.2 Hz, 1H), 7.23-7.18 (m, 2H), 6.72 (s, 1H), 4.00 (s, 3H), 3.94 (s, 3H), 3.71 (s, 3H), 3.37 (d, J=7.2 Hz, 2H), 2.90 (s, 3H), 2.70 (s, 2H), 2.37 (s, 6H).

Intermediate 9

Synthetic Route:

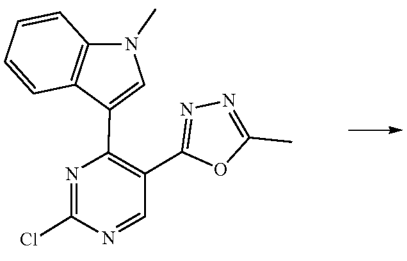

1

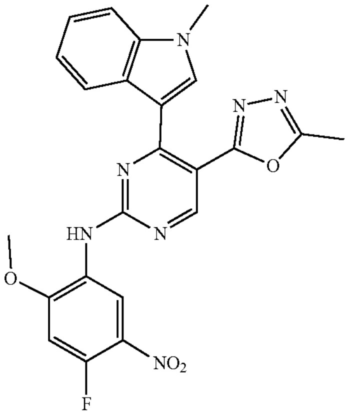

INT 9

Compound 1 (1 g, 3.07 mmol), AZD9291 intermediate (0.686 g, 3.69 mmol), and p-toluenesulfonic acid monohydrate (0.76 g, 3.99 mmol) were added to dry dioxane, temperature was raised to 80° C. under nitrogen protection, reacted for 16 h. Tracked with dot plate, after reaction was completed, processed, passed through a chromatographic column to obtain 0.23 g of product. $^1$HNMR (400 MHz, $CDCl_3$) δ 9.74 (d, J=8.4 Hz, 1H), 8.88 (s, 1H), 8.02 (s, 1H), 7.89 (s, 1H), 7.38 (m, 2H), 7.26 (m, 1H), 7.11 (t, J=7.6 Hz, 1H), 6.79 (d, J=12.0 Hz, 1H), 4.05 (s, 3H), 3.93 (s, 3H), 2.33 (s, 3H).

Intermediate 10

Synthetic Route:

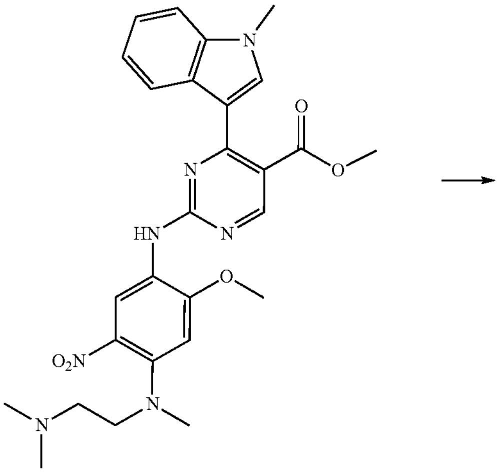

INT 8

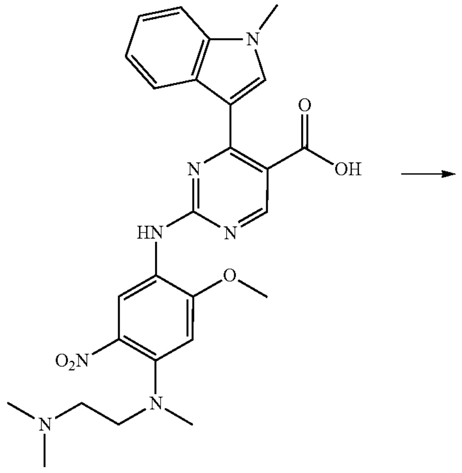

2

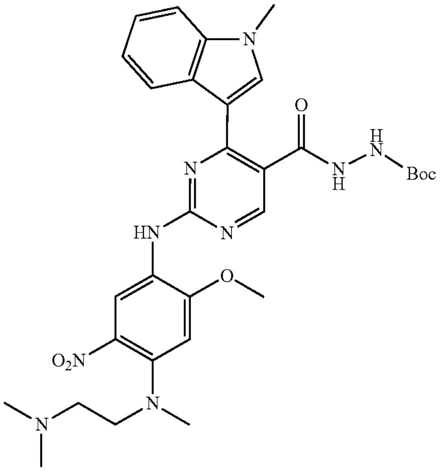

INT 10

Synthesis of Compound 2: INT8 (4.06 g, 7.62 mmol) and lithium hydroxide monohydrate (1.6 g, 38.1 mmol) were added to a mixed solvent of methanol, tetrahydrofuran, and water, reacted for 16 h at 40° C., monitored by TLC, after the raw materials were reacted, spin-dried directly, anhydrous methanol and concentrated hydrochloric acid were then added to neutralize, the solvent was spin-dried, toluene was then used to remove water three times to obtain 6.5 g of crude product, directly put into the next step.

Synthesis of INT 10: Compound 2 (6.5 g), DIPEA (5.8 g, 45 mmol), and tert-butylcarbazate (2.97 g, 22.5 mmol) were dissolved in dry DMF, reacted for 15 min at room temperature, PyBop (4.68 g, 9 mmol) was then added, under nitrogen protection, reacted for 16 h at room temperature, tracked with dot plate. After reaction was completed, water and ethyl acetate were added to the reaction system for extraction, the organic phase was combined, dried, spin-dried, passed through a chromatographic column to obtain 1.9 g of product. $^1$HNMR (400 MHz, DMSO-d6) δ 10.32 (s, 1H), 9.26 (m, 1H), 9.11 (s, 1H), 8.71 (s, 1H), 8.40 (s, 1H), 8.35 (s, 1H), 8.30 (s, 1H), 8.16 (m, 1H), 7.48 (d, J=8.2 Hz, 1H), 7.22 (ddd, J=8.2, 7.0, 1.2 Hz, 1H), 7.04 (t, J=7.6 Hz, 1H), 6.94 (s, 1H), 3.96 (s, 3H), 3.83 (s, 3H), 3.48 (t, J=6.9 Hz, 2H), 3.31 (m, 2H), 2.86 (s, 3H), 2.80 (s, 6H), 1.49 (s, 9H).

2. Specific Examples of the Compound Used as the Kinase Inhibitor are Described Below:

Example 1

The structural formula of the compound used as the kinase inhibitor of the example is:

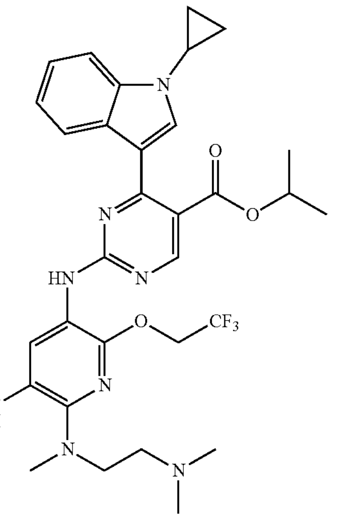

Synthetic Route:

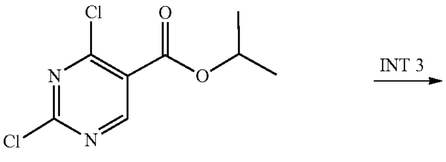

1

-continued

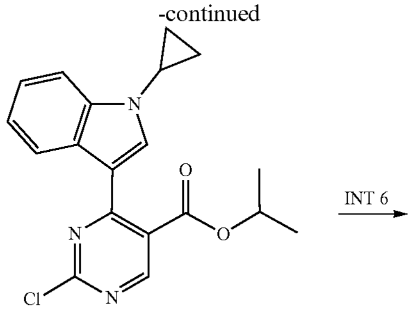

2

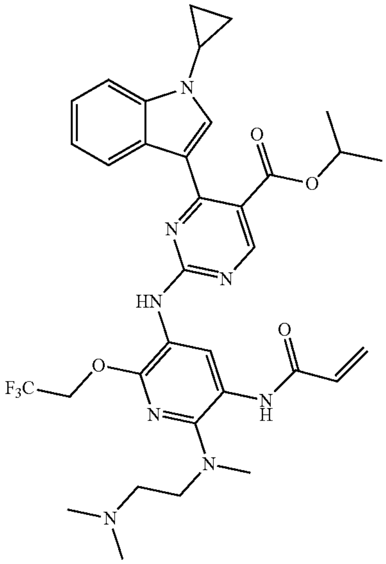

Example 1

Synthesis of Compound 2: in a 100 mL single-necked flask, Compound 1 (0.234 g, 1 mmol), $AlCl_3$ (0.186 g, 1.4 mol), 15 mL of 1,2-dichloroethane were added, heated to 80° C. in an oil bath, stirred for 1 h, cyclopropyl indole (0.16 g, 1 mmol) was then added, stirred for 4 h at 80° C., tracked with dot plate, after reaction was completed, temperature was lowered, poured into ice water, extracted with ethyl acetate three times, the organic phase was combined, dried, passed through a chromatographic column to obtain 0.2 g of product.

Synthesis of Example 1: Compound 2 (50 mg, 0.141 mmol), INT 6 (65 mg, 0.141 mmol), p-toluenesulfonic acid monohydrate (45.5 mg, 0.24 mmol), 1.5 mL of NMP, and 3 mL of ethylene glycol monomethyl ether were added to a 5 mL reactor, heated to 120° C., reacted for 6 h. Tracked with dot plate, after reaction was completed, cooled to room temperature, 10 mL of ethyl acetate was added, washed with an aqueous sodium bicarbonate solution, washed with saturated brine once, dried. 20 mg of product was obtained after purification with a yield of 51%. MS+1: 681.51.

Example 2

The structural formula of the compound used as the kinase inhibitor of the example is:

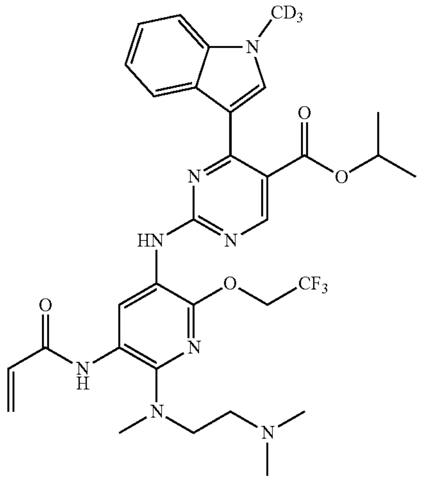 [SMILES: [2H]C([2H])([2H])n1cc(-c2nc(Nc3cc(NC(=O)C=C)c(N(C)CCN(C)C)nc3OCC(F)(F)F)ncc2C(=O)OC(C)C)c2ccccc21]

Synthetic Route:

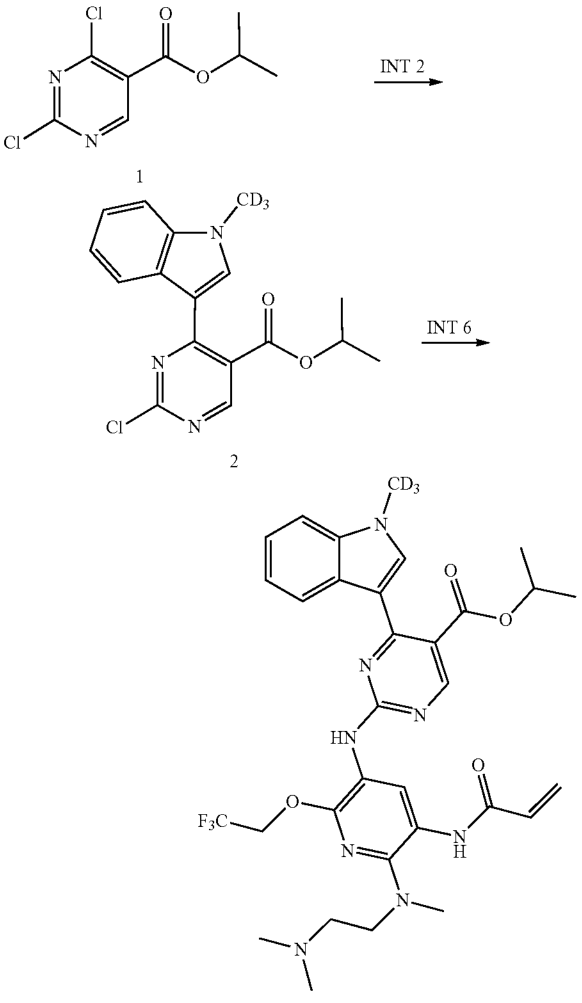

1

2

Example 2

Synthesis of Compound 2: in a 100 mL single-necked flask, Compound 1 (0.234 g, 1 mmol), $AlCl_3$ (0.186 g, 1.4 mol), 15 ml of 1,2-dichloroethane were added, heated to 80° C. in an oil bath, stirred for 1 h, INT2 (0.138 g, 1 mmol) was then added, stirred for 4 hours at 80° C., tracked with dot plate, after reaction was completed, temperature was lowered, poured into ice water, extracted with ethyl acetate three times, the organic phase was combined, dried, passed through a chromatographic column to obtain 0.19 g of product.

Synthesis of Example 2: Compound intermediate 2 (50 mg, 0.152 mmol), INT 6 (70.1 mg, 0.152 mmol), p-toluenesulfonic acid monohydrate (49.1 mg, 0.26 mmol), 1 mL of NMP, and 2 mL of ethylene glycol monomethyl ether were added to a 5 mL reactor, heated to 120° C., reacted for 6 h, tracked with dot plate, after reaction was completed, cooled to room temperature, 10 mL of ethyl acetate was added, washed with an aqueous sodium bicarbonate solution and saturated brine once, dried, purified to obtain 22 mg of product. MS+1: 655.53.

Example 3

The structural formula of the compound used as the kinase inhibitor of the example is:

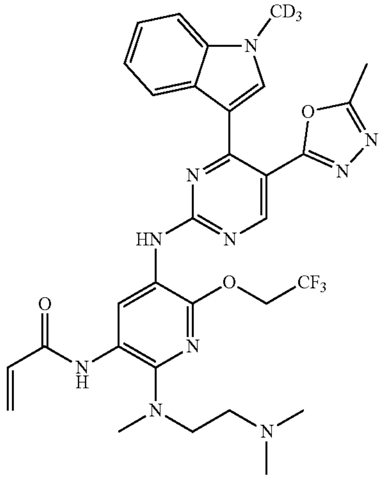 [SMILES: [2H]C([2H])([2H])n1cc(-c2nc(Nc3cc(NC(=O)C=C)c(N(C)CCN(C)C)nc3OCC(F)(F)F)ncc2-c2nnc(C)o2)c2ccccc21]

Synthetic Route:

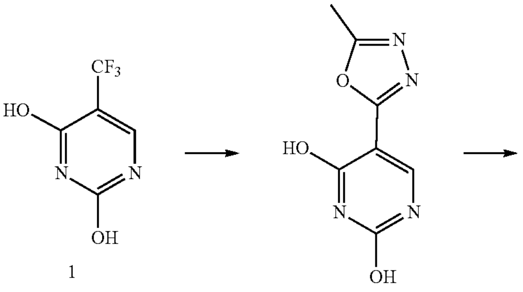

1

2

-continued

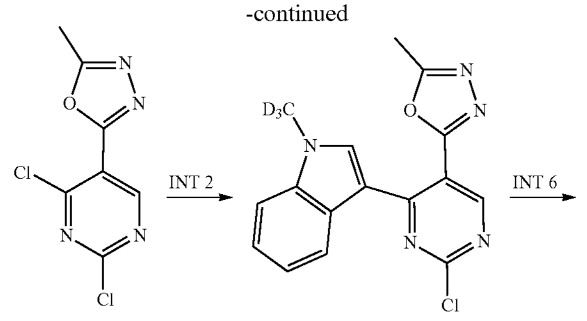

3 4

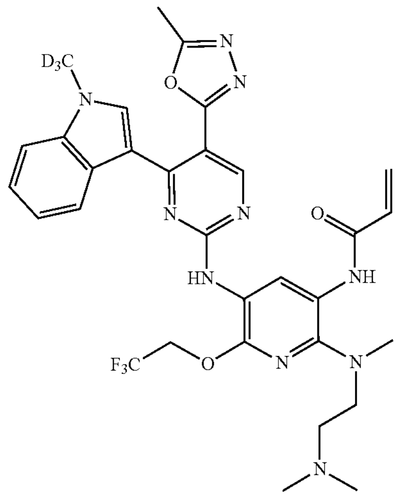

Example

Synthesis of Compound 2: in a 250 ml single-necked flask, Compound 1 (5.53 g, 31 mmol), acetyl hydrazide (2.76 g, 37 mmol) were added, 93 mL of 1N aqueous sodium hydroxide solution was added, reacted for 4 h at 80° C., a large amount of yellow solid was precipitated. Temperature was lowered, stirred for 30 min at a low temperature of about 5° C., filtered with suction, the filter cake was stirred and washed with water once, dried under vacuum overnight at 55° C. to obtain 2.75 g of product.

Synthesis of Compound 3: in a 250 ml single-necked flask, Compound 2 (2.75 g, 14.2 mmol), DIPEA (12.8 g, 0.1 mol), 150 ml of toluene were added, 20 ml of phosphorus oxychloride was added at room temperature, white mist was generated. Put into an oil bath, heated to 80° C., under nitrogen protection, stirred overnight, the next day, the reaction solution was poured into crushed ice, ethyl acetate was added for extraction, extracted three times, the organic phase was combined, dried, passed through a chromatographic column to obtain 1.1 g of product. $^1$HNMR (400 MHz, $CDCl_3$) δ 9.18 (s, 1H), 2.70 (s, 3H).

Synthesis of Compound 4: in a 250 ml single-necked flask, Compound 3 (2.38 g, 10.3 mmol), 120 mL of 1,2-dichloroethane were added, anhydrous aluminum trichloride (2.318 g, 17.5 mmol) was added, first stirred for 30 min at room temperature, temperature was then lowered to 0° C., 1.5 g of INT 2 was added dropwise, first stirred for 30 min at low temperature, temperature was then raised to 50° C., reacted for 2 hours, monitored with dot plate. Temperature was lowered, poured into ice water, dichloromethane was added to extract twice, dried, spin-dried, passed through a chromatographic column to obtain 1.24 g of product. $^1$HNMR (400 MHz, $CDCl_3$) δ 8.84 (s, 1H), 8.05-8.00 (m, 1H), 7.96 (s, 1H), 7.42-7.26 (m, 3H), 2.50 (s, 3H).

Synthesis of Example 3: INT 6 (50 mg, 0.11 mmol), Compound 4 (35 mg, 0.11 mmol), p-toluenesulfonic acid (31 mg, 0.17 mmol), 1 mL of NMP, and 2 mL of ethylene glycol monomethyl ether were added to a 5 mL reactor, heated to 120° C., reacted for 6 h, cooled to room temperature, 10 mL of ethyl acetate was added, washed with an aqueous sodium bicarbonate solution, washed with saturated brine once, dried, spin-dried, purified to obtain 5 mg of product. MS+1: 651.50.

Example 4

The structural formula of the compound used as the kinase inhibitor of the example is:

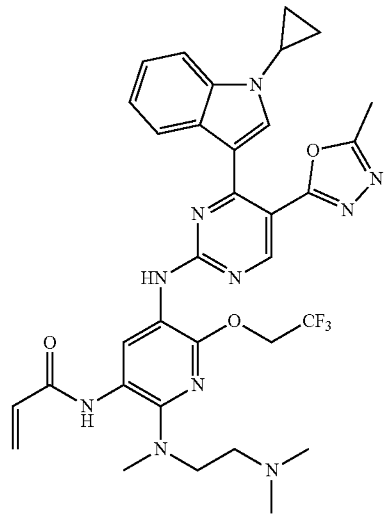 [SMILES: C=CC(=O)Nc1cc(Nc2ncc(-c3nnc(C)o3)c(-c3cn(C4CC4)c4ccccc34)n2)c(OCC(F)(F)F)nc1N(C)CCN(C)C]

Synthetic Route:

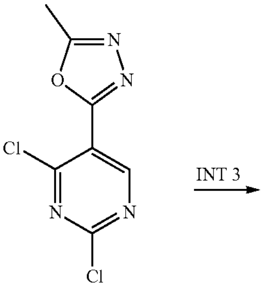

1

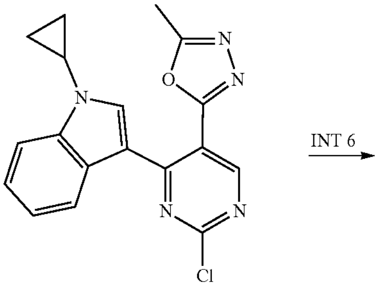

2

-continued

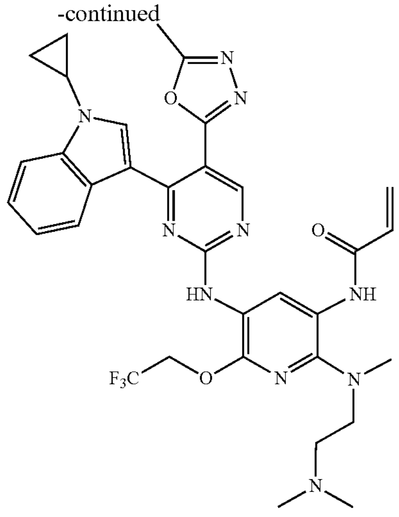

Example 4

Synthesis of Compound 2: in a 250 ml single-necked flask, Compound 3 (2.38 g, 10.3 mmol), 120 mL of 1,2-dichloroethane, anhydrous aluminum trichloride (2.33 g, 17.5 mmol) were added, stirred for 30 min at room temperature, temperature was then lowered to 0° C., 1.62 g of INT 3 was added dropwise, stirred for 30 min at low temperature, temperature was then raised to 50° C., reacted for 2 hours, temperature was lowered, poured into ice water, dichloromethane was added to extract twice, dried, spin-dried, passed through a chromatographic column to obtain 1.5 g of product.

Synthesis of Example 4: INT 6 (50 mg, 0.11 mmol), Compound 2 (39 mg, 0.11 mmol), p-toluenesulfonic acid monohydrate (35.5 mg, 0.187 mmol), 1 mL of NMP, and 2 mL of ethylene glycol monomethyl ether were added to a 5 mL reactor, heated to 120° C., reacted for 6 h, cooled to room temperature, 10 mL of ethyl acetate was added, washed with an aqueous sodium bicarbonate solution, washed with saturated brine once, dried, purified to obtain 5 mg of product. MS+1: 677.50.

Example 5

The structural formula of the compound used as the kinase inhibitor of the example is:

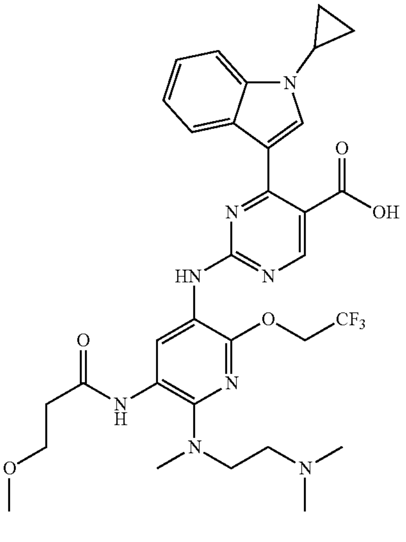 [SMILES: COCCC(=O)Nc1cc(Nc2ncc(C(=O)O)c(-c3cn(C4CC4)c4ccccc34)n2)c(OCC(F)(F)F)nc1N(C)CCN(C)C]

Synthetic Route:

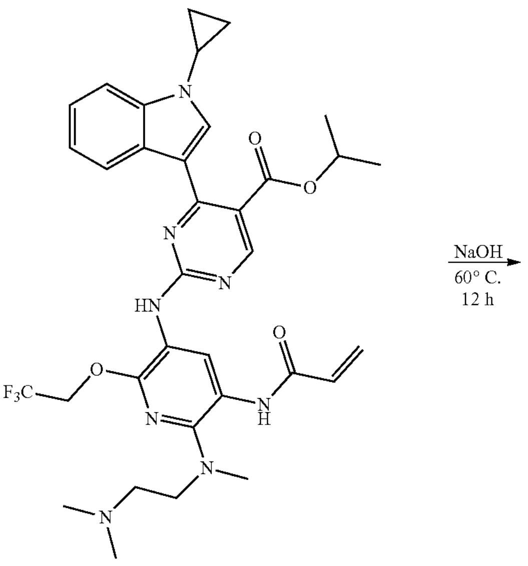

Example 1

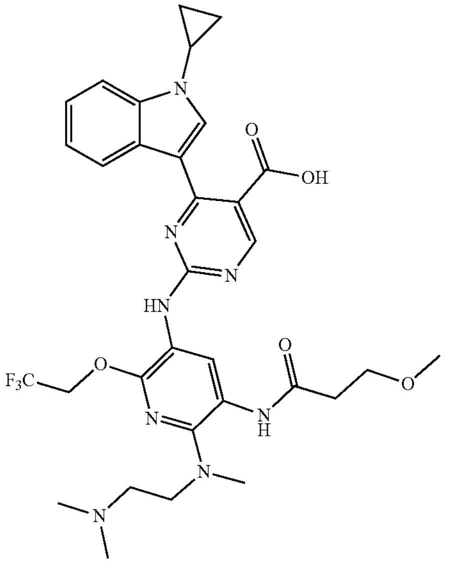

Example 5

Synthesis of Example 5: the compound of Example 1 (50 mg, 0.073 mmol), NaOH (5.3 mg, 0.13 mmol), 2 mL of methanol were added to a 5 mL reactor, heated to 70° C., reacted for 6 h, cooled to room temperature, 10 mL of ethyl acetate was added, washed with an aqueous sodium bicarbonate solution, washed with saturated brine once, dried, purified to obtain 5 mg of product. MS+1: 671.51.

Example 6 and Example 7

The structural formula of the compound used as the kinase inhibitor of Examples 6 and 7 is:

Example 6
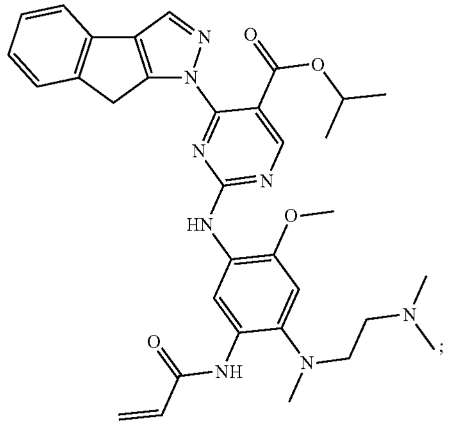 [SMILES: C=CC(=O)Nc1cc(Nc2ncc(C(=O)OC(C)C)c(-n3ncc4c3Cc3ccccc3-4)n2)c(OC)cc1N(C)CCN(C)C]
Example 7
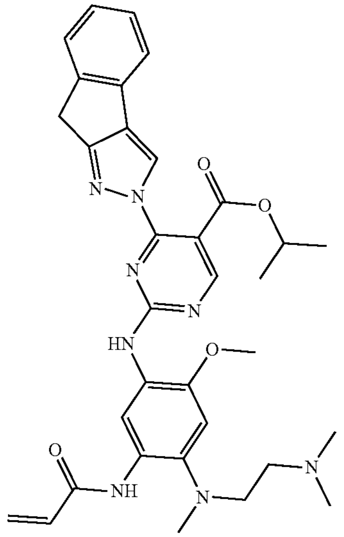 [SMILES: C=CC(=O)Nc1cc(Nc2ncc(C(=O)OC(C)C)c(-n3cc4c(n3)Cc3ccccc3-4)n2)c(OC)cc1N(C)CCN(C)C]
Synthetic Route:
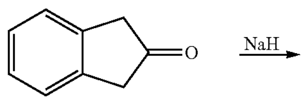
1
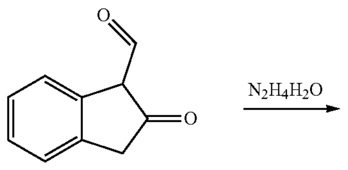
2
-continued
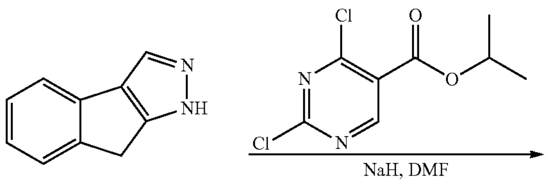
3
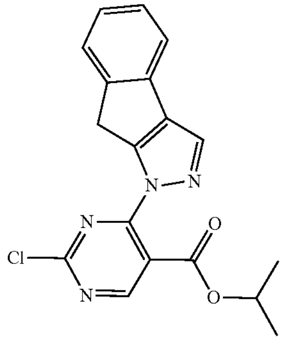
+
4
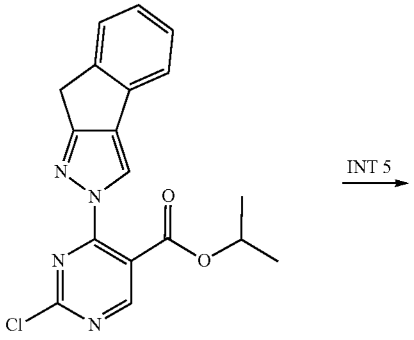
5
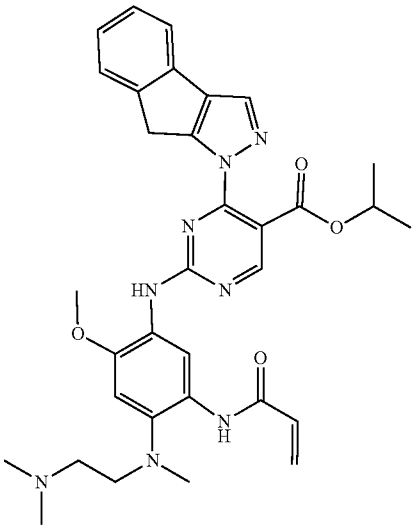
+
Example 6

-continued

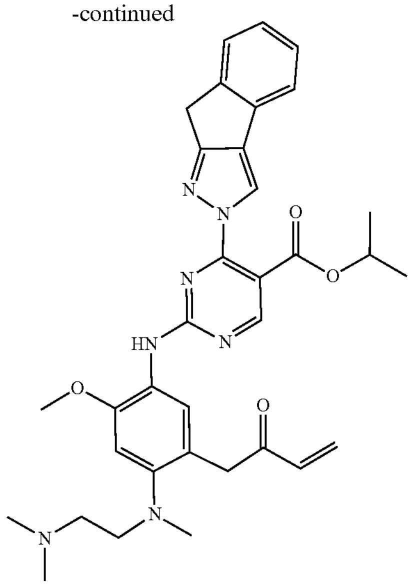

Example 7

Synthesis of Compound 2: in a 50 mL three-necked flask, sodium hydride (0.55 g, 13.75 mmol, 60%), 20 mL of toluene were respectively added, at 0° C., under nitrogen protection, ethyl formate (1.1 g, 14.86 mmol) was slowly added dropwise, after adding, stirred for 10 minutes at 0° C., a toluene (10 mL) solution of 2-indanone (1.5 g, 11.36 mmol) was continued to be added dropwise, temperature was raised to room temperature after adding, stirred overnight. The next day, diluted with water, adjusted to pH=4 with concentrated hydrochloric acid, the aqueous phase was extracted with ethyl acetate three times, the organic phase was combined, washed with water, dried, spin-dried to obtain 3.5 g of crude product.

Synthesis of Compound 3: in a 50 mL three-necked flask, 3.5 g of crude product of Compound 2, hydrazine hydrate (1.8 g, 27.95 mmol), glacial acetic acid (1.61 g, 26.81 mmol), 30 mL of ethanol were respectively added, heating reacted for 3 h at 85° C. under nitrogen protection. Concentrated, diluted with water, extracted with ethyl acetate three times, washed with water, dried, passed through a chromatographic column to obtain 1.35 g of product.

Synthesis of Compound 4 and Compound 5: Compound 3 (156 mg, 1 mmol), 5 mL of N,N-dimethylformamide were respectively added to a 10 mL reactor, under nitrogen protection, sodium hydride was added at 0° C., after adding, stirred for 0.5 h, 2,4-dichloropyrimidine-5-carboxylic acid isopropyl ester (280 mg, 1.2 mmol) was continued to be added dropwise, temperature was raised to room temperature after adding, stirred overnight. The next day, water was added to quench, the aqueous phase was extracted with ethyl acetate three times, the organic phase was combined, washed with water, dried, passed through a chromatographic column to obtain a total of 85 mg of Compound 4 and Compound 5.

Synthesis of Example 6 and Example 7: Compound 4 (50 mg, 0.14 mmol), Compound 5 (50 mg, 0.14 mmol), INT 5 (82 mg, 0.28 mmol), p-toluenesulfonic acid monohydrate (26.8 mg, 0.14 mmol), DCE (5 mL), n-pentanol (5 mL) were respectively added to a 10 mL reactor, temperature was raised to 95° C. under nitrogen protection, stirred overnight. The next day, water was added to quench, the aqueous phase was extracted with dichloromethane three times, the organic phase was combined, concentrated, passed through a column, then purified to obtain 5 mg of Example 6 and 9 mg of Example 7. Example 6: $^{1}$HNMR (400 MHZ, $CDCl_3$) δ 13.20 (s, 1H), 9.78 (s, 1H), 9.33 (s, 1H), 9.11 (s, 1H), 8.55 (s, 1H), 8.11 (s, 1H), 7.63 (d, J=4 Hz, 1H), 7.46 (d, J=2 Hz, 1H), 7.31 (dd, J=8 Hz, 1H), 7.06-6.99 (m, 1H), 6.71 (s, 1H), 6.62 (d, J=8 Hz, 1H), 5.82 (d, J=6 Hz, 1H), 5.29-5.25 (m, 1H), 3.89 (s, 3H), 3.79 (s, 2H), 3.28 (s, 2H), 3.17 (s, 2H), 2.83 (s, 6H), 2.65 (s, 3H), 1.30 (d, J=2 Hz, 1H). Example 7: $^{1}$HNMR (400 MHZ, $CDCl_3$) δ 12.98 (s, 1H), 11.10 (s, 1H), 9.85 (s, 1H), 9.44-9.34 (m, 1H), 9.11 (s, 1H), 7.64 (s, 1H), 7.46 (s, 1H), 6.99-6.96 (m, 1H), 6.76 (s, 1H), 6.59 (d, J=8 Hz, 1H), 5.82 (d, J=4 Hz, 1H), 5.34-5.33 (m, 1H), 4.58 (s, 2H), 3.97 (s, 3H), 3.89-3.88 (m, 2H), 3.31 (s, 2H), 3.20 (s, 2H), 2.86 (s, 7H), 2.67 (s, 3H), 1.42 (s, 6H).

Example 8

The structural formula of the compound used as the kinase inhibitor of the example is:

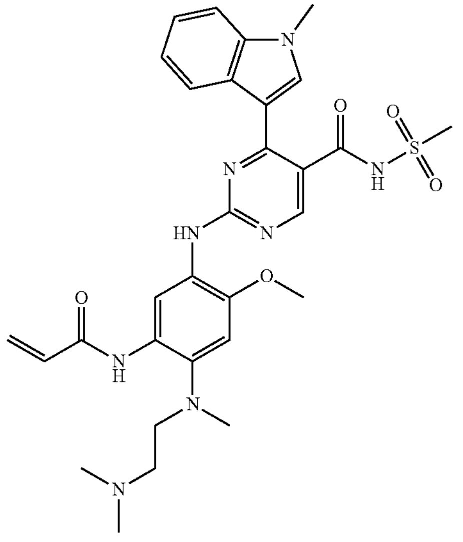 [SMILES: C=CC(=O)Nc1cc(Nc2ncc(C(=O)NS(C)(=O)=O)c(-c3cn(C)c4ccccc34)n2)c(OC)cc1N(C)CCN(C)C]

Synthetic Route:

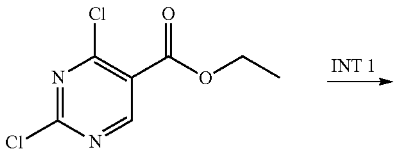

1

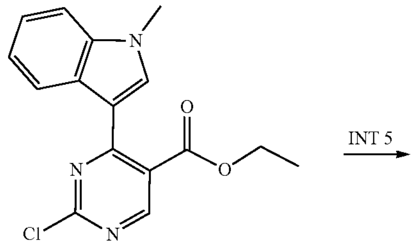

2

-continued

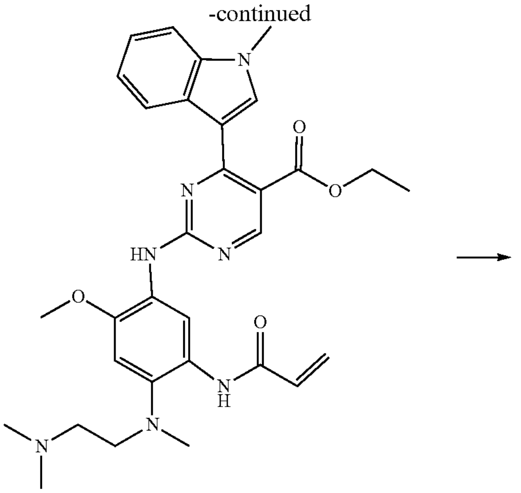

3

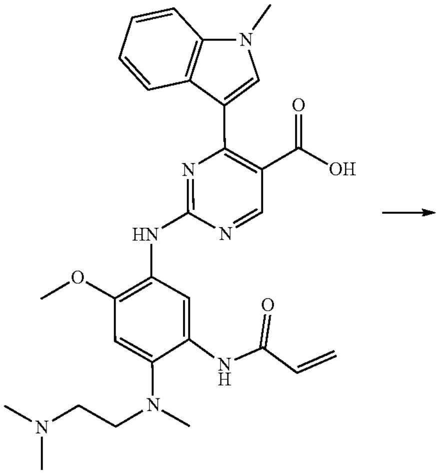

4

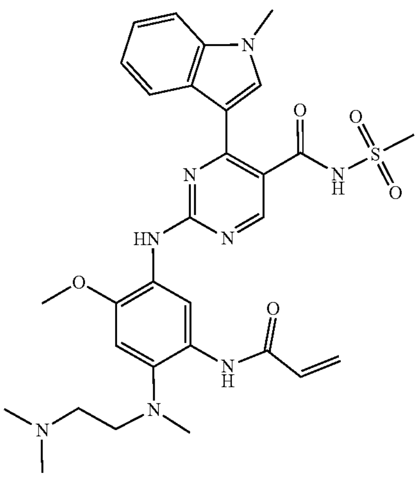

Example 8

Synthesis of Compound 2: in a 100 mL single-necked flask, Compound 1 (0.94 g, 4.3 mmol) and 20 mL of 1,2-dichloroethane were respectively added, in an ice bath, aluminum trichloride (1.06 g, 8 mmol) was added, stirred for 5 minutes, INT1 (0.52 g, 4 mmol) was then added, then heating reacted for 1.5 h at 50° C. Water was added after reacting, extracted with dichloromethane three times, the organic phase was combined, washed with water, dried, passed through a chromatographic column to obtain 0.6 g of product. $^1$HNMR (400 MHZ, $CDCl_3$) δ 8.81 (s, 1H), 8.16 (t, J=4 Hz, 1H), 7.96 (s, 1H), 7.38-7.36 (m, 1H), 7.33-7.29 (m, 2H), 4.35-4.30 (m, 2H), 3.87 (s, 1H), 1.24 (t, J=8 Hz, 3H).

Synthesis of Compound 3: in a 50 mL single-necked flask, Compound 2 (0.6 g, 1.904 mmol), INT 5 (0.50 g, 1.713 mmol), p-toluenesulfonic acid monohydrate (0.361 g, 1.904 mmol), 5 mL of 1,2-dichloroethane, and 5 mL of 1-pentanol were respectively added, heated to 70° C., reacted for 36 h. After reacting, the reaction solution was evaporated to dryness, dichloromethane was added to dissolve, washed with water, dried, passed through a chromatographic column to obtain 0.6 g of product. $^1$HNMR (400 MHZ, $CDCl_3$) δ 9.75 (s, 1H), 8.90 (s, 1H), 8.65 (s, 1H), 7.89 (s, 1H), 7.52 (s, 1H), 7.32 (d, J=4 Hz, 1H), 7.20 (t, J=8 Hz, 1H), 7.12 (t, J=8 Hz, 1H), 3.75 (s, 1H), 6.46 (d, J=8 Hz, 1H), 5.70 (d, J=8 Hz, 1H), 3.93 (s, 1H), 3.87 (s, 1H), 2.99 (s, 2H), 2.70 (s, 3H), 2.41 (s, 7H), 0.93 (t, J=4 Hz, 3H).

Synthesis of Compound 4: in a 100 mL single-necked flask, Compound 3 (0.4 g, 0.70 mmol), sodium hydroxide (0.084 g, 2.1 mmol), 10 mL of water, and 10 mL of tetrahydrofuran were respectively added, stirred for 30 h at room temperature. After reacting, the reaction solution was spin-dried, water was then added to dissolve, insoluble was filtered out, the pH of the water phase was adjusted to about 5 with 1N of dilute hydrochloric acid, the water phase was spin-dried to obtain 0.4 g of crude product.

Synthesis of Example 8: in a 50 mL single-necked flask, Compound 4 (0.2 g, 0.368 mmol), methanesulfonamide (0.106 g, 1.1 mmol), 2-chloro-1-picoline pyridinium iodonium (0.112 g, 0.44 mmol), triethylamine (0.112 g, 1.1 mmol), DMAP (2.24 mg, 0.002 mmol), and 5 mL of N,N-dimethylformamide were added, stirred for 36 h at room temperature. After reacting, saturated brine was added, extracted with dichloromethane three times, washed with water, dried, purified to obtain 34 mg of product. MS+1: 621.48.

Example 9

The structural formula of the compound used as the kinase inhibitor of the example is:

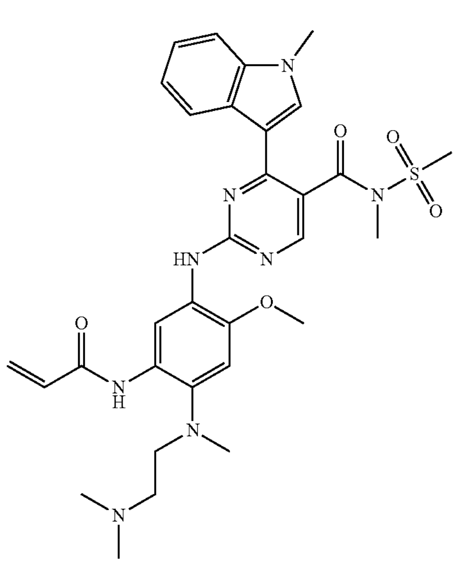 [SMILES: C=CC(=O)Nc1cc(Nc2ncc(C(=O)N(C)S(C)(=O)=O)c(-c3cn(C)c4ccccc34)n2)c(OC)cc1N(C)CCN(C)C]

Synthetic Route:

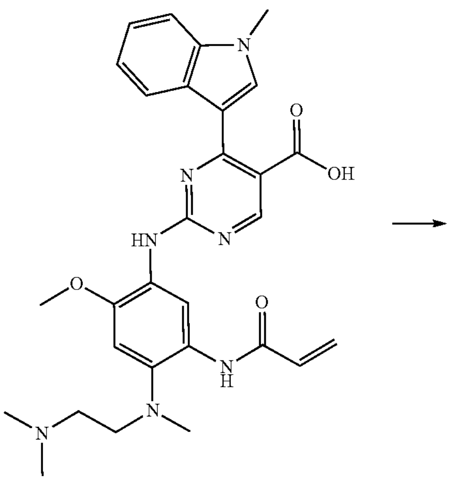

1

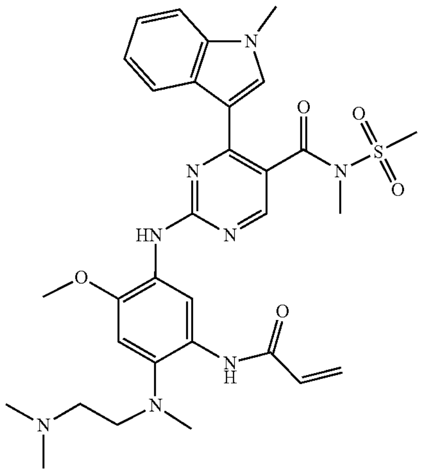

Example 9

Synthesis of Example 9: in a 50 mL single-necked flask, Compound 1 (0.2 g, 0.368 mmol), methanesulfonyl methylamide (0.12 g, 1.1 mmol), 2-chloro-1-picoline pyridinium iodonium (0.112 g, 0.44 mmol), triethylamine (0.112 g, 1.1 mmol), DMAP (2.24 mg, 0.002 mmol), and 5 mL of N,N-dimethylformamide were respectively added, stir-reacted for 24 h at room temperature. After reacting, saturated brine was added, extracted with dichloromethane three times, washed with water, dried, purified to obtain 20 mg of product. MS+1: 635.48.

Example 10

The structural formula of the compound used as the kinase inhibitor of the example is:

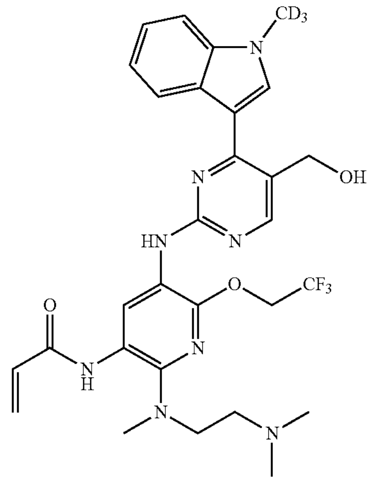 [SMILES: [2H]C([2H])([2H])n1cc(-c2nc(Nc3cc(NC(=O)C=C)c(N(C)CCN(C)C)nc3OCC(F)(F)F)ncc2CO)c2ccccc21]

Synthetic Route:

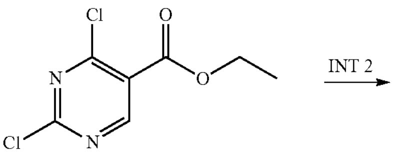

1

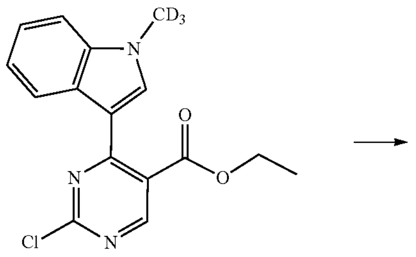

2

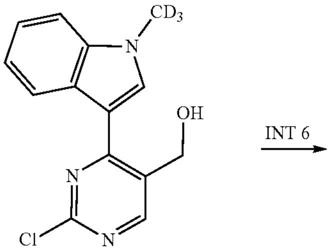

3

-continued

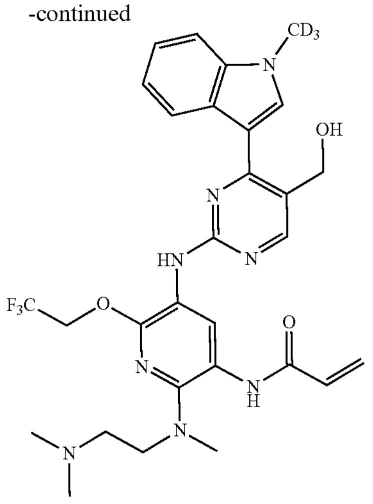

Example 10

Synthesis of Compound 2: in a 100 mL single-necked flask, Compound 1 (1.85 g, 8.4 mmol) and 40 mL of 1,2-dichloroethane were respectively added, in an ice bath, aluminum trichloride (2.13 g, 16 mmol) was added, stirred for 5 minutes, INT 2 (1.2 g, 9 mmol) was then added, then heating reacted for 1.5 h at 50° C. After reacting, ice water was added, extracted with dichloromethane three times, washed with water, dried, passed through a chromatographic column to obtain 1.3 g of product.

Synthesis of Compound 3: in a 50 mL three-necked flask, Compound 2 (100 mg, 0.32 mmol) and tetrahydrofuran (8 mL) were added, temperature was lowered to 0° C., under nitrogen protection, lithium tetrahydroaluminum (24 mg, 0.631 mmol) was added, then stirred overnight. The next day, temperature was lowered, a saturated aqueous ammonium chloride solution was added dropwise to quench, extracted with ethyl acetate three times. Dried, spin-dried, passed through a chromatographic column to obtain 40 mg of product. $^1$HNMR: ($CDCl_3$, 400 MHz) δ 8.57-8.50 (m, 1H), 8.03 (s, 1H), 7.37-7.33 (m, 3H), 4.77 (d, J=2.4 Hz, 2H).

Synthesis of Example 10: in a 10 mL single-necked flask, Compound 3 (32 mg, 0.12 mmol), INT6 (64.5 mg, 0.14 mmol), $Pd_2dba_3$ (14.8 mg, 0.016 mmol), X-Phos (18.4 mg, 0.032 mmol), potassium phosphate (56 mg, 0.3 mmol), dioxane (3.2 mL) were sequentially added. Under nitrogen protection, heated to 100° C., stir-reacted for 12 h. After reacting, water and ethyl acetate were added, extracted three times, the organic phase was combined, dried, spin-dried, purified to obtain 10 mg of product. $^1$HNMR: ($CD_3OD$, 400 MHz) δ 8.49 (s, 1H), 8.34 (s, 1H), 8.26-8.23 (m, 2H), 7.50 (d, J=8.0 Hz, 1H), 7.27-7.23 (m, 1H), 7.10-7.06 (m, 1H), 6.50-6.35 (m, 2H), 5.88-5.85 (m, 1H), 4.97-4.85 (m, 2H), 4.69 (s, 2H), 3.84-3.81 (m, 2H), 3.36-3.31 (m, 2H), 3.91 (s, 6H), 2.84 (s, 3H).

Example 11

The structural formula of the compound used as the kinase inhibitor of the example is:

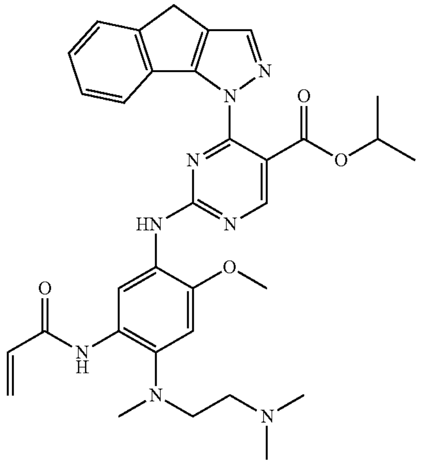 [SMILES: C=CC(=O)Nc1cc(Nc2ncc(C(=O)OC(C)C)c(-n3ncc4c3-c3ccccc3C4)n2)c(OC)cc1N(C)CCN(C)C]

Synthetic Route:

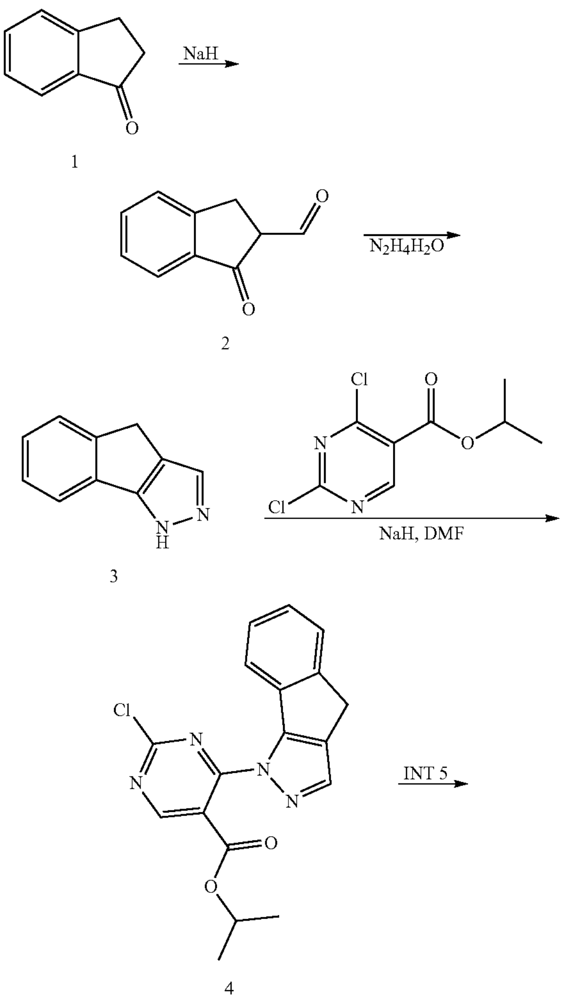

-continued

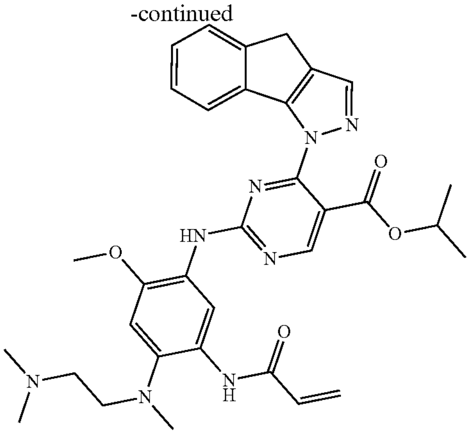

Example 11

Synthesis of Compound 2: in a 250 mL three-necked flask, NaH (5.7 g, 142.4 mmol) and toluene (50 mL) were added, cooled to an internal temperature of about 5° C. in an ice bath, ethyl formate (10.54 g, 142.4 mmol) was added, the reaction solution was cooled to about 2° C. after adding, 50 mL of a toluene solution of Compound 1 (9.4 g, 71.2 mmol) was added dropwise, while controlling the internal temperature to be between 0-4° C., dropwise addition was completed in about 30 minutes, the ice bath was removed after the dropwise addition of the reaction solution, temperature was naturally raised to room temperature, stir-reacted overnight. The next day, a large amount of solid was precipitated, 70 mL of water was added thereto, adjusted to pH=1 to 2 with concentrated hydrochloric acid, extracted with ethyl acetate twice, dried, concentrated to obtain 13.64 g of crude product.

Synthesis of Compound 3: 13.64 g of the crude product in the previous step was taken, 100 mL of ethanol, 80% hydrazine hydrate (11.83 g, 175.2 mmol), and glacial acetic acid (10.1 g, 168 mmol) were added, the mixture was reflux-reacted for 3 h, the solvent was evaporated to dryness under reduced pressure, 80 mL of ethyl acetate and 60 mL of water were added to the residue, extracted with ethyl acetate twice, the organic phase was combined, dried, concentrated, pulped to obtain 9.1 g of product. $^{1}$HNMR: ($CDCl_3$, 400 MHz) δ 7.80-7.78 (d, J=7.6 Hz, 1H), 7.51-7.48 (m, 2H), 7.38-7.34 (m, 1H), 7.31-7.27 (m, 1H), 3.67 (s, 2H).

Synthesis of Compound 4: in a 100 mL single-necked flask, Compound 3 (200 mg, 1.28 mmol) and 6 mL of DMF were added, under nitrogen protection, cooled to about 5° C. in an ice bath, NaH (61.5 mg, 1.54 mmol) was added, a small amount of air bubbles escaped, after adding, the reaction solution was stir-reacted for 20 minutes in the ice bath, 2 mL of a DMF solution of 2,4-dichloropyrimidine-5-carboxylate isopropyl ester (330 mg, 1.41 mmol) was then added, the reaction solution was reddish brown after adding, temperature was raised to room temperature, stirred overnight. The next day, water and ethyl acetate were added, liquid was separated, the aqueous phase was extracted with ethyl acetate twice again, the organic phase was combined, dried, concentrated, passed through a chromatographic column to obtain 138 mg of product. $^{1}$HNMR: ($CDCl_3$, 400 MHz) δ 9.06 (s, 1H), 8.35 (s, 1H), 7.94 (d, J=7.6 Hz, 1H), 7.41 (d, J=7.2 Hz, 1H), 7.36-7.28 (m, 2H), 5.29-5.23 (m, 1H), 3.68 (s, 2H), 1.38 (d, J=6.4 Hz, 6H).

Synthesis of Example 11: in a 25 mL single-necked flask, Compound 4 (138 g, 0.39 mmol) and INT 5 (113.8 mg, 0.39 mmol) were added, p-toluenesulfonic acid monohydrate (74.1 mg, 0.39 mmol), n-pentanol (5.5 mL), and 1,2-dichloroethane (5.5 mL) were then added, the mixture was heated in an oil bath at 90° C., stirred overnight, the next day, water and dichloromethane were added, the liquid was separated, the aqueous phase was extracted with dichloromethane twice, the organic phase was combined, dried, concentrated, passed through a chromatographic column to obtain 108 mg of relatively pure crude product, then purified to obtain 43 mg of pure product. $^{1}$HNMR: ($CDCl_3$, 400 MHz) δ 11.14 (s, 1H), 9.68 (s, 1H), 9.20-9.0 (m, 3H), 7.93 (s, 1H), 7.49 (s, 1H), 7.37-7.34 (m, 2H), 6.98-6.91 (m, 1H), 6.72 (s, 1H), 6.55-6.51 (m, 1H), 5.83-5.80 (m, 1H), 5.37-5.32 (m, 1H), 3.91 (s, 3H), 3.73 (s, 2H), 3.32-3.30 (m, 2H), 3.27-3.26 (m, 2H), 2.89 (s, 1H), 2.67 (s, 3H), 1.44 (d, J=6 Hz, 6H).

Example 12

The structural formula of the compound used as the kinase inhibitor of the example is:

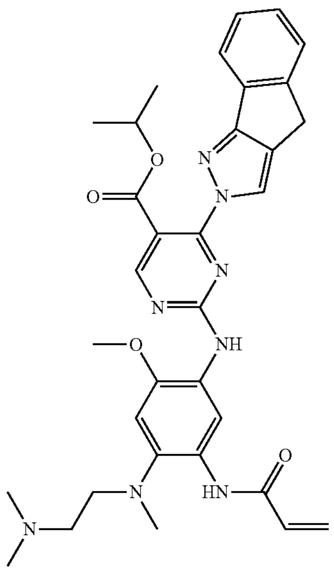 [SMILES: C=CC(=O)Nc1cc(Nc2ncc(C(=O)OC(C)C)c(-n3cc4c(n3)-c3ccccc3C4)n2)c(OC)cc1N(C)CCN(C)C]

Synthetic Route:

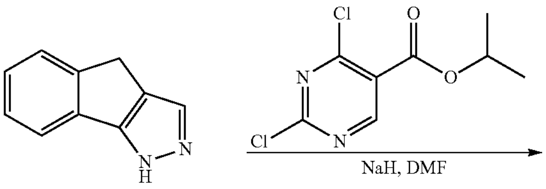

1

-continued

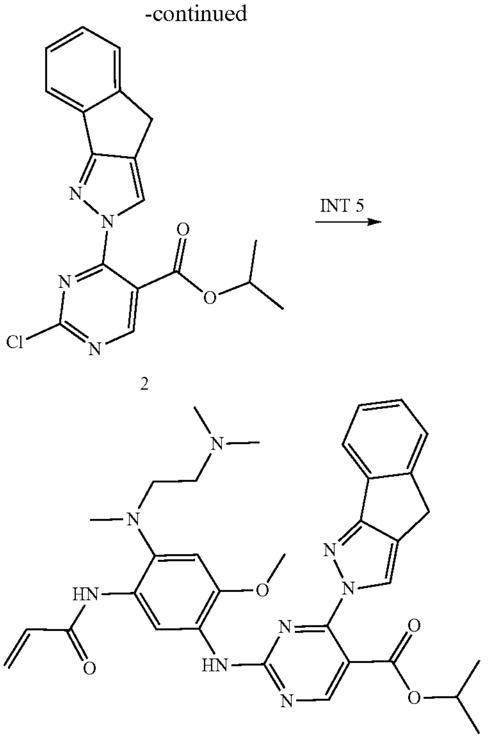

2

Example 12

Synthesis of Compound 2: in a 100 mL single-necked flask, Compound 1 (200 mg, 1.28 mmol) and 6 mL of DMF were added, cooled to an internal temperature of about 5° C. in an ice bath under nitrogen protection, NaH (61.5 mg, 1.54 mmol) was added, a small amount of air bubbles escaped, the reaction solution was stir-reacted for 20 minutes in the ice bath after adding, 2 mL of a DMF solution of 2,4-dichloropyrimidine-5-carboxylate isopropyl ester (330 mg, 1.41 mmol) was then added thereto with a syringe, the reaction solution was reddish brown after adding, the ice bath was not removed and allowed to naturally rise to room temperature, stirred overnight, water and ethyl acetate were added to the reaction solution, the liquid was separated after stirring, the aqueous phase was extracted with ethyl acetate twice, the organic phase was combined, dried, concentrated, passed through a chromatographic column to obtain 2108 mg of compound. $^1$HNMR: ($CDCl_3$, 400 MHz) δ 8.59 (s, 1H), 8.34 (s, 1H), 7.71-7.69 (m, 1H), 7.49-7.47 (m, 1H), 7.39-7.35 (m, 2H), 5.40-5.33 (m, 1H), 3.74 (s, 2H), 1.40 (d, J=6.8 Hz, 6H).

Synthesis of Example 12: in a 25 mL single-necked flask, Compound 2 (108 g, 0.31 mmol) and INT 5 (89.1 mg, 0.31 mmol) were added, p-toluenesulfonic acid monohydrate (57.9 mg, 0.31 mmol) 4.3 mL of n-pentanol, and 4.3 mL of 1,2-dichloroethane were then added, the mixture was heated in an oil bath at 90° C., stir-reacted overnight, dichloromethane was added to the residue, stirred, the liquid was separated, the aqueous phase was extracted with dichloromethane twice, the organic phase was combined, dried, concentrated, passed through a chromatographic column to obtain 25 mg of relatively pure crude product, the crude product was then purified to obtain 9 mg of pure product. $^1$HNMR: ($CDCl_3$, 400 MHz) δ 12.43 (s, 1H), 9.48 (s, 1H), 9.11-9.02 (m, 3H), 8.48 (s, 1H), 7.72 (d, J=4.8 Hz, 1H), 7.51 (d, J=4.8 Hz, 1H), 7.38-7.36 (m, 2H), 6.97-6.91 (m, 1H), 6.72 (s, 1H), 6.54-6.50 (m, 1H), 5.80 (d, J=9.6 Hz, 1H), 5.30-5.29 (m, 1H), 3.89 (s, 3H), 3.78 (s, 2H), 3.30 (s, 2H), 3.20 (s, 2H), 2.85 (s, 6H), 2.65 (s, 3H), 1.34 (d, J=6.4 Hz, 6H).

Example 13

The structural formula of the compound used as the kinase inhibitor of the example is:

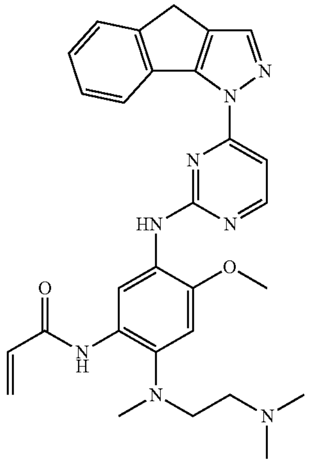 [SMILES: C=CC(=O)Nc1cc(Nc2nccc(-n3ncc4c3-c3ccccc3C4)n2)c(OC)cc1N(C)CCN(C)C]

Synthetic Route:

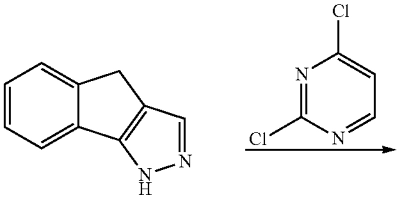

1

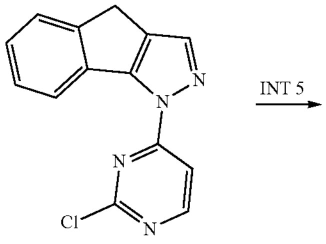

2

-continued

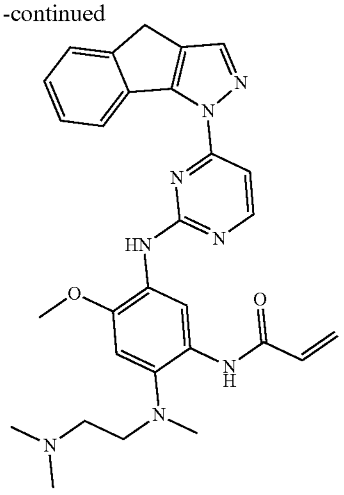

Example 13

Synthesis of Compound 2: in a 100 mL single-necked flask, Compound 1 (200 mg, 1.28 mmol) and 6 mL of DMF were added, under nitrogen protection, stirred and cooled in an ice bath to an internal temperature of about 5° C., NaH (61.5 mg, 1.54 mmol) was added, a small amount of air bubbles escaped, the reaction solution was stir-reacted for 20 minutes in the ice bath after adding, 2 mL of a DMF solution of 2,4-dichloropyrimidine (210 mg, 1.41 mmol) was then added with a syringe, the reaction liquid was reddish brown after adding, the ice bath was not removed and allowed to naturally rise to room temperature, stirred overnight, water and ethyl acetate were added to the reaction solution, the liquid was separated, extracted with ethyl acetate twice, the organic phase was combined, dried, concentrated, passed through a chromatographic column to obtain 83 mg of product.

Synthesis of Example 13: Compound 2 (50 mg, 0.19 mmol) and INT 5 (54.4 mg, 0.19 mmol) were added to a reaction flask, p-toluenesulfonic acid monohydrate (35.5 mg, 0.19 mmol), 2 mL of n-pentanol, and 2 mL of 1,2-dichloroethane were then added, the mixture was heated in an oil bath at 90° C., stir-reacted overnight. The next day, water and dichloromethane were added, the liquid was separated, extracted with dichloromethane twice, the organic phase was combined, dried, concentrated, passed through a chromatographic column to obtain 79 mg of product. $^1$HNMR: ($CDCl_3$, 400 MHz) δ 10.09 (s, 1H), 9.79 (s, 1H), 9.37 (s, 1H), 8.43 (d, J=5.2 Hz, 1H), 7.89 (d, J=7.2 Hz, 1H), 7.84 (s, 1H), 7.52 (d, J=7.6 Hz, 1H), 7.41-7.32 (m, 3H), 6.79 (s, 1H), 6.56-6.51 (m, 1H), 6.44-6.38 (m, 1H), 5.76-5.73 (m, 1H), 3.89 (s, 3H), 3.81 (s, 2H), 2.92-2.89 (m, 2H), 2.70 (s, 3H), 2.36-2.33 (m, 2H), 2.29 (s, 6H), 2.03 (d, J=3.6 Hz, 1H).

Example 14

The structural formula of the compound used as the kinase inhibitor of the example is:

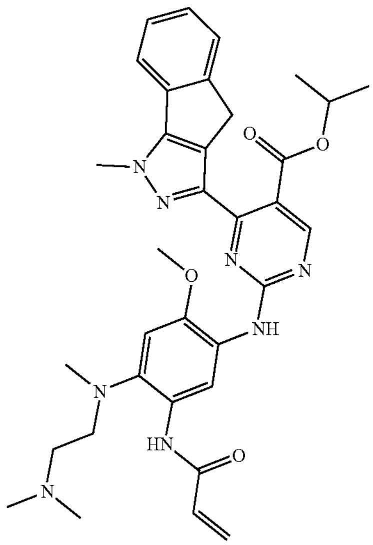 [SMILES: C=CC(=O)Nc1cc(Nc2ncc(C(=O)OC(C)C)c(-c3nn(C)c4c3Cc3ccccc3-4)n2)c(OC)cc1N(C)CCN(C)C]

Synthetic Route:

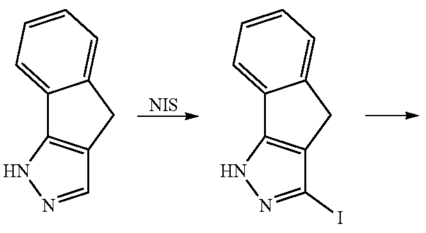

1

2

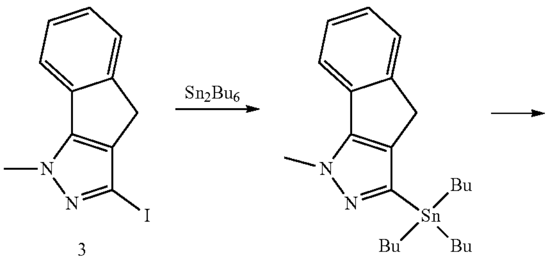

3

4

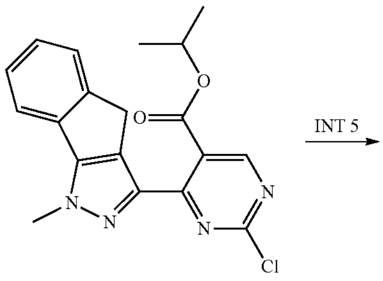

5

-continued

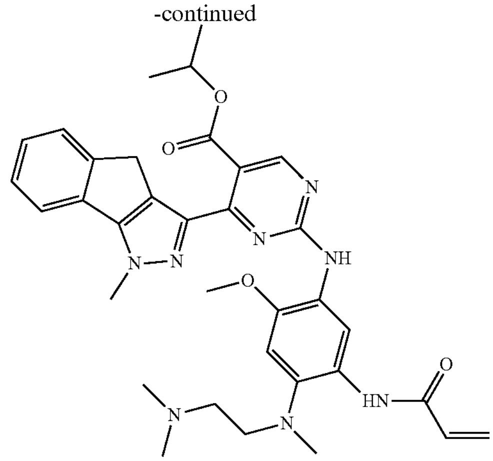

Example 14

Synthesis of Compound 2: Compound 1 (1 g, 6.40 mmol) was dissolved in 25 mL of DMF, NIS (1.73 g, 7.68 mmol) was then added, reacted overnight at 80° C., tracked with dot plate. The next day, the reaction ended, the reaction solution was cooled to room temperature, water and ethyl acetate were added for extraction, the organic phase was washed with saturated brine, dried, concentrated, passed through a chromatographic column to obtain 1.17 g of product. $^1$HNMR: (DMSO-d6, 400 MHz) δ 13.50 (s, 1H), 7.63-7.53 (m, 2H), 7.37-7.27 (m, 2H), 3.54 (s, 2H).

Synthesis of Compound 3: Compound 2 (600 mg, 2.13 mmol) was dissolved in anhydrous THF, the reaction temperature was lowered to 0-5° C., NaH (94 mg, 2.34 mmol) was added, reacted for 30 minutes at 0-5° C., iodomethane (5.54 mmol) was then added dropwise at 0-5° C., after the dropwise addition, temperature was slowly raised to room temperature, reacted overnight. The next day, the reaction ended, water was added to quench the reaction, extracted with ethyl acetate, the organic phase was washed with saturated brine, dried, concentrated, passed through a chromatographic column to obtain 279 mg of product. $^1$HNMR: (DMSO-d6, 400 MHz) δ 7.56 (d, J=7.6 Hz, 1H), 7.52-7.37 (m, 1H), 7.34-7.33 (m, 1H), 7.31-7.26 (m, 1H), 4.08 (s, 3H), 3.47 (s, 2H).

Synthesis of Compound 4: Compound 3 (109 mg, 0.37 mmol) was dissolved in 4 mL of dry 1,4-dioxane, hexa-n-butyl ditin (0.43 g, 0.74 mmol), tetrakis(triphenylphosphine) palladium (20.8 mg, 0.018 mmol) were added, reacted overnight at 100° C. The next day, 2 mL of 1N cesium fluoride aqueous solution was added, stirred for 5 min at room temperature, filtered, the filtrate was extracted with ethyl acetate, the organic phase was washed with saturated brine, dried, concentrated, passed through a chromatographic column to obtain 49 mg of product. $^1$HNMR: ($CDCl_3$, 400 MHz) δ 7.54-7.48 (m, 2H), 7.35-7.29 (m, 1H), 7.25-7.21 (m, 1H), 4.17 (s, 3H), 3.53 (s, 2H), 1.67-1.53 (m, 10H), 1.40-1.36 (m, 7H), 1.34-1.16 (m, 6H), 1.14-1.13 (m, 5H), 1.11-0.93 (m, 11H).

Synthesis of Compound 5: Compound 4 (50 mg, 0.11 mmol) was dissolved in 2 mL of anhydrous 1,4-dioxane, 2,4-dichloropyrimidine-5-carboxylate isopropyl ester (35 mg, 0.15 mmol), tris(dibenzylideneacetone)dipalladium (41 mg, 0.045 mmol) were added, reacted for 3.5 h at 80° C., after reacting, water and ethyl acetate were added for extraction, the organic phase was washed with saturated brine, dried, concentrated, passed through a chromatographic column to obtain 25 mg of product. $^1$HNMR: ($CDCl_3$, 400 MHz) δ 8.63 (s, 1H), 7.59-7.56 (m, 2H), 7.39-7.30 (m, 2H), 5.38-5.29 (m, 1H), 4.17 (s, 3H), 3.89 (s, 2H), 1.39 (d, J=6.4 Hz, 6H).

Synthesis of Example 14: Compound 5 (25 mg, 0.068 mol) was dissolved in 1 mL of 1,2-dichloroethane and 1 mL of n-pentanol, INT 5 (20 mg, 0.068 mmol), p-toluenesulfonic acid monohydrate (13 mg, 0.068 mmol) were added, reacted overnight at 90° C., after reacting, the reaction solution was concentrated, a saturated aqueous sodium bicarbonate solution was added to wash, extracted with dichloromethane, the organic phase was washed with saturated brine, dried, concentrated, passed through a chromatographic column to obtain 21 mg of product. $^1$HNMR: ($CDCl_3$, 400 MHz) δ 8.64 (s, 1H), 8.42 (s, 1H), 7.71 (d, J=7.6 Hz, 1H), 7.56 (d, J=7.6 Hz, 1H), 7.40 (t, J=7.2 Hz, 1H), 7.30 (t, J=8.4 Hz, 1H), 6.97 (s, 1H), 6.49-6.47 (m, 2H), 5.84 (dd, J=3.6, 7.6 Hz, 1H), 5.20-5.14 (m, 1H), 4.17 (s, 3H), 4.01 (s, 3H), 3.73 (s, 2H), 3.51-3.48 (m, 2H), 3.28-3.25 (m, 2H), 2.86 (s, 6H), 2.72 (s, 3H), 1.28 (d, J=6.4 Hz, 6H).

Example 15

The structural formula of the compound used as the kinase inhibitor of the example is:

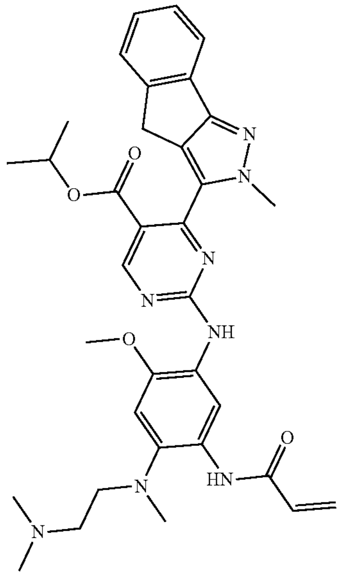 [SMILES: C=CC(=O)Nc1cc(Nc2ncc(C(=O)OC(C)C)c(-c3c4c(nn3C)-c3ccccc3C4)n2)c(OC)cc1N(C)CCN(C)C]

Synthetic Route:

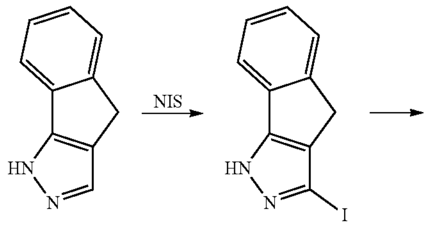

1 2

-continued

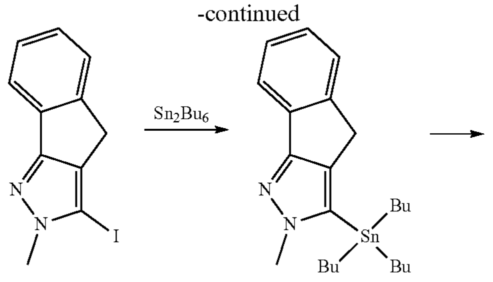

3 4

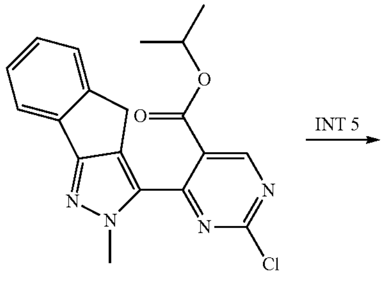

5

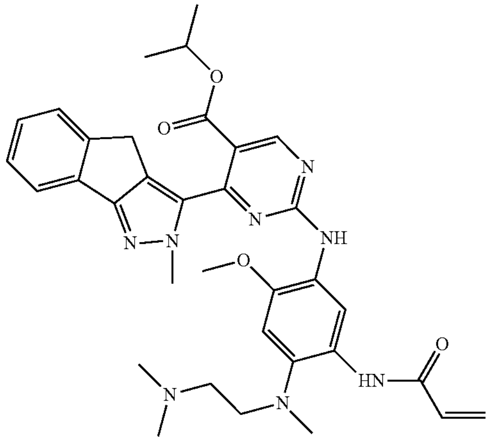

Example 15

Synthesis of Compound 2: Compound 1 (1 g, 6.40 mmol) was dissolved in 25 mL of DMF, NIS (1.73 g, 7.68 mmol) was then added, reacted overnight at 80° C., tracked with dot plate. The next day, the reaction ended, the reaction solution was cooled to room temperature, water and ethyl acetate were added for extraction, the organic phase was washed with saturated brine, dried, concentrated, passed through a chromatographic column to obtain 1.17 g of product. $^1$HNMR: (DMSO-d6, 400 MHz) δ 13.50 (s, 1H), 7.63-7.53 (m, 2H), 7.37-7.27 (m, 2H), 3.54 (s, 2H).

Synthesis of Compound 3: Compound 2 (3.18 g, 11.3 mmol) was dissolved in 50 mL of anhydrous THF, the reaction temperature was lowered to 0-5° C., NaH (0.5 g, 12.4 mmol) was added, reacted for 30 min at 0-5° C., methyl iodide (4.2 g, 29.3 mmol) was then added dropwise at 0-5° C., temperature was slowly raised to room temperature, reacted overnight. The next day, water was added to quench the reaction, extracted with ethyl acetate, the organic phase was washed with saturated brine, dried, concentrated, passed through a chromatographic column to obtain 195 mg of product. $^1$HNMR: (DMSO-d6, 400 MHz) δ 7.60 (d, J=7.2 Hz, 1H), 7.54 (d, J=7.2 Hz, 1H), 7.35 (t, J=7.2 Hz, 1H), 7.31-7.27 (m, 1H), 3.93 (s, 3H), 3.55 (s, 2H).

Synthesis of Compound 4: Compound 3 (156 mg, 0.53 mmol) was dissolved in 5.3 mL of anhydrous 1,4-dioxane, hexa-n-butylditin (0.61 g, 1.05 mmol), tetrakis(triphenylphosphine)palladium (30 mg, 0.026 mmol) were added, reacted overnight at 100° C. The next day, water and ethyl acetate were added for extraction, the organic phase was washed with saturated brine, dried, concentrated, passed through a chromatographic column to obtain 128 mg of product. $^1$HNMR: ($CDCl_3$, 400 MHz) δ 7.75 (d, J=7.6 Hz, 1H), 7.47 (d, J=7.2 Hz, 1H), 7.35-7.31 (m, 1H), 7.25-7.21 (m, 1H), 4.01 (s, 3H), 3.61 (s, 2H), 1.68-1.52 (m, 25H), 1.41-1.18 (m, 49H), 0.94-0.88 (m, 32H).

Synthesis of Compound 5: Compound 4 (122 mg, 0.26 mmol) was dissolved in 5 mL of anhydrous 1,4-dioxane, 2,4-dichloropyrimidine-5-carboxylate isopropyl ester (87 mg, 0.37 mmol), tris(dibenzylideneacetone)dipalladium (48.5 mg, 0.053 mmol) were added, reacted for 3.5 h at 80° C., after reacting, water and ethyl acetate were added for extraction, the organic phase was washed with saturated brine, dried, concentrated, passed through a chromatographic column to obtain 29 mg of product. $^1$HNMR: ($CDCl_3$, 400 MHz) δ 9.08 (s, 1H), 7.79 (d, J=7.6 Hz, 1H), 7.45 (d, J=7.6 Hz, 1H), 7.39-7.35 (m, 1H), 7.30-7.28 (m, 1H), 5.19-5.10 (m, 1H), 4.11 (s, 3H), 3.54 (s, 2H), 1.16 (d, J=6.4 Hz, 6H).

Synthesis of Example 15: Compound 5 (30 mg, 0.08 mol) was dissolved in 1.2 mL of 1,2-dichloroethane and 1.2 mL of n-pentanol, INT 5 (23.3 mg, 0.08 mmol), p-toluenesulfonic acid monohydrate (13 mg, 0.068 mmol) were added, reacted overnight at 90° C., after reacting, the reaction solution was concentrated, a saturated aqueous sodium bicarbonate solution was added to wash, extracted with dichloromethane, the organic phase was washed with saturated brine, dried, concentrated, passed through a chromatographic column to obtain 22 mg of product. $^1$HNMR: ($CDCl_3$, 400 MHz) δ 9.01 (s, 1H), 8.22 (s, 1H), 7.70 (d, J=7.6 Hz, 1H), 7.49 (d, J=7.2 Hz, 1H), 7.36 (t, J=7.6 Hz, 1H), 7.29 (t, J=6.8 Hz, 1H), 6.95 (s, 1H), 6.51-6.37 (m, 2H), 5.80 (d, J=9.6 Hz, 1H), 5.06-4.99 (m, 1H), 3.97 (s, 3H), 3.92 (s, 3H), 3.65-3.63 (m, 1H), 3.56 (s, 2H), 3.49-3.46 (m, 2H), 3.41 (s, 1H), 3.31-3.21 (m, 2H), 2.83 (s, 6H), 2.70 (s, 3H), 1.10 (d, J=6.4 Hz, 6H).

Example 16

The structural formula of the compound used as the kinase inhibitor of the example is:

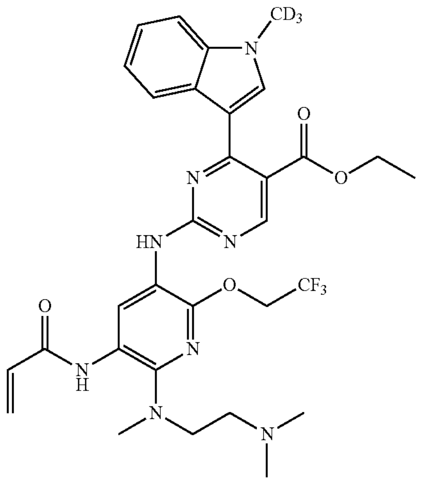 [SMILES: [2H]C([2H])([2H])n1cc(-c2nc(Nc3cc(NC(=O)C=C)c(N(C)CCN(C)C)nc3OCC(F)(F)F)ncc2C(=O)OCC)c2ccccc21]

Synthetic Route:

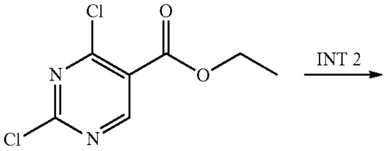

1

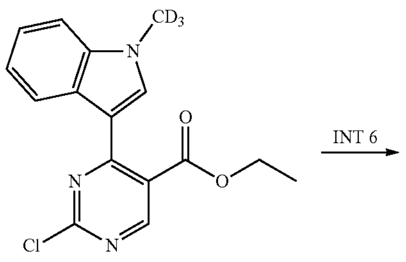

2

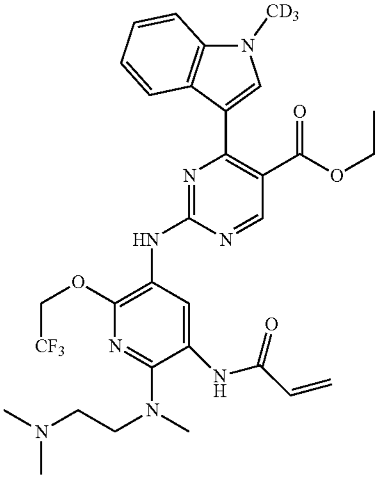

Example 16

Synthesis of Compound 2: in a 100 mL single-necked flask, Compound 1 (1.85 g, 8.4 mmol), DCE (40 mL) were respectively added, in an ice bath, aluminum trichloride (2.13 g, 16 mmol) was added, stirred for 5 minutes, INT 2 (1.2 g, 9 mmol) was then added, then heating reacted for 1.5 h at 50° C. After reacting, water was added, extracted with dichloromethane three times, the organic phase was combined, the organic phase was washed with saturated brine once, dried, passed through a chromatographic column to obtain 1.3 g of product.

Synthesis of Example 16: INT 6 (50 mg, 0.11 mmol), Compound 2 (36 mg, 0.11 mmol), p-toluenesulfonic acid monohydrate (31 mg, 0.17 mmol), 1 mL of NMP, and 2 mL of ethylene glycol monomethyl ether were added to a 5 mL reactor, heated to 120° C., reacted for 6 h, cooled to room temperature, 10 mL of ethyl acetate was added, washed with an aqueous sodium bicarbonate solution, washed with saturated brine once, dried, purified to obtain 20 mg of product. MS+1: 641.52

Example 17

The structural formula of the compound used as the kinase inhibitor of the example is:

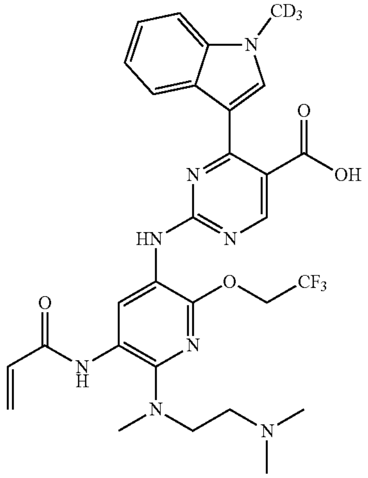 [SMILES: [2H]C([2H])([2H])n1cc(-c2nc(Nc3cc(NC(=O)C=C)c(N(C)CCN(C)C)nc3OCC(F)(F)F)ncc2C(=O)O)c2ccccc21]

Synthetic Route:

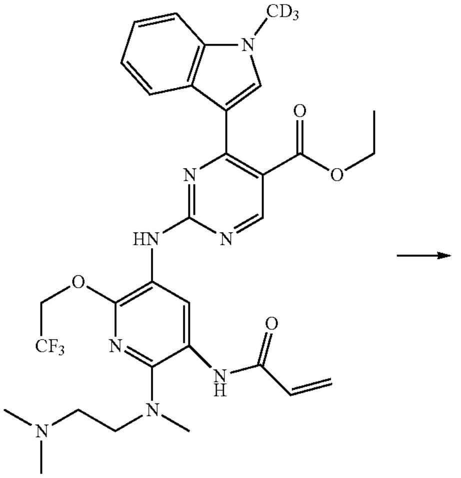

Example 16

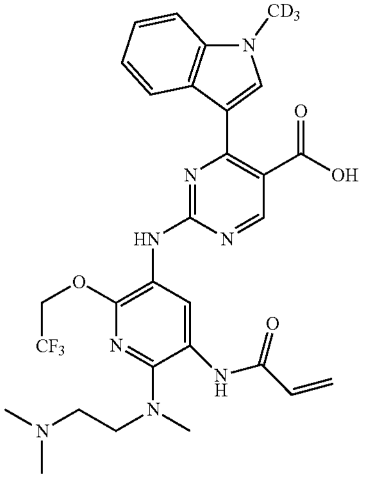

Example 17

Synthesis of Example 17: the compound of Example 16 (50 mg, 0.078 mmol), NaOH (36 mg, 0.9 mmol), 2 mL of ethanol were added to a 5 mL reactor, heated to 70° C., reacted for 6 h, cooled to room temperature, the raw materials were completely reacted, 10 mL of ethyl acetate was added, washed with an aqueous sodium bicarbonate solution, washed with saturated brine once, dried, purified to obtain 15 mg of product. MS+1: 613.48.

Example 18

The structural formula of the compound used as the kinase inhibitor of the example is:

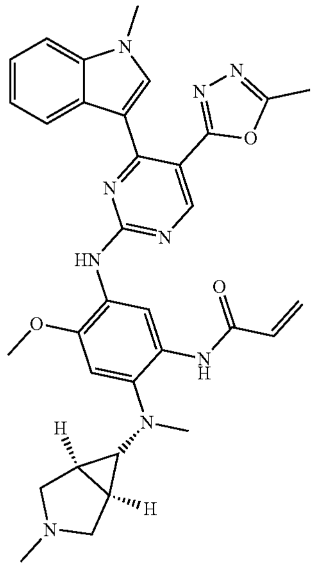

Synthetic Route:

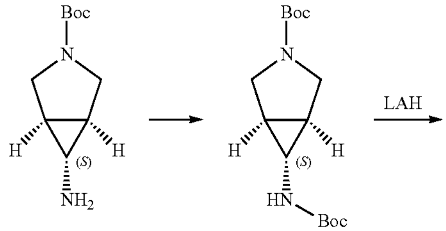

1

2

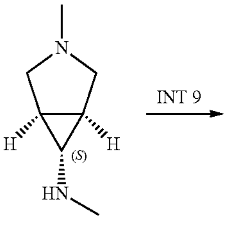

3

-continued

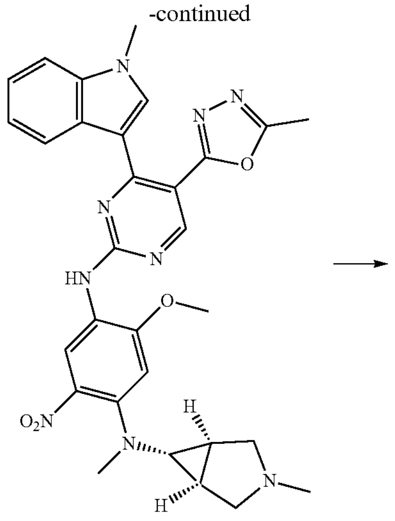

4

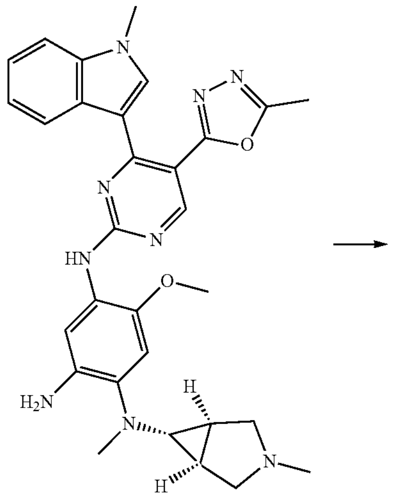

5

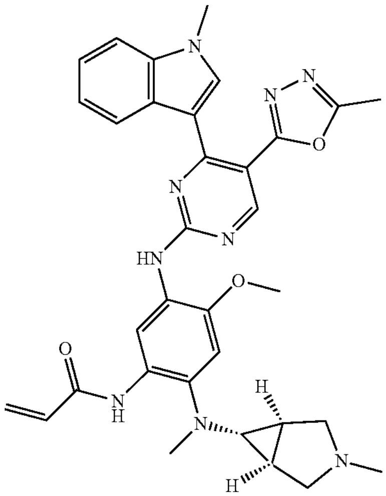

Example 18

Synthesis of Compound 2: Compound 1 (2 g, 10.1 mmol) was dissolved in dichloromethane, temperature was lowered to 0° C. under nitrogen protection, a dichloromethane solution of $Boc_2O$ (2.42 g, 11.1 mmol) was slowly added dropwise, DMAP (0.25 g, 2.05 mmol) was then added, temperature was slowly raised to room temperature, reacted for 16 h. After the raw materials were reacted, concentrated, passed through a chromatographic column to obtain 1.6 g of Compound 2. $^{1}$HNMR (400 MHz, $CDCl_3$) δ 4.76 (s, 1H), 3.66 (d, J=11.2 Hz, 2H), 3.37 (td, J=11.6, 4.0 Hz, 2H), 2.28 (s, 1H), 1.65 (dt, J=7.6, 5.2 Hz, 2H), 1.43 (d, J=8.8 Hz, 18H).

Synthesis of Compound 3: lithium tetrahydroaluminum (1.75 g, 46 mmol) was added to dry tetrahydrofuran, temperature was lowered to 0° C. under nitrogen protection, a tetrahydrofuran solution of Compound 2 (1.6 g, 5.36 mmol) was slowly added dropwise, temperature was then raised to 70° C., reacted for 16 hours. After the raw materials were reacted, temperature was lowered to 0° C., and 2 mL of water and 2 mL of 20% aqueous sodium hydroxide solution were slowly added dropwise, filtered to obtain 1.48 g of Compound 3.

Synthesis of Compound 4: INT 9 (250 mg, 0.526 mmol), Compound 3 (100 mg, 0.793 mmol), and DIPEA (203 mg, 1.57 mmol) were added to N,N-dimethylacetamide, reacted for 16 h at 100° C. After the raw materials were reacted, water was added to the reaction system, extracted with ethyl acetate three times, the organic phase was combined, washed with brine, dried, concentrated, passed through a chromatographic column to obtain 280 mg of product.

Synthesis of Compound 5: Compound 4 (280 mg, 0.481 mmol) and palladium on carbon (56 mg, 20%) were added to methanol, under a hydrogen atmosphere, reacted for 2 h at room temperature. After the raw materials were reacted, diatomite was added for filtration, the filter cake was washed with methanol three times, the filtrate was combined, 190 mg of Compound 5 was obtained after spin-drying.

Synthesis of Example 18: Compound 5 (190 mg, 0.345 mmol) and triethylamine (104 mg, 1.03 mmol) were dissolved in dichloromethane, temperature was lowered to 0° C. under nitrogen protection, a dichloromethane solution of acryloyl chloride (41 mg, 0.45 mmol) was then added dropwise, reacted for 2 h while maintaining at 0° C. After the raw materials were reacted, a saturated aqueous sodium bicarbonate solution was added, extracted with dichloromethane three times, the organic phase was combined, washed with brine, dried, concentrated, passed through a chromatographic column to obtain 30 mg of product. $^{1}$HNMR (400 MHz, $CDCl_3$) δ 10.54 (s, 1H), 9.66 (s, 1H), 8.89 (m, 2H), 7.97 (s, 1H), 7.32 (d, J=8.0 Hz, 1H), 7.16 (t, J=8.0 Hz, 1H), 6.98 (m, 2H), 6.84 (s, 1H), 6.44 (dd, J=16.8, 2.0 Hz, 1H), 6.36-6.24 (m, 1H), 5.69 (dd, J=10.0, 2.0 Hz, 1H), 3.99 (s, 3H), 3.90 (s, 3H), 3.05 (m, 1H), 2.65 (m, 7H), 2.32 (s, 3H), 2.20 (s, 3H), 1.08 (s, 2H).

Example 19

The structural formula of the compound used as the kinase inhibitor of the example is:

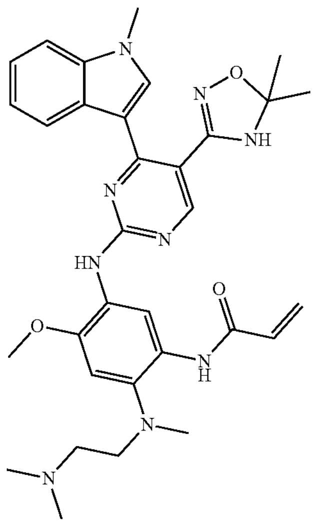

Synthetic Route:

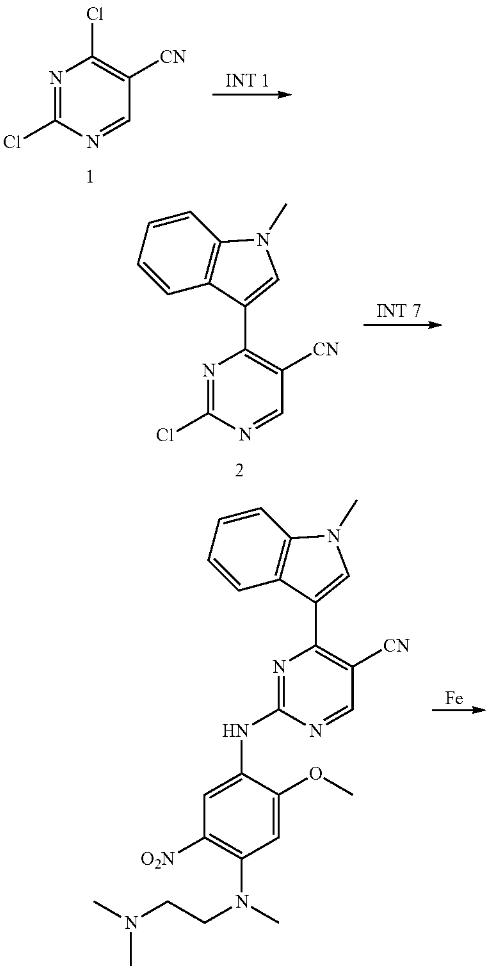

1
2
3

-continued

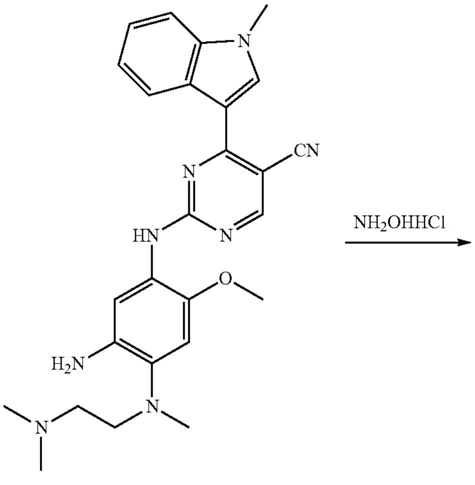

4

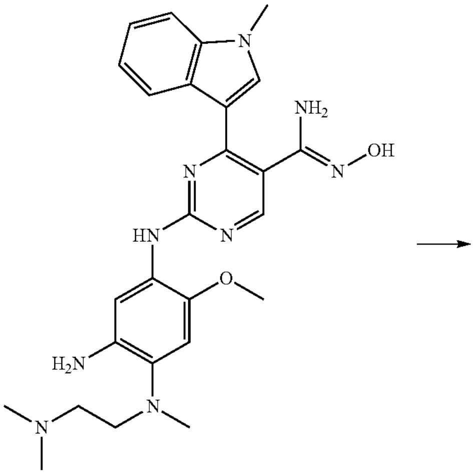

5

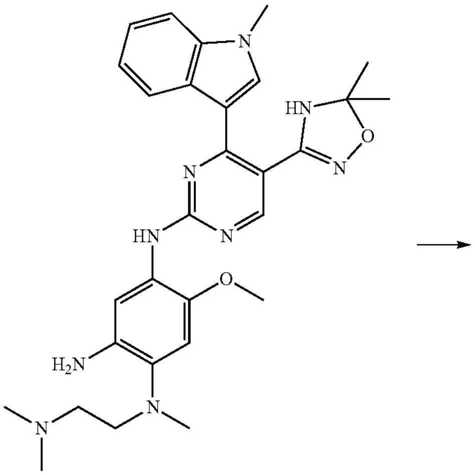

6

-continued

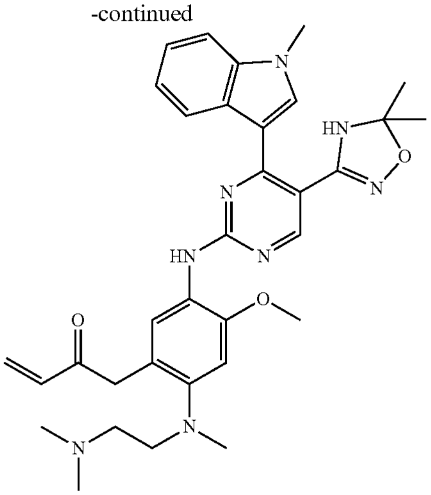

Example 19

Synthesis of Compound 2: Compound 1 (5 g, 28.9 mmol) and $AlCl_3$ (5.76 g, 43.3 mmol) were dissolved in 50 mL of dry 1,2-dichloroethane, temperature was raised to 80° C. under nitrogen protection and reacted for 1 h, a dichloroethane solution (4.53 g, 34.6 mmol) of methyl indole was then slowly added dropwise while stirring, reaction was continued for 3 h at 80° C. after adding. After reacting, temperature was lowered, ice water was slowly poured, extracted with dichloromethane three times, the organic phase was combined, dried, passed through a chromatographic column to obtain 2.6 g of product.

Synthesis of Compound 3: Compound 2 (1.5 g, 5.6 mmol) and INT-7 (1.8 g, 6.71 mmol) were dissolved in dioxane and water, p-toluenesulfonic acid monohydrate (1.59 g, 8.37 mmol) was added, temperature was raised to 80° C., reacted for 16 h. After the raw materials were reacted, the reaction solution was spin-dried, 2N aqueous sodium hydroxide solution was added to adjust alkali, then extracted with ethyl acetate three times, the organic phase was combined, dried, concentrated, passed through a chromatographic column to obtain 2.5 g of product.

Synthesis of Compound 4: Compound 3 (0.5 g, 1 mmol) was dissolved in a mixed solvent of ethanol and water, iron powder (0.448 g, 8 mmol) and ammonium chloride (0.43 g, 8 mmol) were added while stirring, temperature was raised to 80° C., reacted for 2 h. After the raw materials were reacted, ethanol was spun off, ammonia water was added to adjust alkali, then extracted with ethyl acetate three times, the organic phase was combined, dried, concentrated to obtain 0.45 g of crude product.

Synthesis of Compound 5: Compound 4 (0.45 g), hydroxylamine hydrochloride (0.4 g, 5.74 mmol), and anhydrous potassium acetate (1.125 g, 11.4 mmol) were added to a mixed solvent of ethanol and dioxane, reflux-reacted for 16 h at 80° C., after the raw materials were reacted, most of the solvent was spun off, water and ethyl acetate were then added, extracted three times, the organic phase was combined, dried, concentrated, passed through a chromatographic column to obtain 0.37 g of product.

Synthesis of Compound 6: Compound 5 (0.37 g, 0.734 mmol) and 2,2-dimethoxypropane (0.61 g, 5.87 mmol) were dissolved in a mixed solvent of 1,2-dichloroethane and acetic acid, reflux-reacted for 2 h at 80° C. After the raw materials were reacted, most of the solvent was spun off. A saturated sodium bicarbonate solution was then added to adjust pH=8, extracted with dichloromethane three times, the organic phase was combined, dried, concentrated, passed through a chromatographic column to obtain 0.17 g of product.

Synthesis of Example 19: Compound 6 (0.17 g, 0.312 mmol) and triethylamine (47 mg, 0.468 mmol) were dissolved in dry dichloromethane, temperature was lowered to 0° C., a dichloromethane solution (31 mg, 0.343 mmol) of acryloyl chloride was then added dropwise, reacted for 2 h while maintaining at 0° C. After the raw materials were reacted, water and dichloromethane were added, extracted three times, the organic phase was combined, dried, concentrated, passed through a chromatographic column to obtain 60 mg of product. $^1$HNMR (400 MHz, $CDCl_3$): δ 10.15 (s, 1H), 10.13 (s, 1H), 9.92 (s, 1H), 9.16 (s, 1H), 8.62-8.60 (m, 1H), 8.54 (s, 1H), 7.36-7.34 (m, 1H), 7.24-7.23 (m, 3H), 6.82 (m, 1H), 6.50-6.37 (m, 2H), 5.71 (dd, J=22.64, 2.6 Hz, 1H), 3.97 (s, 3H), 3.93 (s, 3H), 2.92 (t, J=5.4, 5.8 Hz, 2H), 2.71 (s, 3H), 2.32 (t, J=5.72, 5.64 Hz, 2H)), 2.28 (s, 6H), 1.63 (s, 6H).

Example 20

The structural formula of the compound used as the kinase inhibitor of the example is:

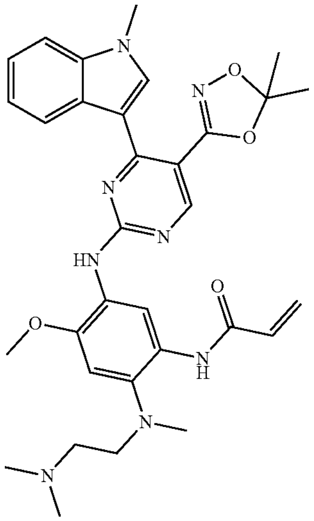

Synthetic Route:

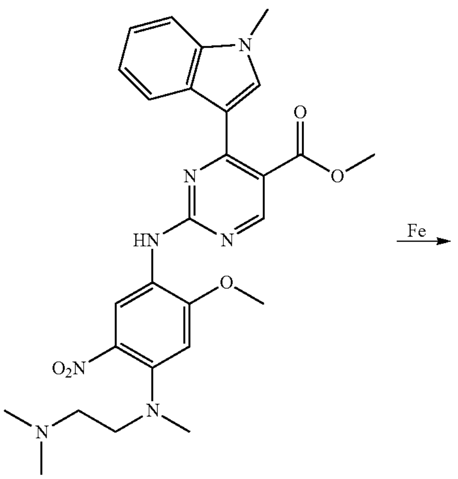

INT 8

-continued

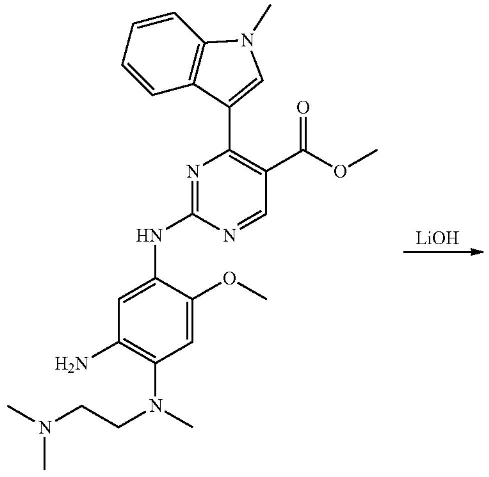

2

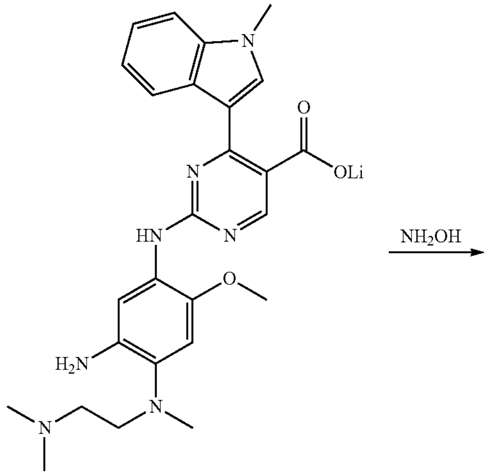

3

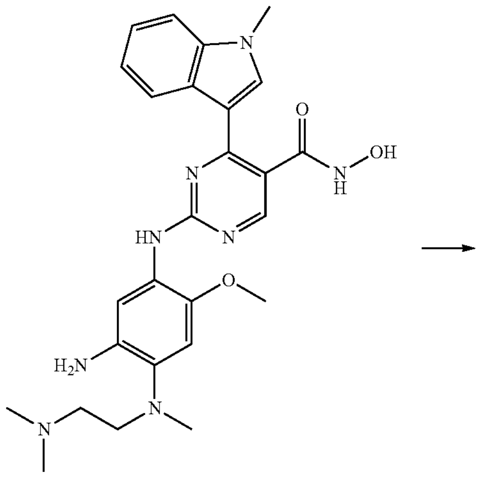

4

-continued

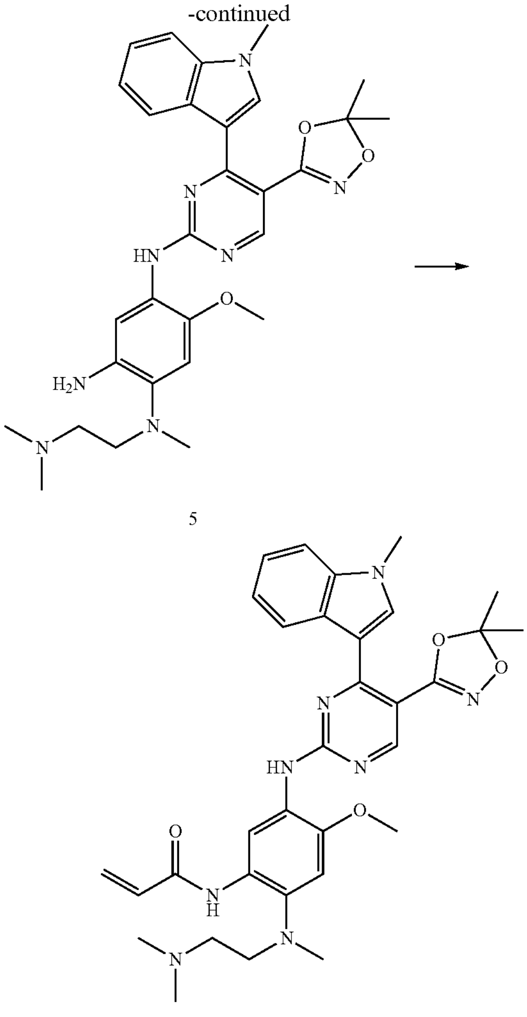

5

Example 20

Synthesis of Compound 2: INT 8 (5 g, 9.38 mmol) was dissolved in ethanol and water, iron powder (4.2 g, 75.1 mmol) and ammonium chloride (4.1 g, 75.1 mmol) were added while stirring, after addition was completed, temperature was raised to 80° C., reacted for 2 h. After the raw materials were reacted, most of the ethanol in the reaction solution was spun off, ammonia water was then added to adjust alkali, then extracted with ethyl acetate three times, the organic phase was combined, dried, 5 g of crude product was obtained after concentration.

Synthesis of Compound 3: Compound 2 (5 g) and lithium hydroxide (2.08 g, 49.7 mmol) were added to a mixed solvent of methanol, tetrahydrofuran, and water, reacted for 16 h at room temperature. After the raw materials were reacted, most of the solvent was spun off, 4.6 g of crude product was then obtained after toluene with water three times.

Synthesis of Compound 4: the crude product of Compound 3 (2 g), DIPEA (1.58 g, 12.2 mmol), and hydroxylamine hydrochloride (0.84 g, 12.2 mmol) were dissolved in dry DMF, reacted for 15 minutes at room temperature, PyBop (2.5 g, 4.91 mmol) was added, under nitrogen protection, reacted for 16 h at room temperature, monitored by TLC, after the raw materials were reacted, water and ethyl acetate were added to the reaction system for extraction, the organic phase was combined, dried, concentrated, passed through a chromatographic column to obtain 0.6 g of product.

Synthesis of Compound 5: Compound 4 (0.6 g, 1.18 mmol) and 2,2-dimethoxypropane (0.99 g, 9.51 mmol) were dissolved in a mixed solvent of 1,2-dichloroethane and acetic acid, reflux-reacted for 2 h at 80° C. After the raw materials were reacted, most of the solvent was spun off, a saturated sodium bicarbonate solution was then added to adjust pH=8, then extracted with dichloromethane three times, the organic phase was combined, dried, the solvent was spin-dried, passed through a chromatographic column to obtain 0.13 g of product.

Synthesis of Example 20: Compound 5 (0.13 g, 0.238 mmol) and triethylamine (36 mg, 0.357 mmol) were dissolved in dry dichloromethane, temperature was lowered to 0° C., a dichloromethane solution (0.0238 g, 0.262 mmol) of acryloyl chloride was then added dropwise, reacted for 2 h while maintaining at 0° C. After the raw materials were reacted, water was added, extracted with dichloromethane three times, the organic phase was combined, dried, concentrated, passed through a chromatographic column to obtain 14 mg of product. $^1$HNMR (400 MHz, CDCl3): δ 8.95 (s, 1H), 8.54 (s, 1H), 8.20 (s, 1H), 2.92 (d, J=8.12 Hz, 2H), 7.86 (s, 1H), 7.31-7.22 (m, 2H), 7.10 (t, J=7.64, 7.32 Hz, 1H), 6.63 (s, 1H), 6.59-6.53 (m, 1H), 6.30 (d, J=16.52 Hz, 1H)), 5.71 (d, J=10.24 Hz, 1H), 3.86 (s, 3H), 3.80 (s, 3H), 3.31 (t, J=5.4, 5.8 Hz, 2H), 3.16 (t, J=5.72, 5.64 Hz, 2H), 2.73 (s, 6H), 2.60 (s, 3H), 1.48 (s, 6H).

Example 21

The structural formula of the compound used as the kinase inhibitor of the example is:

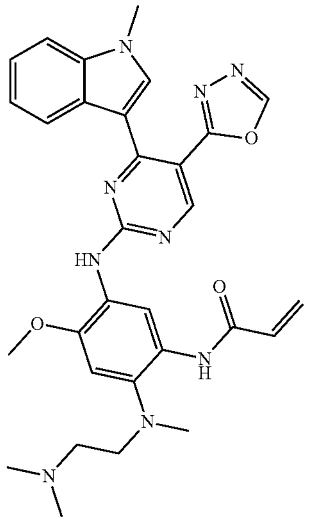

Synthetic Route:

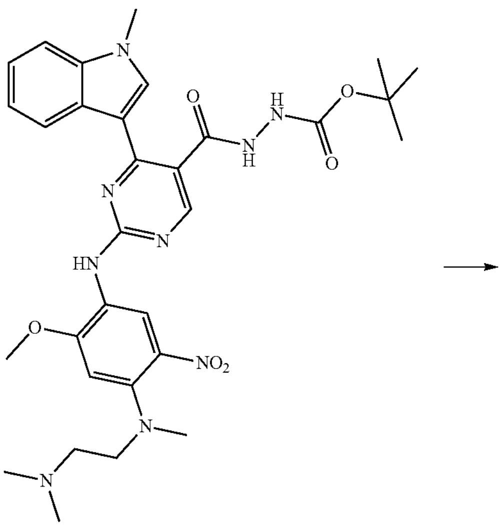

INT 10

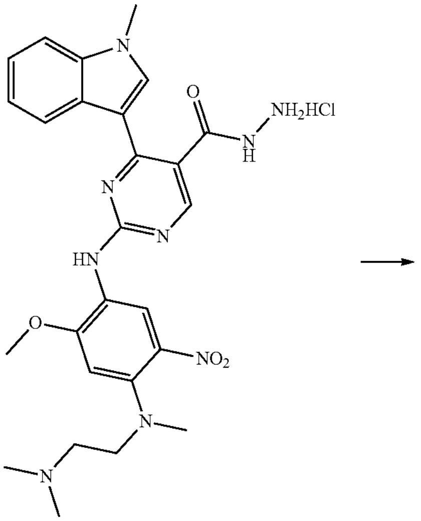

2

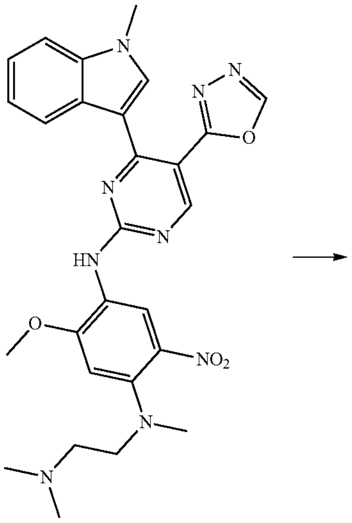

3

-continued

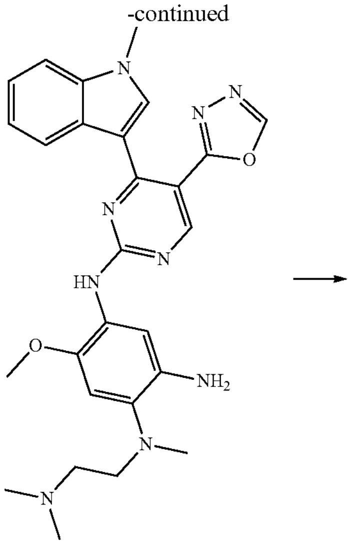

4

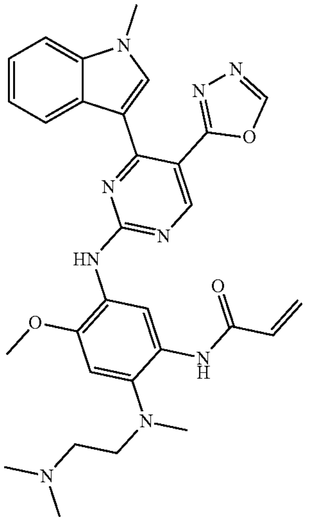 [SMILES: C=CC(=O)Nc1cc(Nc2ncc(-c3nnco3)c(-c3cn(C)c4ccccc34)n2)c(OC)cc1N(C)CCN(C)C]

Example 21

Synthesis of Compound 2: in a 250 ml single-necked flask, 90 ml of dioxane hydrochloride was added, under nitrogen protection. INT 10 (1.52 g, 2.40 mmol) was dissolved in 50 mL of dry THF, and added dropwise to a reaction flask, 10 mL of dry THF was then taken and also added dropwise to the reaction flask, stirred for 4 h at 40° C., temperature was lowered to 0° C., filtered with suction, the filter cake was washed with dry THF, dried under vacuum to obtain 1.324 g of product.

Synthesis of Compound 3: Compound 2 (0.843 g, 1.48 mmol) was taken, 16 mL of triethyl orthoformate was added, reflux-reacted for 2 hours at 160° C. The solvent was evaporated under reduced pressure, temperature was lowered, a mixture of methanol and dichloromethane was added to dissolve, passed through a chromatographic column to obtain 0.154 g of pure product. $^1$HNMR (400 MHz, DMSO-d6) δ 9.27 (s, 1H), 8.99 (s, 1H), 8.62 (s, 1H), 8.26 (s, 1H), 7.86 (s, 1H), 7.48 (d, J=8.3 Hz, 1H), 7.44 (s, 1H), 7.21 (d, J=15.2 Hz, 1H), 7.01 (s, 1H), 6.84 (s, 1H), 3.91 (s, 3H), 3.78 (s, 3H), 3.33 (s, 13H), 2.87 (s, 3H), 2.50 (p, J=1.9 Hz, 14H), 2.19 (s, 5H).

Synthesis of Compound 4: Compound 3 (154 mg, 0.284 mmol), zinc powder (110 mg, 1.69 mmol), and ammonium chloride (149 mg, 2.78 mmol) were added to 3 mL of acetone and 0.3 mL of water, addition was completed, temperature was raised to 26° C., reacted for 2 h. A saturated aqueous solution of sodium bicarbonate, dichloromethane, and a little methanol were added, extracted twice, dried, spin-dried to obtain 0.235 g of crude product, directly put into the next step.

Synthesis of Example 21: in a 100 mL single-necked flask, crude product of Compound 4 (0.235 g), 10 mL of dichloromethane, triethylamine (85 mg, 0.84 mmol) were added, temperature was lowered to 0° C., acryloyl chloride (33 mg, 0.37 mmol) was added dropwise, reacted for 3 h while maintaining at 0° C. After the raw materials were reacted, a saturated aqueous sodium bicarbonate solution was added, extracted with dichloromethane twice, dried, concentrated, passed through a chromatographic column to obtain 15 mg of product. $^1$HNMR (400 MHz, $CDCl_3$) δ 10.17 (s, 1H), 9.78 (s, 1H), 8.92 (s, 1H), 8.85 (m, 1H), 8.16 (s, 1H), 7.97 (s, 1H), 7.31 (d, J=8.2 Hz, 1H), 7.15 (t, J=6.2 Hz, 1H), 6.94 (d, J=7.2 Hz, 2H), 6.80 (m, 2H), 6.53-6.35 (m, 2H), 5.81-5.64 (m, 1H), 3.95 (s, 3H), 3.89 (s, 4H), 2.90 (t, J=5.5 Hz, 2H), 2.70 (s, 3H), 2.32 (s, 2H)), 2.28 (s, 6H).

Examples 22 and 23

With reference to Example 18, Examples 22 and 23 were synthesized, as shown in Table 1 below:

TABLE 1

Compounds of Examples 22 and 23

| Number | Structure | Characterization |
|---|---|---|
| Example 22 | 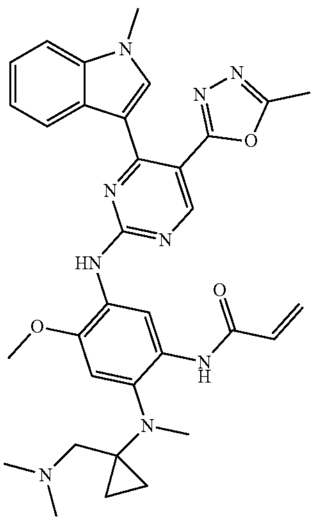 | MS + 1 = 608.3 |

TABLE 1-continued

Compounds of Examples 22 and 23

| Number | Structure | Characterization |
|---|---|---|
| Example 23 | 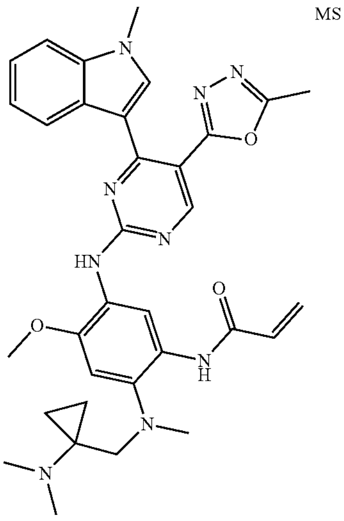 | MS + 1 = 608.3 |

Example 24

The structural formula of the compound used as the kinase inhibitor of the example is:

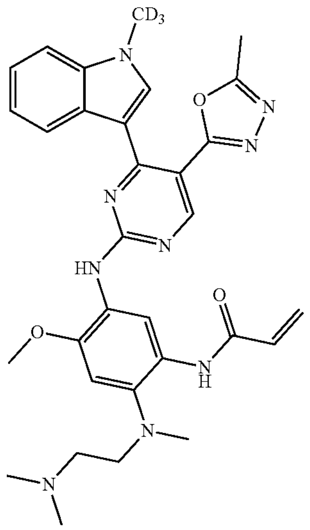 [SMILES: [2H]C([2H])([2H])n1cc(-c2nc(Nc3cc(NC(=O)C=C)c(N(C)CCN(C)C)cc3OC)ncc2-c2nnc(C)o2)c2ccccc21]

Synthetic Route:

Example 24

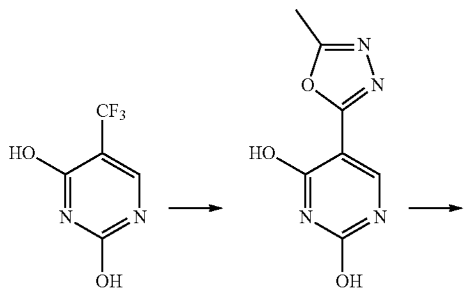

1 2

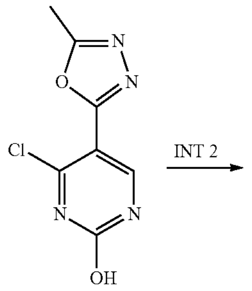

3

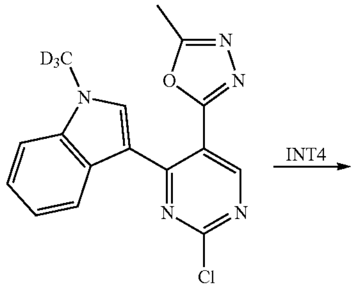

4

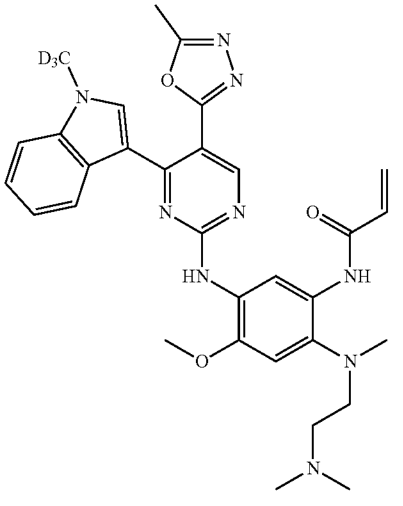

Example 24

Synthesis of Compound 2: in a 1000 mL single-necked flask, Compound 1 (24 g, 133 mmol), acethydrazide (12.7 g, 172 mmol) were added, 400 mL of 1N aqueous sodium hydroxide solution was added, reacted for 4 h at 80° C., a large amount of yellow solid was precipitated. Temperature was lowered, 33 mL of concentrated hydrochloric acid was added, stirred for 30 minutes at a low temperature of about 0° C., filtered with suction, the filter cake was stirred and washed with water once, dried under vacuum overnight at 55° C. to obtain 18.8 g of yellow solid product.

Synthesis of Compound 3: in a 1000 mL single-necked flask, Compound 2 (18.8 g, 97 mmol) was added, 450 mL of toluene, phosphorus oxychloride (89.3 g, 583 mmol), DIPEA (50.1 g, 389 mmol) were added at room temperature, white mist was generated. Heated to 80° C., under nitrogen protection, stirred overnight. The next day, most of the solvent was spun off, the reaction solution was poured into crushed ice, extracted with ethyl acetate three times, the organic phase was combined, dried, concentrated, passed through a chromatographic column to obtain 12.08 g of product.

Synthesis of Compound 4: in a 250 mL single-necked flask, Compound 3 (2.38 g, 10.3 mmol) was added, completely dissolved with 120 mL of 1,2-dichloroethane, anhydrous aluminum trichloride (2.33 g, 17.5 mmol) was added, first stirred for 30 minutes at room temperature. Temperature was lowered to 0° C., INT 2 (1.52 g, 11.33 mmol) was added dropwise, first stirred for 30 min at low temperature, temperature was then raised to 50° C., reacted for 2 h. Temperature was lowered, poured into ice water, extracted with dichloromethane twice, dried, spin-dried, passed through a chromatographic column to obtain 1.24 g of product. $^{1}$HNMR (400 MHz, $CDCl_3$) δ 8.84 (s, 1H), 8.05-8.00 (m, 1H), 7.96 (s, 1H), 7.42-7.26 (m, 3H), 2.50 (s, 3H).

Synthesis of Example 24: in a 100 mL single-necked flask, Compound 4 (0.397 g, 1.22 mmol), p-toluenesulfonic acid monohydrate (0.3 g, 1.58 mol), INT4 (0.526 g, 1.34 mmol), 20 mL of NMP, and 40 mL of ethylene glycol monomethyl ether were added. Under nitrogen protection, stirred overnight at 120° C., the next day, 0.2 mL of 1N sodium hydroxide was added, extracted with ethyl acetate three times, dried, concentrated, passed through a chromatographic column to obtain 40 mg of product. $^{1}$HNMR (400 MHz, $CDCl_3$) δ 10.22 (s, 1H), 9.78 (s, 1H), 8.89 (m, 2H), 7.95 (s, 1H), 7.31 (d, J=8.2 Hz, 1H), 7.15 (m, 1H), 6.97 (t, J=7.8 Hz, 2H), 6.80 (s, 1H), 6.46 (dd, J=16.9, 2.1 Hz, 1H), 6.36 (dd, J=17.0, 9.9 Hz, 1H), 5.71 (dd, J=9.8, 2.1 Hz, 1H), 3.88 (s, 3H), 2.88 (t, J=5.6 Hz, 2H), 2.70 (s, 3H), 2.26 (s, 8H), 2.19 (s, 3H).

Example 25

The structural formula of the compound used as the kinase inhibitor of the example is:

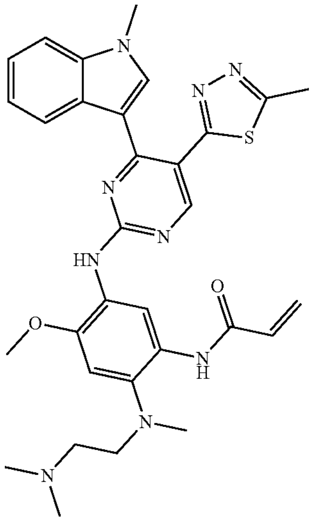
Synthetic Route:
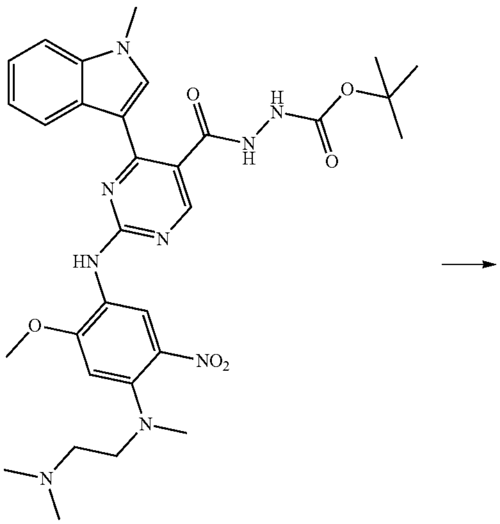
INT 10
-continued
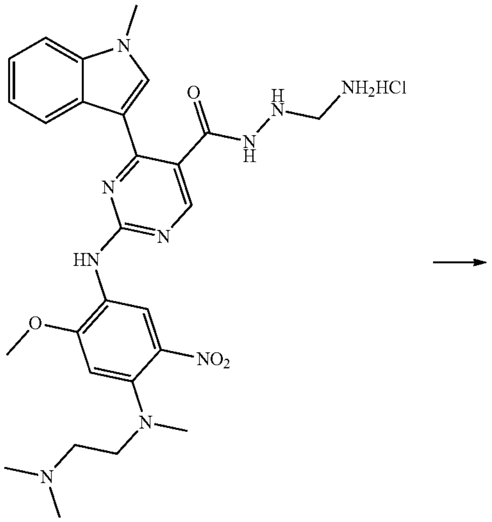
2
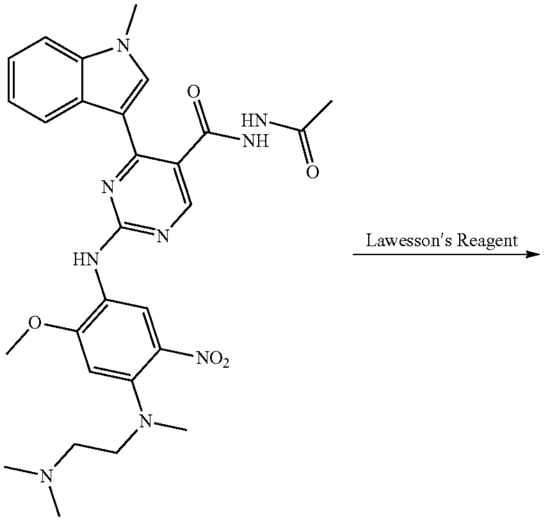
3
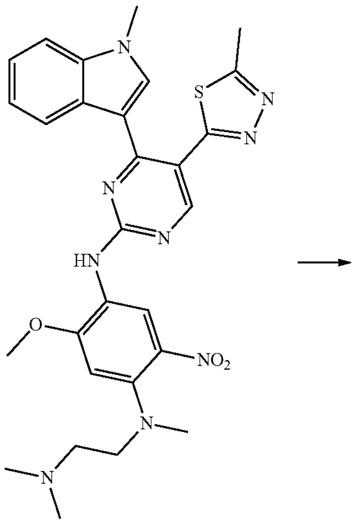
4

-continued

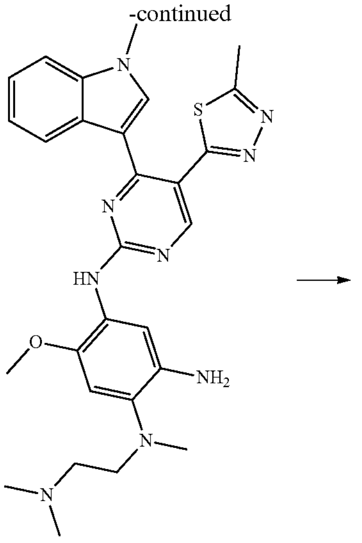

5

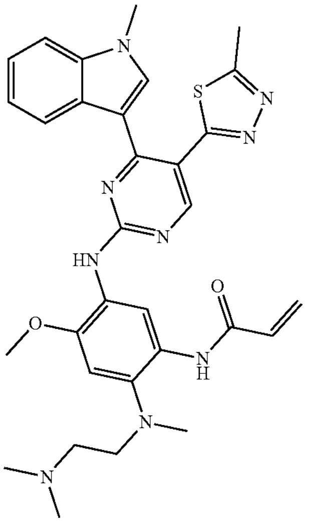

Example 25

Synthesis of Compound 2: in a 250 mL single-necked flask, 120 mL of dioxane hydrochloride was added, under nitrogen protection. INT 10 (2.08 g) was dissolved in 55 mL of dry THF, added dropwise to a reaction flask, stirred for 4 hours at 40° C., temperature was lowered to 0° C., filtered with suction, the filter cake was washed with THF, dried under vacuum to obtain 3.3 g of product.

Synthesis of Compound 3: Compound 2 (0.871 g, 1.53 mmol) and triethylamine (0.463 g, 4.59 mmol) were dissolved in dichloromethane, first stirred for 5 minutes, temperature was lowered to 0° C. in an ice bath, acetic anhydride (0.172 g, 1.683 mmol) was added dropwise, stirred for 30 minutes at low temperature, then stirred overnight at 25° C. The next day, the raw materials disappeared, an aqueous sodium bicarbonate solution was added, extracted with dichloromethane twice, the organic phase was combined, dried, passed through a chromatographic column to obtain 0.73 g of product.

Synthesis of Compound 4: Compound 3 (0.133 g) was taken, 0.4 g of Lawesson's reagent was added, 20 mL of THF was then added, reflux-reacted for 2 hours at 80° C., the raw materials disappeared. Temperature was lowered, processed, passed through a chromatographic column to obtain 0.13 g of product.

Synthesis of Compound 5: Compound 4 (1.4 g, 2.44 mmol), zinc powder (0.955 g, 14.7 mmol), and ammonium chloride (1.31 g, 24.5 mmol) were added, temperature was raised to 26° C. after adding, reacted for 2 h. The raw materials disappeared, a saturated aqueous solution of sodium bicarbonate was added, extracted with dichloromethane twice, dried, concentrated to obtain 0.6 g of crude product, directly put into the next step.

Synthesis of Example 25: Compound 5 (0.6 g) and triethylamine (0.33 g, 3.26 mmol) were dissolved in 50 mL of dichloromethane, temperature was lowered to 0° C., acryloyl chloride (130 mg, 1.44 mmol) was added dropwise, reacted for 3 h while maintaining at 0° C., and the reaction of the raw materials was completed. A saturated aqueous sodium bicarbonate solution was added, extracted with dichloromethane twice, dried, concentrated, passed through a column, then purified to obtain 200 mg of product. $^1$HNMR (400 MHz, $CDCl_3$) δ 9.77 (s, 1H), 9.57 (m, 1H), 8.90 (s, 1H), 8.56 (m, 1H), 7.89 (s, 1H), 7.30 (d, J=8.2 Hz, 1H), 7.14 (t, J=7.6 Hz, 1H), 6.95 (t, J=7.5 Hz, 2H), 6.71 (s, 1H), 6.50 (dd, J=16.8, 2.0 Hz, 1H), 5.76 (ddd, J=10.0, 7.9, 1.9 Hz, 2H), 3.90 (s, 3H), 3.88 (s, 3H), 3.16 (m, 2H), 2.86 (m, 2H), 2.69 (s, 4H)), 2.61 (s, 9H).

Example 26

The structural formula of the compound used as the kinase inhibitor of the example is:

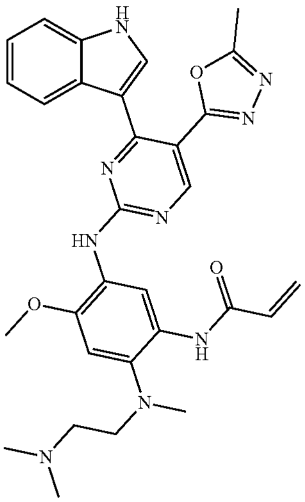 [SMILES: C=CC(=O)Nc1cc(Nc2ncc(-c3nnc(C)o3)c(-c3c[nH]c4ccccc34)n2)c(OC)cc1N(C)CCN(C)C]

Synthetic Route:

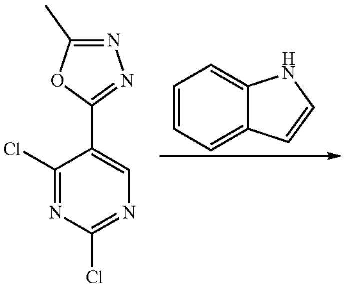

1

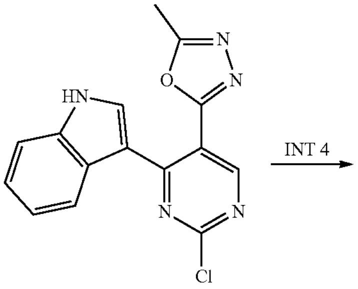

2

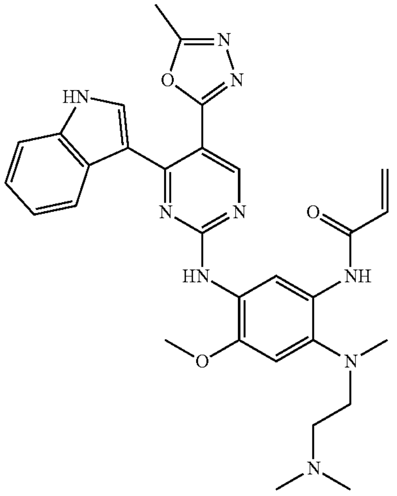

Example 26

Synthesis of Compound 2: in a 100 mL single-necked flask, Compound 1 (0.624 g, 2.71 mmol) was dissolved in 40 mL of 1,2-dichloroethane, aluminum trichloride (0.613 g, 4.61 mmol) was added, stirred for 30 minutes at room temperature, temperature was then lowered in an ice-salt bath, a dichloroethane solution of indole (0.349 g, 2.98 mmol) was added dropwise, stirred for 30 minutes at low temperature, temperature was raised to 50° C., stirred for 2 h, temperature was lowered, poured into ice water, extracted with ethyl acetate three times, the organic phase was combined, dried, passed through a chromatographic column to obtain 0.245 g of solid product.

Synthesis of Example 26: in a 100 mL single-necked flask, Compound 2 (0.245 g, 0.79 mmol), p-toluenesulfonic acid (0.195 g, 1.03 mol), INT 4 (0.34 g, 0.87 mmol), 10 mL of NMP, 20 mL of ethylene glycol monomethyl ether were added, under nitrogen protection, stirred overnight at 120° C. The next day, an aqueous sodium hydroxide solution was added, extracted with ethyl acetate three times. The ethyl ester phase was combined, concentrated, dried, passed through a chromatographic column to obtain 20 mg of product. $^{1}$HNMR (400 MHz, $CDCl_3$) δ 10.27 (m, 1H), 9.69 (s, 1H), 9.27 (s, 1H), 8.85 (s, 1H), 8.43 (m, 1H), 7.93 (s, 1H), 7.34 (d, J=8.1 Hz, 1H), 7.10 (t, J=7.6 Hz, 1H), 6.99 (m, 2H), 6.80 (s, 1H), 6.54-6.27 (m, 2H), 5.70 (dd, J=9.9, 1.9 Hz, 1H), 3.88 (s, 3H), 2.89 (t, J=5.5 Hz, 2H), 2.71 (s, 3H), 2.26 (m, 11H).

Example 27

The structural formula of the compound used as the kinase inhibitor of the example is:

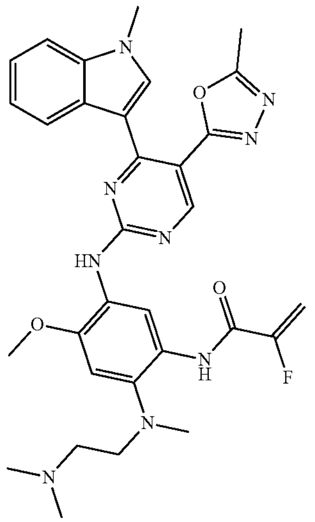 [SMILES: C=C(F)C(=O)Nc1cc(Nc2ncc(-c3nnc(C)o3)c(-c3cn(C)c4ccccc34)n2)c(OC)cc1N(C)CCN(C)C]

Synthetic Route:

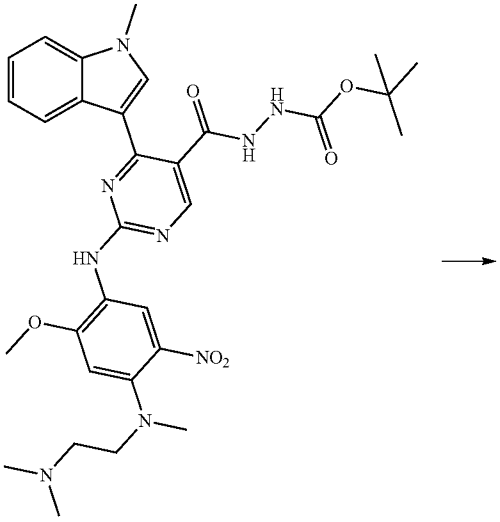

INT 10

-continued

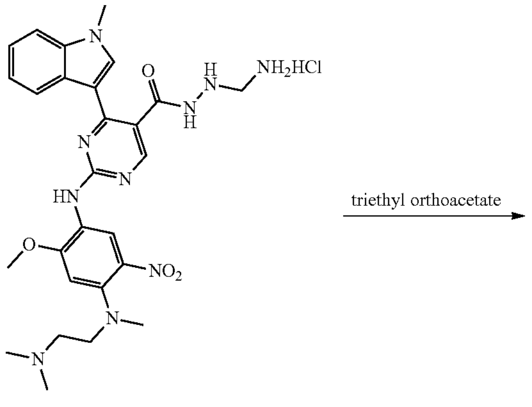

2

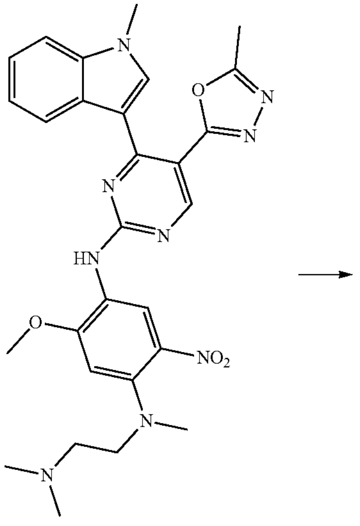

3

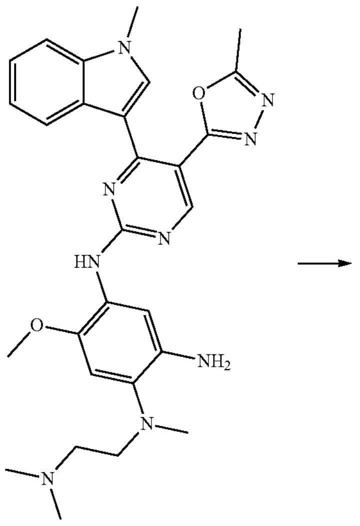

4

-continued

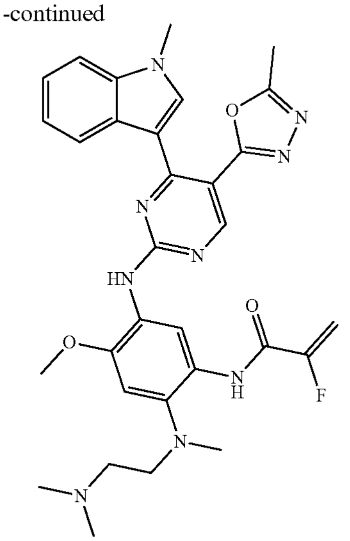

Example 27

Synthesis of Compound 2: in a 250 mL single-necked flask, 90 mL of dioxane hydrochloride was added, under nitrogen protection. INT 10 (1.52 g) was dissolved in 50 mL of dry THF, added dropwise to a reaction flask, 10 mL of THF was then taken and also added dropwise to the reaction flask, stirred for 4 h at 40° C., temperature was lowered to 0° C., filtered with suction, the filter cake was washed with THF, dried under vacuum to obtain 1.324 g of product.

Synthesis of Compound 3: Compound 2 (1.324 g) was taken, 17 mL of triethyl orthoacetate was added, reflux-reacted for 2 hours at 160° C., the raw materials disappeared. The solvent was evaporated under reduced pressure, temperature was lowered, a mixture of methanol and dichloromethane was added to dissolve, passed through a chromatographic column to obtain 0.42 g of pure product. $^1$HNMR (400 MHz, DMSO-d6) δ 9.01 (s, 1H), 8.60 (s, 1H), 8.35 (s, 1H), 7.94 (m, 1H), 7.53 (s, 1H), 7.49 (d, J=8.2 Hz, 1H), 7.27-7.19 (m, 1H), 7.04 (d, J=7.8 Hz, 1H), 6.91 (s, 1H), 3.95 (s, 3H), 3.80 (s, 3H), 3.48 (t, J=7.0 Hz, 2H), 3.03 (m, 2H), 2.86 (s, 6H), 2.56 (s, 3H), 2.47 (s, 3H).

Synthesis of Compound 4: Compound 3 (420 mg, 0.75 mmol), zinc powder (294 mg, 4.5 mmol), and ammonium chloride (403 mg, 7.5 mmol) were added, temperature was raised to 26° C. after adding, reacted for 2 h. The raw materials disappeared, a saturated aqueous solution of sodium bicarbonate was added, extracted with dichloromethane twice, dried, spin-dried to obtain 667 mg of crude product, directly put into the next step.

Synthesis of Example 27: in a 100 mL single-necked flask, 0.177 g of 2-fluoroacrylic acid, 10 mL of dichloromethane were added. Temperature of an ice-salt bath was lowered to −5° C. under nitrogen protection, 0.25 g of oxalyl chloride and 2 drops of dry DMF were added dropwise, reacted for 2 hours at low temperature. Another 250 mL single-necked flask was taken, crude product of Compound 4 (667 mg) and DIPEA (490 mg, 3.8 mmol) were dissolved in 100 mL of dichloromethane, temperature was lowered to 0° C., homemade 2-fluoroacryloyl chloride was then added dropwise, reacted for 3 h while maintaining at 0° C., after the raw materials were reacted, a saturated aqueous sodium bicarbonate solution was added, extracted with dichloromethane twice, dried, concentrated, passed through a chromatographic column to obtain 120 mg of product.

$^1$HNMR (400 MHz, Chloroform-d) δ 10.48 (s, 1H), 9.61 (s, 1H), 8.89 (s, 1H), 8.63 (s, 1H), 7.98 (s, 1H), 7.32 (dt, J=8.4, 0.9 Hz, 1H), 7.17 (t, J=8.0 Hz, 1H), 7.00 (d, J=7.4 Hz, 1H), 6.82 (s, 1H), 5.76 (dd, J=46.5, 3.0 Hz, 1H), 5.21 (dd, J=14.9, 3.0 Hz, 1H), 3.95 (s, 3H), 3.91 (s, 3H), 2.97 (t, J=6.3 Hz, 2H), 2.68 (s, 3H)), 2.21 (s, 11H).

Example 28

The structural formula of the compound used as the kinase inhibitor of the example is:

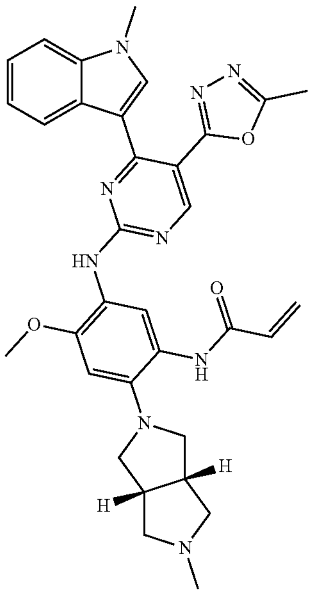

Synthetic Route:

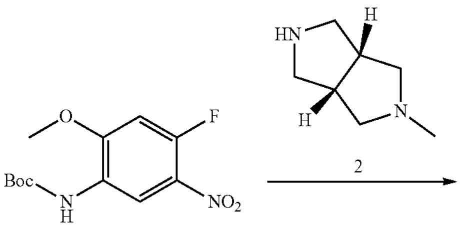

1

2

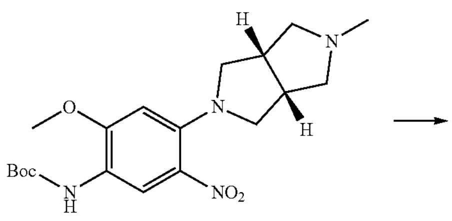

3

-continued

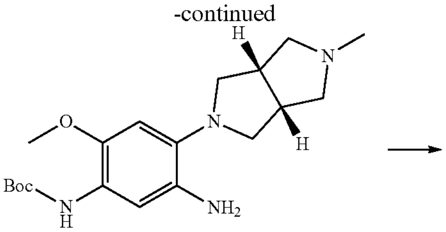

4

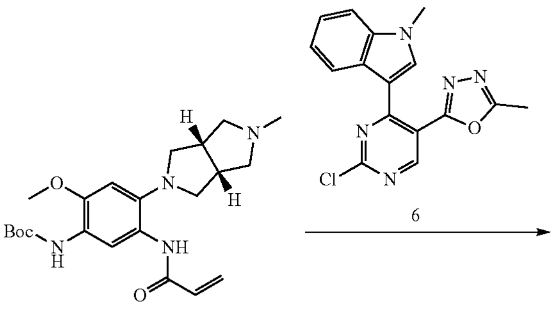

5

6

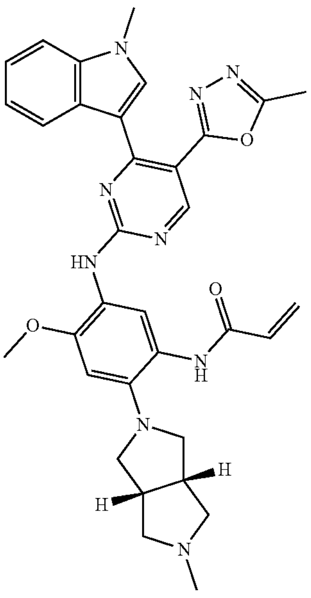

Example 28

Synthesis of Compound 3: Compound 1 (1 g, 3.49 mmol), Compound 2 (0.528 g, 4.19 mmol), and DIPEA (1.35 g, 10.46 mmol) were added to N,N-dimethylacetamide, reacted for 16 h at 80° C. After the raw materials were reacted, water was added, extracted with ethyl acetate three times, the organic phase was combined, washed with brine, dried, concentrated, passed through a chromatographic column to obtain 1.2 g of product.

Synthesis of Compound 4: Compound 3 (1.2 g, 3.06 mmol) and palladium on carbon (240 mg, 20%) were added to methanol, under a hydrogen atmosphere, reacted for 2 h at room temperature. After the raw materials were reacted, diatomite was added for filtration, the filter cake was washed with methanol three times, the filtrate was combined, 1.1 g of crude product was obtained after concentration.

Synthesis of Compound 5: Compound 4 (1.1 g, 3.04 mmol) and triethylamine (0.92 g, 9.11 mmol) were dissolved in dichloromethane, temperature was lowered to 0° C. under nitrogen protection, a dichloromethane solution of acryloyl chloride (0.329 g, 3.95 mmol) was then added dropwise, reacted for 2 h while maintaining at 0° C. After the raw materials were reacted, a saturated aqueous sodium bicarbonate solution was added, extracted with dichloromethane three times, the organic phase was combined, washed with brine, dried, concentrated, passed through a chromatographic column to obtain 0.84 g of product. $^1$HNMR (400 MHz, $CDCl_3$) δ 8.90 (s, 1H), 8.66 (s, 1H), 6.87 (s, 1H), 6.65 (s, 1H), 6.42 (dd, J=16.8, 1.6 Hz, 1H), 6.30 (dd, J=16.8, 10.0 Hz, 1H), 5.69 (dd, J=10.0, 1.6 Hz, 1H), 3.81 (s, 3H), 3.00-2.86 (m, 4H), 2.82 (d, J=9.6 Hz, 2H), 2.66-2.54 (m, 2H), 2.44 (s, 3H), 1.51 (m, 11H).

Synthesis of Example 28: Compound 5 (0.256 g, 0.615 mmol), Compound 6 (0.2 g, 0.615 mmol), and p-toluenesulfonic acid monohydrate (0.14 g, 0.737 mmol) were added to a mixed solvent of ethylene glycol methyl ether and N-methylpyrrolidone, under nitrogen protection, temperature was raised to 120° C., reacted for 16 h, after reacting, water and ethyl acetate were added to the reaction system, the aqueous phase was then extracted three times, the organic phase was combined, spin-dried, 1.28 mg of product was obtained after purification. MS+1: 606.52.

Example 29

The structural formula of the compound used as the kinase inhibitor of the example is:

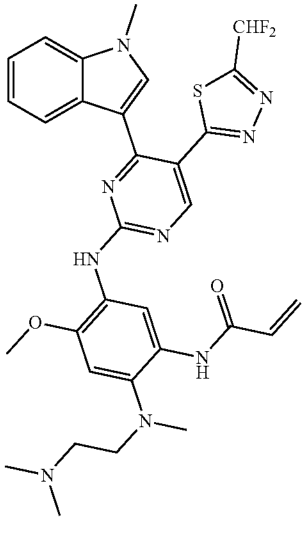 [SMILES: C=CC(=O)Nc1cc(Nc2ncc(-c3nnc(C(F)F)s3)c(-c3cn(C)c4ccccc34)n2)c(OC)cc1N(C)CCN(C)C]

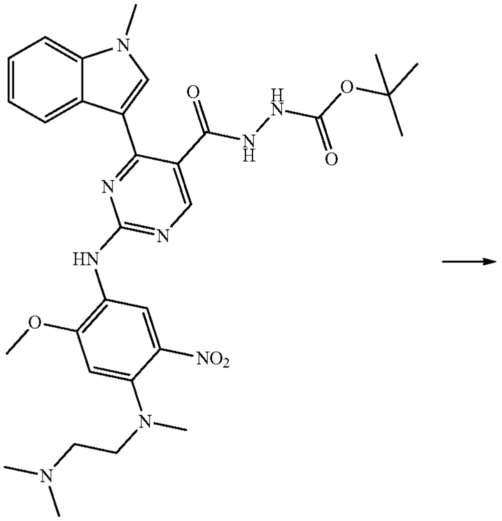

INT 10

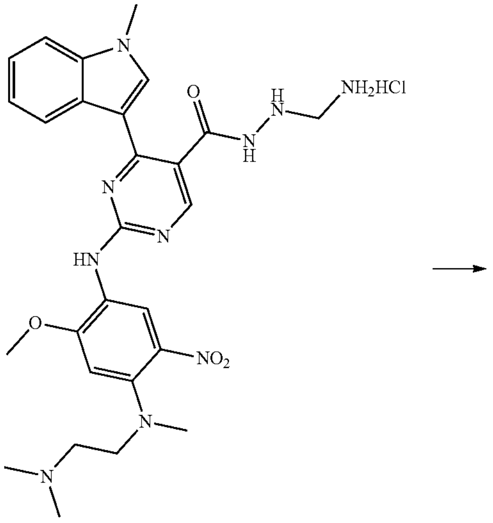

2

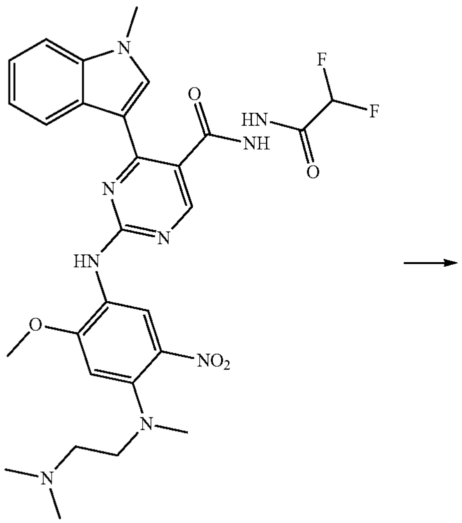

3

-continued

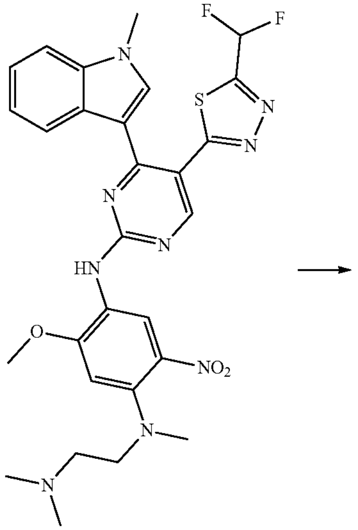

4

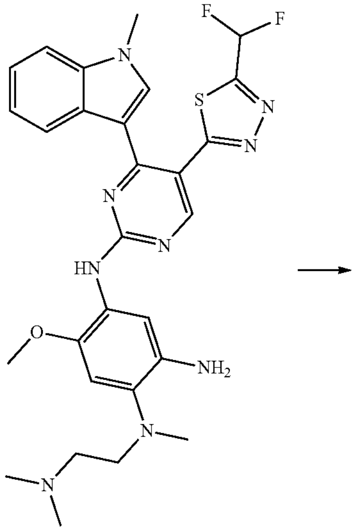

5

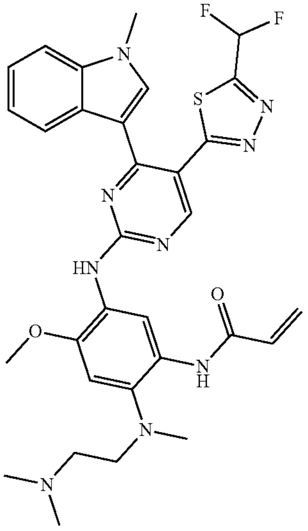

Example 29

Synthesis of Compound 2: in a 100 mL single-necked flask, 30 mL of dioxane hydrochloride was added, under nitrogen protection. INT 10 (0.5 g) was dissolved in 15 mL of dry THF, added dropwise to a reaction flask, 5 mL of THF was then taken and also added dropwise to the reaction flask, stirred for 4 h at 40° C., temperature was lowered to 0° C., filtered with suction, the filter cake was washed with THF, dried under vacuum to obtain 0.44 g of product.

Synthesis of Compound 3: Compound 2 (0.44 g, 0.77 mmol) and triethylamine (0.252 g, 2.5 mmol) were dissolved in dichloromethane, first stirred for 5 minutes, temperature was lowered to 0° C. in an ice bath, difluoroacetic anhydride (0.147 g, 0.85 mmol) was added dropwise, stirred for 30 minutes at low temperature, then stirred overnight at 25° C. The next day, the raw materials disappeared, an aqueous sodium bicarbonate solution was added, extracted with dichloromethane twice, the organic phase was combined, dried, passed through a chromatographic column to obtain 0.3 g of product. $^1$HNMR (400 MHz, DMSO-d6) δ 10.7 (m, 2H) 8.71 (s, 1H), 8.24 (m, 4H), 7.47 (d, J=8.2 Hz, 1H), 7.21 (t, J=7.8 Hz, 1H), 7.01 (s, 1H), 6.84 (s, 1H), 6.50 (t, J=52.9 Hz, 1H), 3.90 (s, 3H), 3.82 (s, 3H), 2.90 (m, 5H), 2.53 (m, 2H), 2.19 (s, 6H).

Synthesis of Compound 4: Compound 3 (0.3 g) was taken, 1.5 g of Lawesson's reagent was added, 70 mL of THF was then added, reflux-reacted for 2 hours at 80° C. The raw materials disappeared, temperature was lowered, processed, passed through a chromatographic column to obtain 0.185 g of pure product.

Synthesis of Compound 5: Compound 4 (185 mg, 0.304 mmol), zinc powder (120 mg, 1.84 mmol), and ammonium chloride (160 mg, 2.99 mmol) were added, temperature was raised to 26° C. after adding, reacted for 2 h. The raw materials disappeared, a saturated aqueous solution of sodium bicarbonate was directly added, extracted with dichloromethane twice, dried, concentrated to obtain 155.4 mg of crude product, directly put into the next step.

Synthesis of Example 29: Compound 5 (416.2 mg) and triethylamine (250 mg) were dissolved in 40 mL of dichloromethane, temperature was lowered to 0° C., acryloyl chloride (90 mg) was then added dropwise, reacted for 3 h while maintaining at 0° C. After the raw materials were reacted, a saturated aqueous sodium bicarbonate solution was added, extracted with dichloromethane twice, dried, concentrated, purified to obtain 66 mg of product. $^1$HNMR (400 MHz, $CDCl_3$) δ 9.79 (s, 1H), 9.51 (s, 1H), 8.99 (s, 1H), 8.71 (m, 1H), 7.97 (s, 1H), 7.31 (d, J=8.2 Hz, 1H), 7.17-7.12 (m, 1H), 7.03 (m, 1H), 6.92 (m, 2H), 6.91 (s, 1H), 6.70 (s, 1H), 6.50 (dd, J=16.9, 2.0 Hz, 1H), 5.74 (d, J=10.2 Hz, 1H), 3.93 (s, 3H), 3.88 (s, 3H), 3.18 (t, J=5.8 Hz, 2H), 2.92 (m, 2H)), 2.68 (s, 3H), 2.65 (m, 6H).

Example 30

The structural formula of the compound used as the kinase inhibitor of the example is:

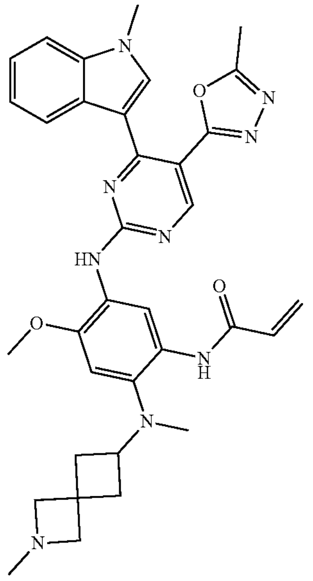 [SMILES: C=CC(=O)Nc1cc(Nc2ncc(-c3nnc(C)o3)c(-c3cn(C)c4ccccc34)n2)c(OC)cc1N(C)C1CC2(C1)CN(C)C2]
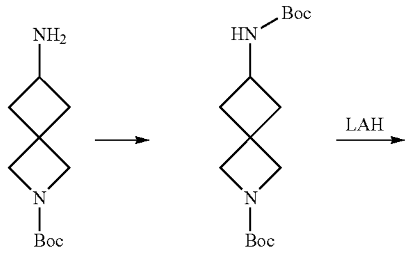
1 2
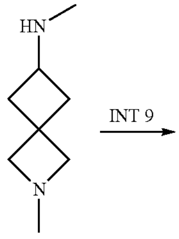
3
-continued
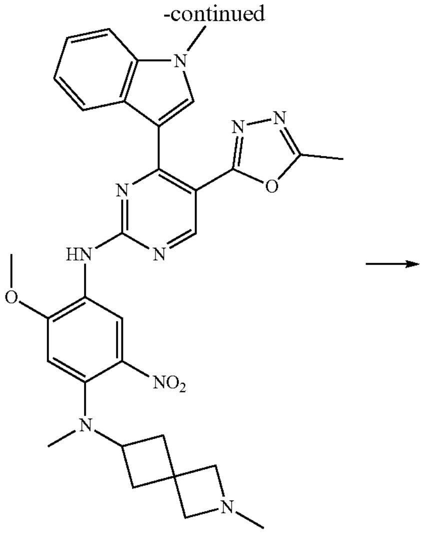
4
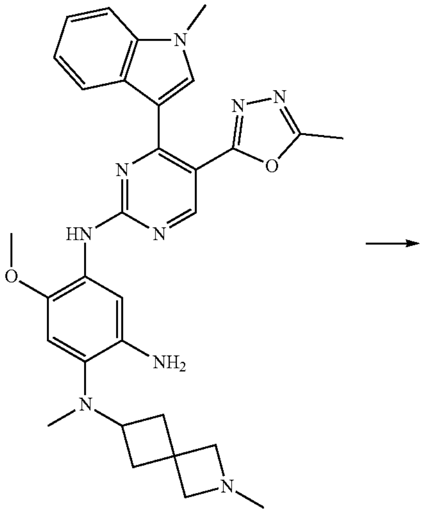
5
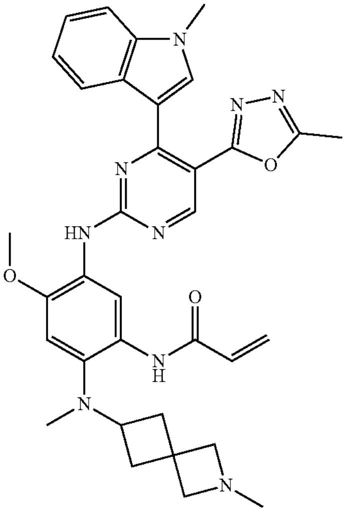
Example 30
Synthesis of Compound 2: Compound 1 (3 g, 14.15 mmol) was dissolved in dichloromethane, temperature was lowered to 0° C. under nitrogen protection, a dichloromethane solution of $Boc_2O$ (3.3 g, 15.14 mmol) was slowly added dropwise while stirring, DMAP (0.34 g, 2.79 mmol) was then added, temperature was slowly raised to room temperature, reaction was continued for 16 h. After the raw materials were reacted, concentrated, passed through a chromatographic column to obtain 3.7 g of product. $^1$HNMR (400 MHz, $CDCl_3$) δ 4.62 (s, 1H), 3.99 (d, J=8.0 Hz, 1H), 3.93 (s, 2H), 3.83 (s, 2H), 2.61-2.51 (m, 2H), 1.99 (ddt, J=11.2, 8.4, 2.4 Hz, 2H), 1.43 (d, J=1.2 Hz, 18H).

Synthesis of Compound 3: lithium tetrahydroaluminum (1.87 g, 49.2 mmol) was added to dry THF, temperature was lowered to 0° C. under nitrogen protection, a tetrahydrofuran solution of Compound 2 (2.56 g, 8.2 mmol) was slowly added dropwise, temperature was then raised to 70° C., reacted for 16 h. After the raw materials were reacted, temperature was lowered to 0° C., 2 mL of water and 2 mL of 20% aqueous sodium hydroxide solution were slowly added dropwise, then filtered to obtain 1.72 g of Compound 3.

Synthesis of Compound 4: INT 9 (200 mg, 0.421 mmol), Compound 3 (88 mg, 0.628 mmol), and DIPEA (162 mg, 1.26 mmol) were added to N,N-dimethylacetamide, reacted for 16 h at 100° C. After the raw materials were reacted, water and ethyl acetate were added, the aqueous phase was extracted with ethyl acetate three times, the organic phase was combined, washed with brine, dried, concentrated, passed through a chromatographic column to obtain 180 mg of Compound 4.

Synthesis of Compound 5: Compound 4 (180 mg, 0.321 mmol) and palladium on carbon (36 mg, 20%) were added to methanol, under a hydrogen atmosphere, reacted for 2 h at room temperature. After the raw materials were reacted, diatomite was added for filtration, the filter cake was washed with methanol three times, the filtrate was combined, 130 mg of Compound 5 was obtained after spin-drying.

Synthesis of Example 30: Compound 5 (130 mg, 0.23 mmol) and triethylamine (70 mg, 0.69 mmol) were dissolved in dichloromethane, temperature was lowered to 0° C. under nitrogen protection, a dichloromethane solution of acryloyl chloride (27 mg, 0.299 mmol) was then added dropwise, reacted for 2 h while maintaining at 0° C. After the raw materials were reacted, a saturated aqueous sodium bicarbonate solution was added, extracted with dichloromethane three times, the organic phase was combined, washed with brine, dried, concentrated, passed through a chromatographic column to obtain 15 mg of product. $^1$HNMR (400 MHz, $CDCl_3$) δ 9.78 (s, 1H), 8.90 (s, 1H), 8.83 (m, 2H), 7.95 (s, 1H), 7.32 (d, J=8.0 Hz, 1H), 7.17 (t, J=7.6 Hz, 1H), 6.97 (m, 2H), 6.80 (s, 1H), 6.45 (dd, J=16.8, 1.7 Hz, 1H), 6.34 (dd, J=16.8, 10.0 Hz, 1H)), 5.79 (dd, J=10.0, 1.6 Hz, 1H), 3.97 (s, 3H), 3.90 (s, 3H), 3.25 (d, J=1.6 Hz, 1H), 3.13 (s, 2H), 2.63 (s, 3H), 2.58 (s, 2H), 2.40 (s, 3H), 2.20 (s, 3H), 1.5 (m, 4H).

Example 31

The structural formula of the compound used as the kinase inhibitor of the example is:

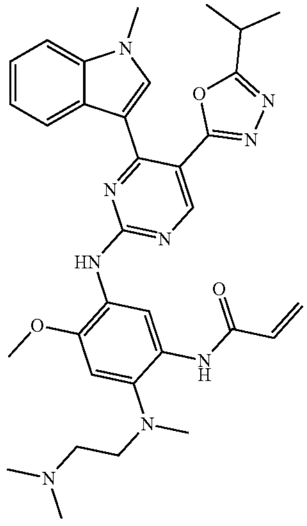 [SMILES: C=CC(=O)Nc1cc(Nc2ncc(-c3nnc(C(C)C)o3)c(-c3cn(C)c4ccccc34)n2)c(OC)cc1N(C)CCN(C)C]

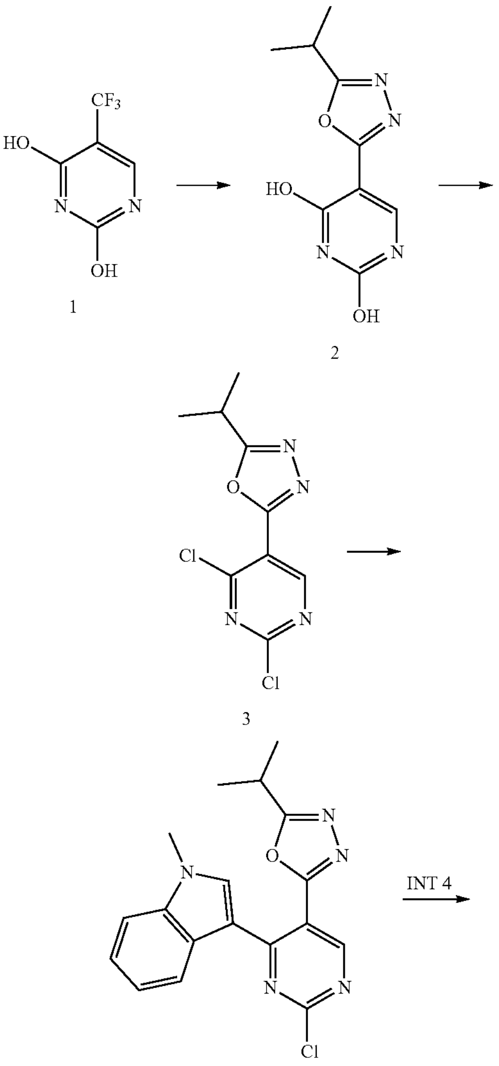

1

2

3

4

-continued

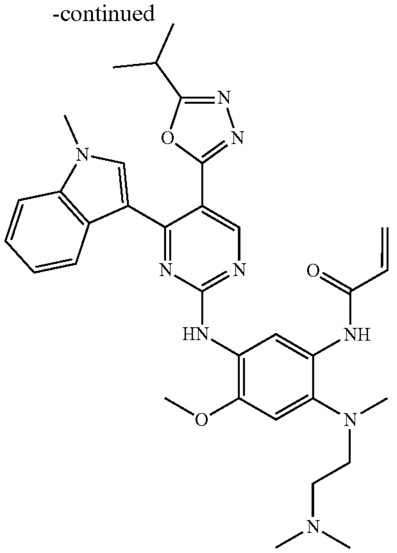

Example 31

Synthesis of Compound 2: in a 250 mL single-necked flask, Compound 1 (5.32 g, 29.56 mmol) and isobutyric acid hydrazide (3.576 g, 35.1 mmol) were added, 90 mL of 1N aqueous sodium hydroxide solution was added, reacted for 5 h at 85° C., temperature was lowered, 8 mL of concentrated hydrochloric acid was added to adjust pH, stirred for 20 minutes in an ice-water bath, filtered with suction, the filter cake was dried under vacuum overnight at 55° C. to obtain 2.05 g of product.

Synthesis of Compound 3: in a 100 mL single-necked flask, Compound 2 (0.94 g, 4.23 mmol), 20 mL of toluene, $POCl_3$ (2.4 ml), DIPEA (2.8 ml) were added, reacted overnight at 80° C. Temperature was lowered, most of the solvent was spun off, the mother liquor was poured into ice water, extracted with ethyl acetate twice, dried, spin-dried, passed through a chromatographic column to obtain 0.395 g of product. $^1$HNMR (400 MHz, $CDCl_3$) δ 9.20 (s, 1H), 3.33 (p, J=7.0 Hz, 1H), 1.48 (d, J=7.0 Hz, 6H).

Synthesis of Compound 4: in a 100 mL single-necked flask, Compound 3 (0.4 g, 1.54 mmol) was dissolved in 40 mL of 1,2-dichloroethane, anhydrous aluminum trichloride (0.35 g, 2.63 mmol) was added, first stirred for 30 minutes at room temperature, temperature was then lowered to 0° C., INT 1 (0.224 g, 1.71 mmol) was added dropwise, stirred for 30 min at low temperature, temperature was then raised to 50° C., reacted for 2 h. Temperature was lowered, poured into ice water, added dichloromethane to extract twice, dried, concentrated, passed through a chromatographic column to obtain 130 mg of product. $^1$HNMR (400 MHz, $CDCl_3$) δ 8.88 (s, 1H), 7.89 (d, J=8.1 Hz, 1H), 7.83 (s, 1H), 7.37 (dt, J=8.2, 1.1 Hz, 1H), 7.30 (ddd, J=8.3, 6.9, 1.2 Hz, 1H), 7.23 (ddd, J=8.1, 7.0, 1.2 Hz, 1H), 3.85 (s, 3H), 3.11 (p, J=7.0 Hz, 1H), 1.20 (d, J=7.0 Hz, 6H).

Synthesis of Example 31: Compound 4 (130 mg, 0.368 mmol), p-toluenesulfonic acid monohydrate (91 mg, 0.478 mmol), and INT 4 (159 mg, 0.406 mmol) were added to 16 mL of ethylene glycol monomethyl ether and 8 mL of NMP, reflux-reacted overnight at 120° C. The next day, an aqueous sodium hydroxide solution was added, extracted with ethyl acetate three times, dried, concentrated, passed through a chromatographic column to obtain 25 mg of product. $^1$HNMR (400 MHz, $CDCl_3$) δ 10.24 (s, 1H), 9.80 (s, 1H), 8.91 (m, 2H), 7.94 (s, 1H), 7.30 (d, J=8.2 Hz, 1H), 7.16-7.08 (m, 1H), 6.94 (m, 2H), 6.80 (s, 1H), 6.48 (dd, J=16.9, 2.0 Hz, 1H), 6.36 (t, J=13.6 Hz, 1H), 5.72 (dd, J=9.8, 2.1 Hz, 1H), 3.96 (s, 3H), 3.89 (s, 3H), 2.87 (q, J=8.7, 7.3 Hz, 3H), 2.71 (s, 3H), 2.26 (s, 8H), 1.25 (s, 6H).

Example 32

The structural formula of the compound used as the kinase inhibitor of the example is:

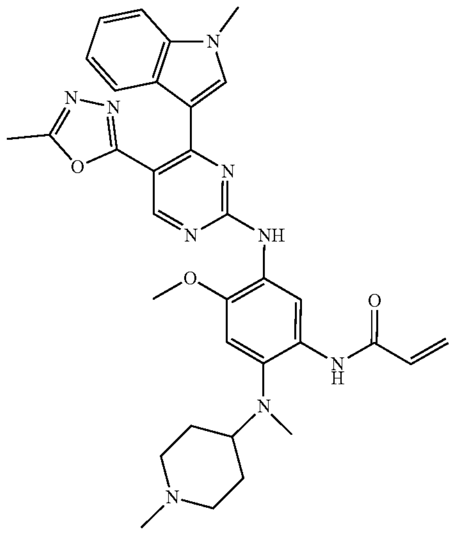 [SMILES: C=CC(=O)Nc1cc(Nc2ncc(-c3nnc(C)o3)c(-c3cn(C)c4ccccc34)n2)c(OC)cc1N(C)C1CCN(C)CC1]

Synthetic Route:

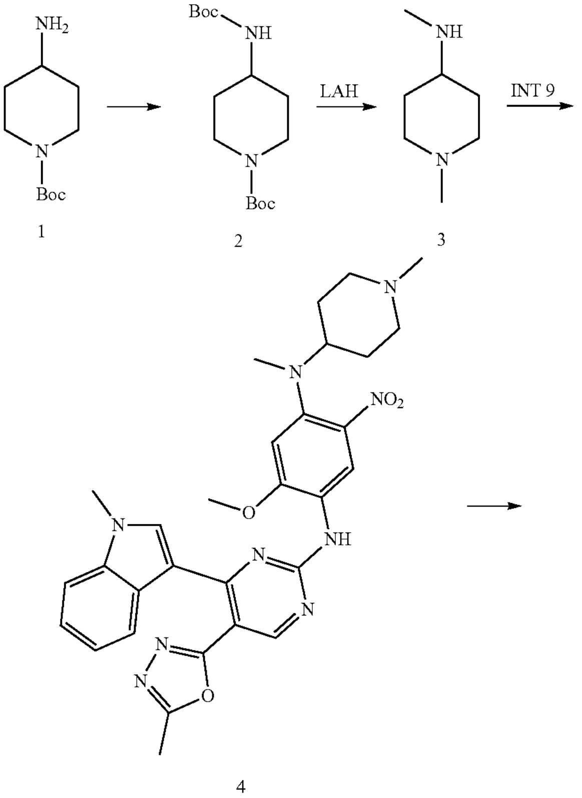

-continued

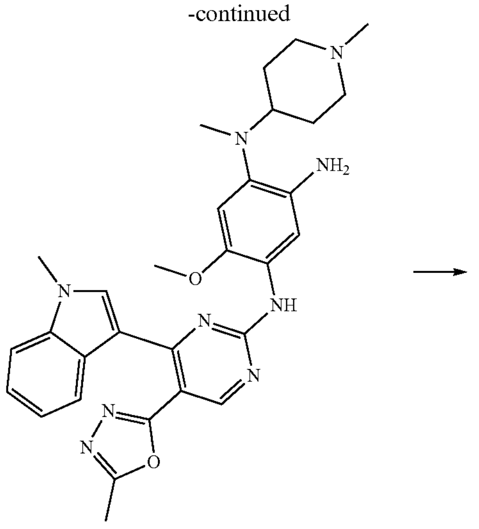

5

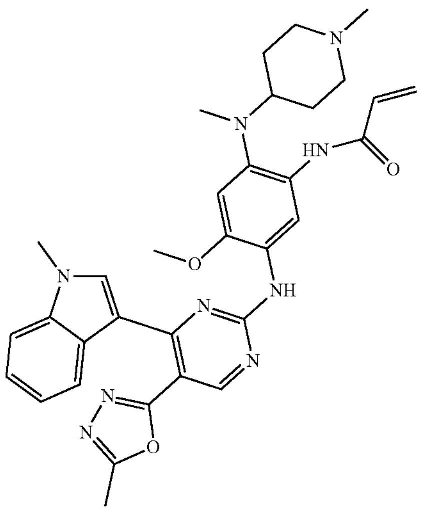

Example 32

Synthesis of Compound 2: Compound 1 (3 g, 15.0 mmol) was dissolved in dichloromethane, temperature was lowered to 0° C. under nitrogen protection, a dichloromethane solution of $Boc_2O$ (3.59 g, 16.5 mmol) was then slowly added dropwise while stirring, DMAP (0.37 g, 3.0 mmol) was then added, and temperature was slowly raised to room temperature, reaction was continued for 16 h. After the raw materials were reacted, concentrated, passed through a chromatographic column to obtain 2.5 g of product.

Synthesis of Compound 3: lithium tetrahydroaluminum (1.89 g, 49.98 mmol) was added to dry tetrahydrofuran, temperature was lowered to 0° C. under nitrogen protection, a tetrahydrofuran solution of Compound 2 (2.5 g, 8.33 mmol) was then slowly added dropwise while stirring, temperature was then raised to 70° C., reacted for 16 h under such condition. After the raw materials were reacted, temperature was lowered to 0° C., and 2 mL of water and 2 mL of 20% aqueous sodium hydroxide solution were slowly added dropwise, then filtered to obtain 2.1 g of product.

Synthesis of Compound 4: INT 9 (300 mg, 0.631 mmol), Compound 3 (122 mg, 0.947 mmol), and DIPEA (245 mg, 1.89 mmol) were added to N,N-dimethylacetamide, reacted for 16 h at 100° C. After the raw materials were reacted, water and ethyl acetate were added to the reaction system, the aqueous phase was extracted with ethyl acetate three times, the organic phase was combined, washed with brine, dried, concentrated, passed through a chromatographic column to obtain 370 mg of product.

Synthesis of Compound 5: Compound 4 (300 mg, 0.514 mmol) and palladium on carbon (60 mg, 20%) were added to methanol, under a hydrogen atmosphere, reacted for 2 h at room temperature. After the raw materials were reacted, diatomite was added for filtration, the filter cake was washed with methanol three times, the filtrate was combined, 310 mg of product was obtained after concentration.

Synthesis of Example 32: Compound 6 (270 mg, 0.488 mmol) and triethylamine (147 mg, 1.46 mmol) were dissolved in dichloromethane, temperature was lowered to 0° C. under nitrogen protection, a dichloromethane solution of acryloyl chloride (58 mg, 0.634 mmol) was then added dropwise, reacted for 2 h while maintaining at 0° C. After the raw materials were reacted, dichloromethane and a saturated aqueous sodium bicarbonate solution were added, the aqueous phase was extracted with dichloromethane three times, the organic phase was combined, washed with brine, dried, the solvent was spin-dried, passed through a chromatographic column to obtain 15 mg of product. $^1$HNMR (400 MHz, $CDCl_3$) δ 9.71 (s, 1H), 8.89 (s, 1H), 8.80 (m, 1H), 8.65 (s, 1H), 7.92 (s, 1H), 7.34-7.30 (m, 1H), 7.16 (t, J=7.6 Hz, 1H), 6.98 (m, 2H), 6.76 (s, 1H), 6.42 (dd, J=16.8, 1.6 Hz, 1H), 6.31 (dd, J=16.8, 10.0 Hz, 1H), 5.78 (dd, J=10.0, 1.6 Hz, 1H), 3.96 (s, 3H), 3.89 (s, 3H), 3.09-2.99 (m, 2H), 2.73 (td, J=11.6, 2.0 Hz, 2H), 2.37 (s, 6H), 2.26-2.17 (m, 4H), 2.07 (s, 2H), 1.66 (dd, J=12.0, 4.0 Hz, 2H).

Example 33

The structural formula of the compound used as the kinase inhibitor of the example is:

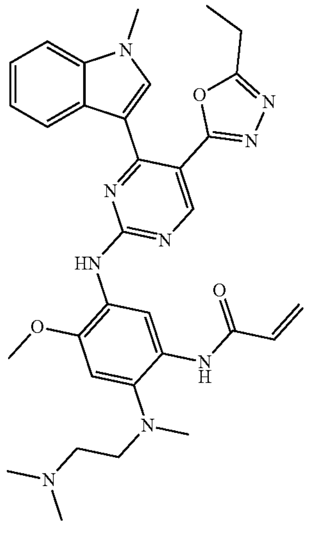 [SMILES: C=CC(=O)Nc1cc(Nc2ncc(-c3nnc(CC)o3)c(-c3cn(C)c4ccccc34)n2)c(OC)cc1N(C)CCN(C)C]

Synthetic Route:

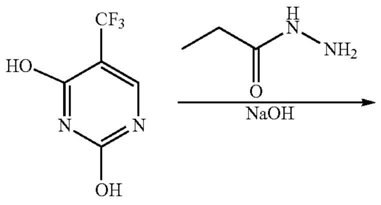

1

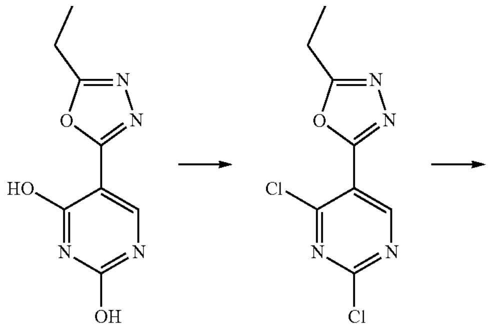

2

3

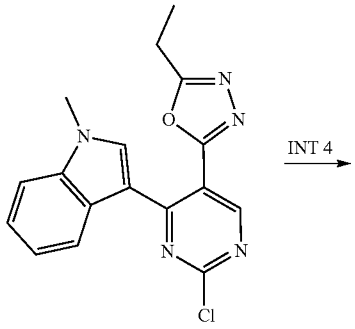

4

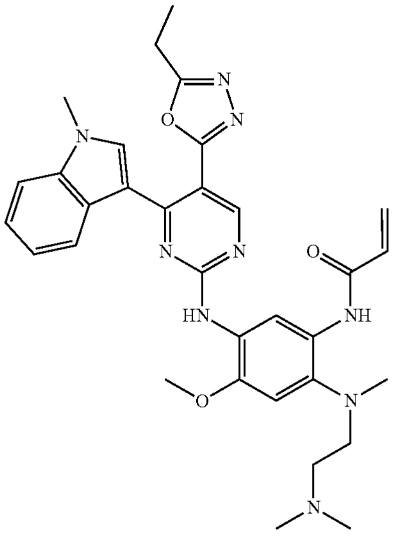

Example 33

Synthesis of Compound 2: in a 250 mL single-necked flask, Compound 1 (18.8 g, 103.2 mmol) and propionic acid hydrazide (10.6 g, 123.8 mmol) were added, 310 mL of 1N aqueous sodium hydroxide solution was added, reacted for 5 h at 85° C., temperature was lowered, 8 ml of concentrated hydrochloric acid was added to adjust pH, stirred for 2 h in an ice-water bath, filtered with suction, the filter cake was dried under vacuum overnight at 55° C. to obtain 6.7 g of product. $^{1}$HNMR (400 MHz, DMSO-d6) δ 11.58 (m, 2H), 8.14 (s, 1H), 2.87 (q, J=7.6 Hz, 2H), 1.27 (t, J=7.5 Hz, 3H).

Synthesis of Compound 3: in a 500 mL single-necked flask, Compound 2 (6.7 g, 32.2 mmol), 160 mL of toluene, $POCl_3$ (18 mL, 0.2 mol), DIPEA (21 mL, 0.13 mol) were sequentially added, reacted overnight at 80° C. Temperature was lowered, most of the solvent was spun off, poured into ice water, ethyl acetate was added to extract twice, dried, concentrated, passed through a chromatographic column to obtain 1.907 g of product. $^{1}$HNMR (400 MHz, $CDCl_3$) δ 9.18 (s, 1H), 3.02 (q, J=7.6 Hz, 2H), 1.46 (t, J=7.6 Hz, 3H).

Synthesis of Compound 4: in a 250 mL single-necked flask, Compound 3 (1.95 g, 8.0 mmol) was dissolved in 180 mL of 1,2-dichloroethane, anhydrous aluminum trichloride (1.81 g, 13.61 mmol) was added, first stirred for 30 minutes at room temperature, temperature was then lowered to 0° C., INT 1 (1.15 g, 8.78 mmol) was added dropwise, stirred for 30 min at low temperature, temperature was then raised to 50° C., reacted for 2 h. Temperature was lowered, poured into ice water, dichloromethane was added to extract twice, dried, concentrated, passed through a chromatographic column to obtain 0.8 g of product. $^{1}$HNMR (400 MHz, $CDCl_3$) δ 8.85 (s, 1H), 7.94 (dt, J=8.0, 1.0 Hz, 1H), 7.90 (s, 1H), 7.42-7.17 (m, 3H), 3.84 (s, 3H), 2.81 (q, J=7.6 Hz, 2H), 1.19 (t, J=7.6 Hz, 3H).

Synthesis of Example 33: Compound 4 (291 mg, 0.86 mmol), p-toluenesulfonic acid monohydrate (213 mg, 1.12 mmol), and INT 4 (376 mg, 0.96 mmol) were added to a mixed solvent of ethylene glycol monomethyl ether and NMP, reflux-reacted overnight at 120° C. The next day, an aqueous sodium hydroxide solution and ethyl acetate were added, extracted three times, dried, concentrated, passed through a chromatographic column to obtain 40 mg of product. $^{1}$HNMR (400 MHz, $CDCl_3$) δ 9.83 (s, 1H), 9.75 (m, 1H), 8.88 (s, 1H), 8.75 (m, 1H), 7.91 (s, 1H), 7.38-7.20 (m, 1H), 7.18-7.06 (m, 1H), 6.95 (t, J=7.3 Hz, 3H), 6.71 (s, 1H), 6.46 (dd, J=16.8, 2.0 Hz, 1H), 5.73 (dd, J=9.9, 2.1 Hz, 1H), 3.92 (s, 3H), 3.87 (s, 3H), 3.05 (m, 2H), 2.69 (m, 5H), 2.50 (m, 8H), 0.81 (d, J=8.0 Hz, 3H).

Example 34

The structural formula of the compound used as the kinase inhibitor of the example is:

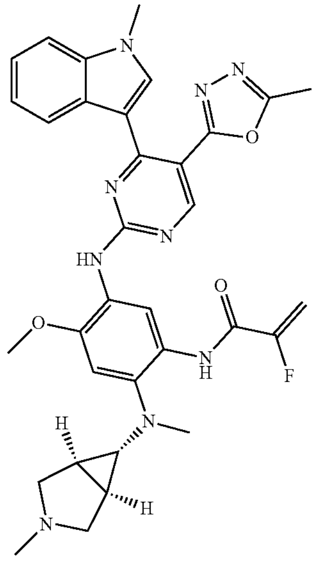

Synthetic Route:

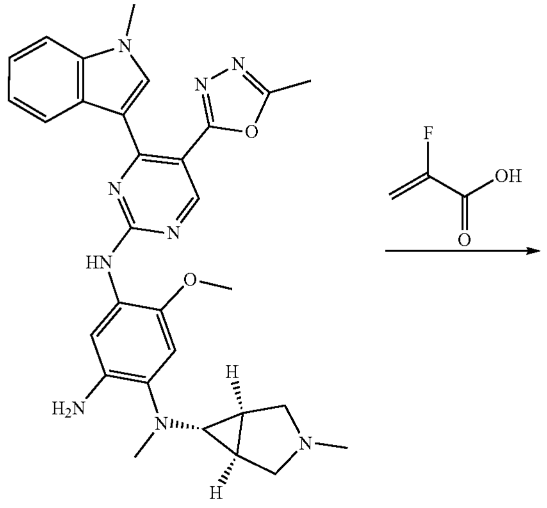

1

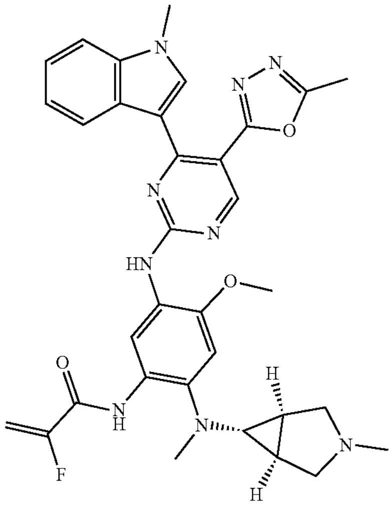

Example 34

Synthesis of Example 34: 2-fluoroacrylic acid (200 mg, 2.22 mmol) was dissolved in dichloromethane, one drop of DMF was added to catalyze, temperature was lowered to 0° C. under nitrogen protection, oxalyl chloride (198 mg, 1.55 mmol) was then slowly added dropwise, after the dropwise addition, temperature was slowly raised to room temperature, reaction was continued for 2 h, monitored by TLC, after the raw materials were reacted, reaction was stopped, set aside. Compound 1 (150 mg, 0.272 mmol) and DIPEA (105 mg, 0.816 mmol) were dissolved in dichloromethane, temperature was lowered to 0° C. under nitrogen protection, a dichloromethane solution of the prepared 2-fluoroacryloyl chloride (39 mg, 0.353 mmol) was then added dropwise, reacted for 2 h while maintaining at 0° C. After the raw materials were reacted, dichloromethane and a saturated aqueous sodium bicarbonate solution were added, extracted with dichloromethane three times, the organic phase was combined, washed with brine, dried, concentrated, passed through a chromatographic column to obtain 20 mg of product. $^1$HNMR (400 MHz, $CDCl_3$) δ 10.67 (s, 1H), 9.55 (s, 1H), 8.89 (s, 1H), 8.72 (m, 1H), 7.98 (s, 1H), δ 7.32 (dt, J=8.3, 0.9 Hz, 1H), 7.17 (t, J=8.0 Hz, 1H), 7.00 (m, 2H), 6.84 (s, 1H), 5.71 (dd, J=46.4, 2.8 Hz, 1H), 5.18 (dd, J=14.8, 2.8 Hz, 1H), 3.97 (s, 3H), 3.91 (s, 3H), 2.83 (m, 2H), 2.67 (s, 3H), 2.63 (t, J=6.4 Hz, 1H), 2.55 (m, 2H), 2.20 (d, J=2.0 Hz, 6H), 1.64 (dd, J=7.2, 2.8 Hz, 2H).

Example 35

The structural formula of the compound used as the kinase inhibitor of the example is:

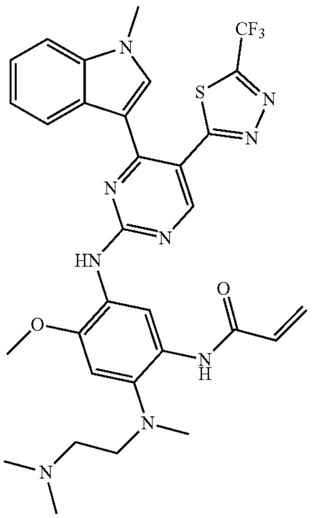 [SMILES: C=CC(=O)Nc1cc(Nc2ncc(-c3nnc(C(F)(F)F)s3)c(-c3cn(C)c4ccccc34)n2)c(OC)cc1N(C)CCN(C)C]

Synthetic Route:
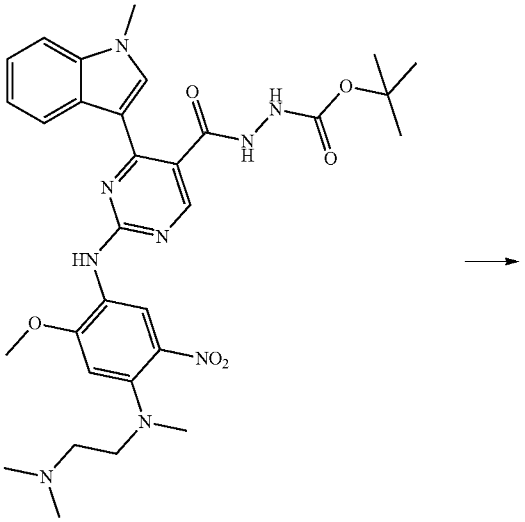
INT 10
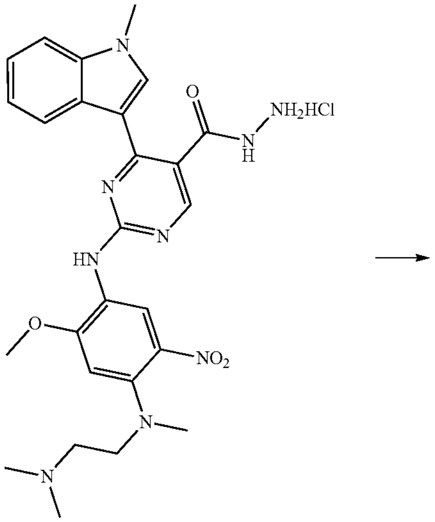
2
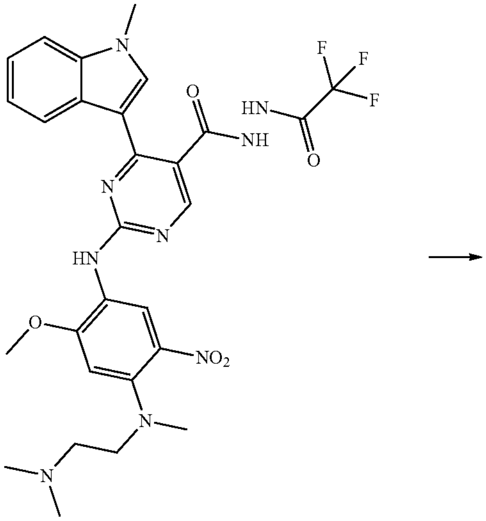
3
-continued
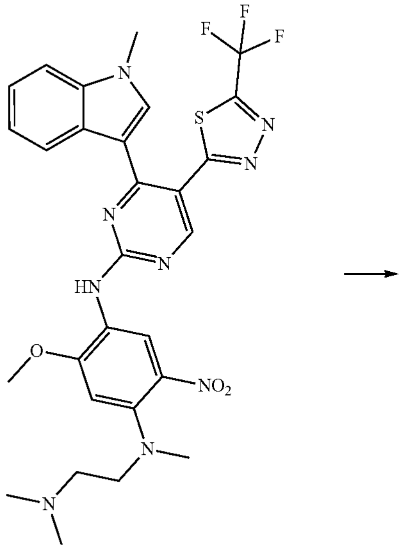
4
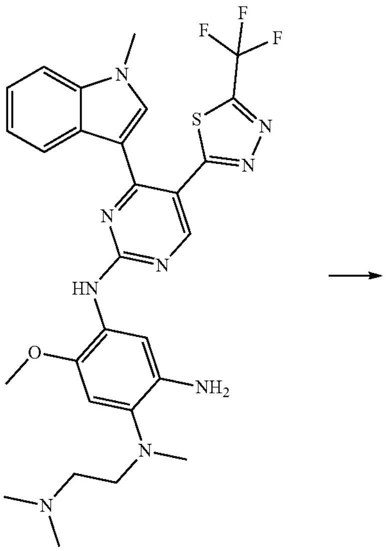
5

-continued

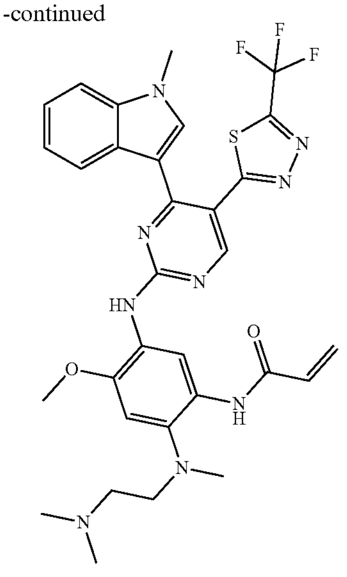

Example 35

Synthesis of Compound 2: in a 100 ml single-necked flask, 40 ml of dioxane hydrochloride was added, under nitrogen protection. INT 10 (0.9 g) was dissolved in 20 mL of dry THF, added dropwise to a reaction flask, 5 mL of THF was then taken and also added dropwise to the reaction flask, stirred for 4 h at 40° C., temperature was then lowered to 0° C., filtered with suction, the filter cake was washed with THF, dried under vacuum to obtain 0.67 g of product.

Synthesis of Compound 3: Compound 2 (0.458 g, 0.81 mmol) and triethylamine (0.243 g, 2.41 mmol) were dissolved in 30 mL of dichloromethane, first stirred for 5 minutes, temperature was lowered to 0° C. in an ice-water bath, trifluoroacetic anhydride (0.204 g, 0.97 mmol) was added dropwise, stirred for 30 minutes at low temperature, then stirred overnight at 25° C. The next day, the raw materials disappeared, a saturated aqueous sodium bicarbonate solution was added, a little methanol was then added, extracted with dichloromethane three times, the organic phase was combined, dried, passed through a chromatographic column to obtain 0.3 g of product.

Synthesis of Compound 4: Compound 3 (0.3 g) was taken, 1.5 g of Lawesson's reagent was added, 70 mL of THF was then added, reflux-reacted for 48 h at 80° C. Temperature was lowered, processed, passed through a chromatographic column to obtain 0.66 g of crude product.

Synthesis of Compound 5: Compound 4 (0.66 g, 1.05 mmol), zinc powder (0.41 g, 6.31 mmol), and ammonium chloride (0.563 g, 10.5 mmol) were added, temperature was raised to 26° C. after adding, reacted for 2 h. The raw materials disappeared, a saturated aqueous solution of sodium bicarbonate, DCM, and a little methanol were directly added, extracted twice, dried, spin-dried to obtain 0.64 g of crude product, directly put into the next step.

Synthesis of Example 35: Compound 5 (0.64 g) and triethylamine (0.33 g, 3.26 mmol) were dissolved in 50 mL of dichloromethane, temperature was lowered to 0° C., acryloyl chloride (0.126 g, 1.4 mmol) was then added dropwise, reacted for 3 h while maintaining at 0° C. After the raw materials were reacted, dichloromethane and a saturated aqueous sodium bicarbonate solution were added, extracted twice, dried, concentrated, passed through a chromatographic column to obtain 7 mg of product. $^1$HNMR (400 MHz, $CDCl_3$) δ 9.80 (m, 2H), 9.04 (s, 1H), 8.76 (m, 1H), 7.96 (s, 1H), 7.32 (d, J=8.2 Hz, 1H), 7.15 (t, J=7.7 Hz, 1H), 6.93 (m, 2H), 6.72 (s, 1H), 6.51 (dd, J=16.7, 2.1 Hz, 1H), 5.77 (d, J=11.5 Hz, 1H), 3.94 (s, 3H), 3.89 (s, 3H), 3.14 (m, 2H), 2.73 (s, 3H), 2.60 (m, 8H).

Example 36

The structural formula of the compound used as the kinase inhibitor of the example is:

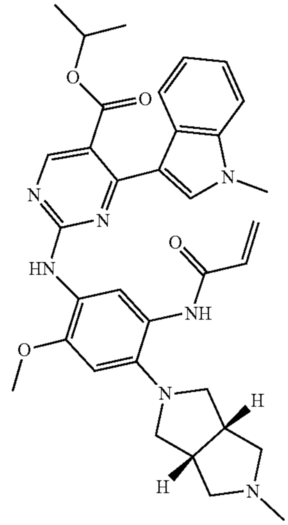

Synthetic Route:

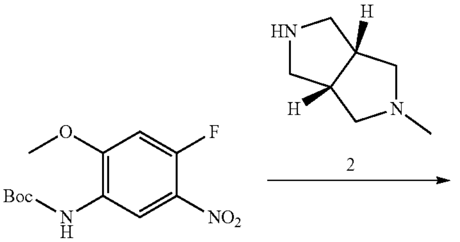

1

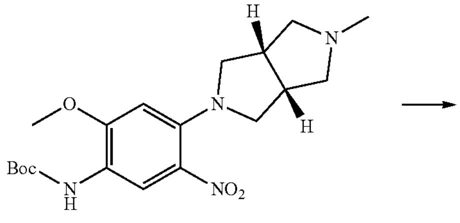

3

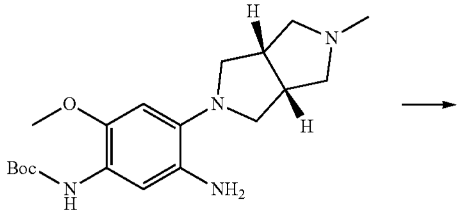

4

-continued

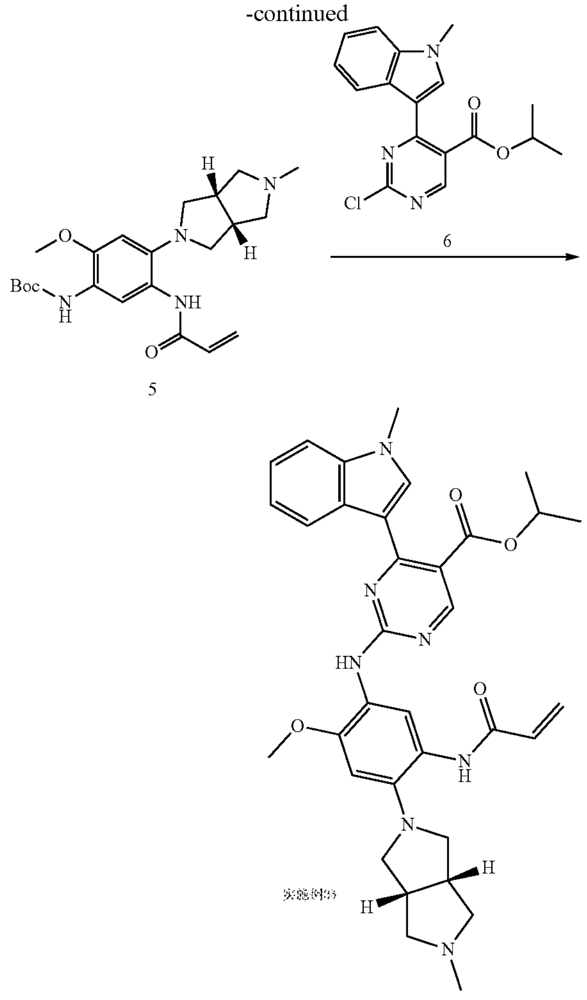

5

6

Synthesis of Compound 3: Compound 1 (1 g, 3.49 mmol), Compound 2 (0.528 g, 4.19 mmol), and DIPEA (1.35 g, 10.46 mmol) were added to N,N-dimethylacetamide, reacted for 16 h at 80° C. After the raw materials were reacted, water was added, extracted with ethyl acetate three times, the organic phase was combined, washed with brine, dried, concentrated, passed through a chromatographic column to obtain 1.2 g of product.

Synthesis of Compound 4: Compound 3 (1.2 g, 3.06 mmol) and palladium on carbon (240 mg, 20%) were added to methanol, under a hydrogen atmosphere, reacted for 2 h at room temperature. After the raw materials were reacted, diatomite was added for filtration, the filter cake was washed with methanol three times, the filtrate was combined, 1.1 g of crude product was obtained after concentration.

Synthesis of Compound 5: Compound 4 (1.1 g, 3.04 mmol) and triethylamine (0.92 g, 9.11 mmol) were dissolved in dichloromethane, temperature was lowered to 0° C. under nitrogen protection, a dichloromethane solution of acryloyl chloride (0.329 g, 3.95 mmol) was then added dropwise, reacted for 2 h while maintaining at 0° C. After the raw materials were reacted, a saturated aqueous sodium bicarbonate solution was added, extracted with dichloromethane three times, the organic phase was combined, washed with brine, dried, concentrated, passed through a chromatographic column to obtain 0.84 g of product. $^1$HNMR (400 MHz, $CDCl_3$) δ 8.90 (s, 1H), 8.66 (s, 1H), 6.87 (s, 1H), 6.65 (s, 1H), 6.42 (dd, J=16.8, 1.6 Hz, 1H), 6.30 (dd, J=16.8, 10.0 Hz, 1H), 5.69 (dd, J=10.0, 1.6 Hz, 1H), 3.81 (s, 3H), 3.00-2.86 (m, 4H), 2.82 (d, J=9.6 Hz, 2H), 2.66-2.54 (m, 2H), 2.44 (s, 3H), 1.51 (m, 11H).

Synthesis of Example 36: Compound 5 (30 mg, 0.072 mmol), Compound 6 (23.7 mg, 0.072 mmol), and p-toluenesulfonic acid monohydrate (20.5 mg, 0.11 mmol) were added to a mixed solvent of ethylene glycol methyl ether and N-methylpyrrolidone, under nitrogen protection, temperature was raised to 120° C., reacted for 6 h, after reacting, water and ethyl acetate were added to the reaction system, the aqueous phase was then extracted three times, the organic phase was combined, spin-dried, 9 mg of product was obtained after purification.

Compounds of Examples 37, 38, and 39 were synthesized with reference to Example 36, see Table 2.

TABLE 2

| Compounds of Examples 37 to 39 | | |
|---|---|---|
| Number | Structure | Characterization |
| Example 37 | 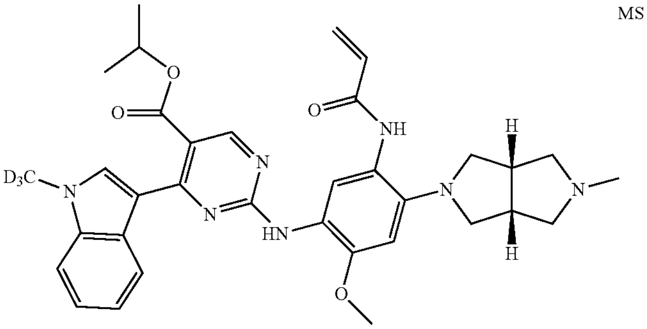 | MS + 1 = 613.4 |

TABLE 2-continued
| Compounds of Examples 37 to 39 | | |
|---|---|---|
| Number | Structure | Characterization |
| Example 38 | 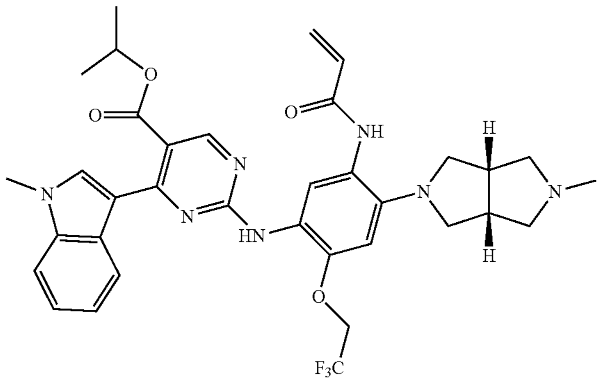 | MS + 1 = 679.5 |
| Example 39 | 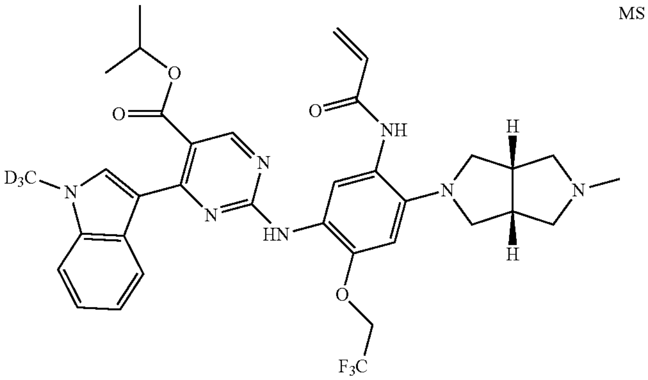 | MS + 1 = 682.5 |
Example 40
The structural formula of the compound used as the kinase inhibitor of the example is:
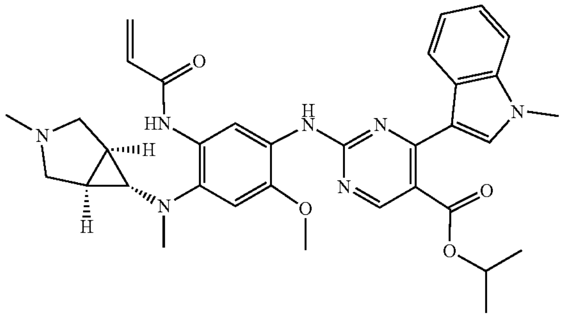
Synthetic Route:
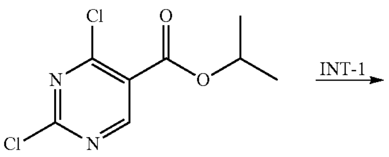
1
-continued
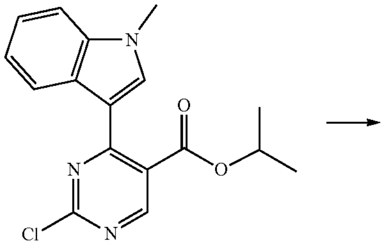
2
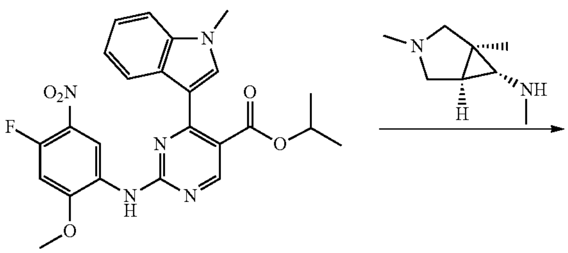
3

-continued

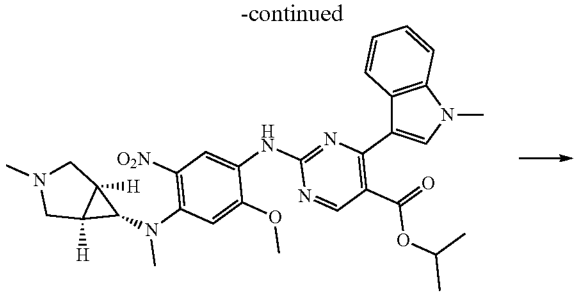

4

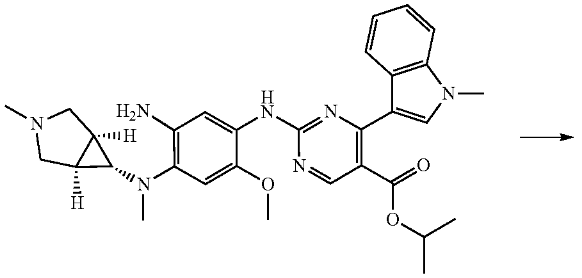

5

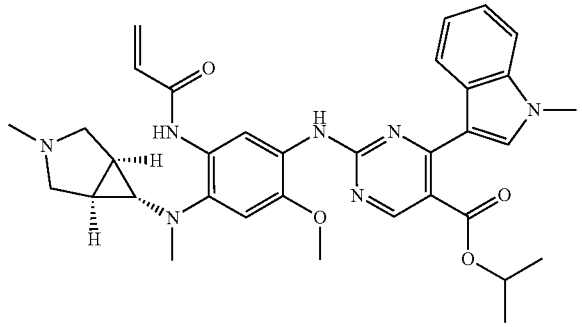

Example 40

Synthesis of Compound 2:

Compound 1 (3 g, 22.9 mmol, 1 eq) and aluminum trichloride (4.56 g, 34.3 mmol, 1.5 eq) were dissolved in dry tetrahydrofuran, temperature was raised to 70° C. under nitrogen protection and reacted for 1 h, a tetrahydrofuran solution (6.45 g, 37.4 mmol, 1.2 eq) of methyl indole was then slowly added dropwise while stirring, reaction was continued for 3 h at 70° C. after adding, monitored by TLC, after the raw materials were reacted, cooled to 0° C., ice water was slowly added to quench, ethyl acetate was added to extract three times, the organic phase was combined, dried with anhydrous Na2SO4, 3.5 g of Compound 2 was obtained after chromatographic column purification (petroleum ether/ethyl acetate=10/1). 1HNMR (400 MHz, Chloroform-d) δ 8.71 (s, 1H), 8.13-8.06 (m, 1H), 7.88 (s, 1H), 7.32-7.28 (m, 1H), 7.24 (m, 2H), 5.12 (m, 1H), 3.80 (s, 3H), 1.18 (d, J=6.0 Hz, 6H).

Synthesis of Compound 3:

Compound 2 (3.5 g, 10.6 mmol, 1 eq) and AZD9291 intermediate (2.96 g, 15.9 mmol, 1.5 eq) were dissolved in dioxane/water, p-toluenesulfonic acid (3.53 g, 18.6 mmol, 1.75 eq) was added while stirring, temperature was then raised to 80° C., reacted for 16 h under such condition, monitored by TLC, after the raw materials were reacted, the reaction system was spin-dried, 2N aqueous sodium hydroxide solution was added to adjust alkali, then extracted with ethyl acetate three times, the organic phase was combined, dried with anhydrous Na2SO4, the solvent was spin-dried, 4.1 g of Compound 3 was obtained after chromatographic column purification (dichloromethane/methanol=20/1). 1HNMR (400 MHz, Chloroform-d) δ 9.59 (d, J=8.4 Hz, 1H), 8.79 (s, 1H), 7.97 (s, 2H), 7.65 (d, J=8.0 Hz, 1H), 7.30 (dt, J=8.4, 1.2 Hz, 1H), 7.24-7.19 (m, 1H), 7.12 (ddd, J=8.0, 7.2, 1.2 Hz, 1H), 6.68 (d, J=12.0 Hz, 1H), 5.02 (m, 1H), 3.93 (s, 3H), 3.85 (s, 3H), 1.07 (d, J=6.0 Hz, 6H).

Synthesis of Compound 4:

Compound 3 (557 mg, 1.19 mmol), amine (Compound 3 in Example 18) (224 mg, 1.78 mmol), and DIPEA (307 mg, 2.38 mmol) were added to N,N-dimethylacetamide, reacted for 16 h at 80° C. The reaction solution was poured into ice water, the solid was precipitated, filtered with suction (filter aid was added), the filter cake was dissolved in dichloromethane, the dichloromethane phase was dried, concentrated, passed through a chromatographic column to obtain 230 mg of product.

Synthesis of Compound 5:

Compound 4 (230 mg, 0.393 mmol) and palladium on carbon (50 mg, 20%) were added to methanol, under a hydrogen atmosphere, reacted for 2 h at room temperature. After the raw materials were reacted, diatomite was added for filtration, the filter cake was washed with methanol three times, the filtrate was combined, 180 mg of Compound 5 was obtained after spin-drying.

Synthesis of Example 40

Compound 5 (180 mg, 0.324 mmol) and triethylamine (104 mg, 1.03 mmol) were dissolved in dichloromethane, temperature was lowered to 0° C. under nitrogen protection, a dichloromethane solution of acryloyl chloride (36 mg, 0.40 mmol) was then added dropwise, reacted for 2 h while maintaining at 0° C. After the raw materials were reacted, a saturated aqueous sodium bicarbonate solution was added, extracted with dichloromethane three times, the organic phase was combined, washed with brine, dried, concentrated, passed through a chromatographic column to obtain 5 mg of product. MS+1: 610.4.

Compounds of Examples 41, 42, 43, 44, 45, 46, and 47 were synthesized with reference to Example 40, see Table 3.

TABLE 3
| Compounds of Examples 41 to 47 | | |
|---|---|---|
| Number | Structure | Characterization |
| Example 41 | 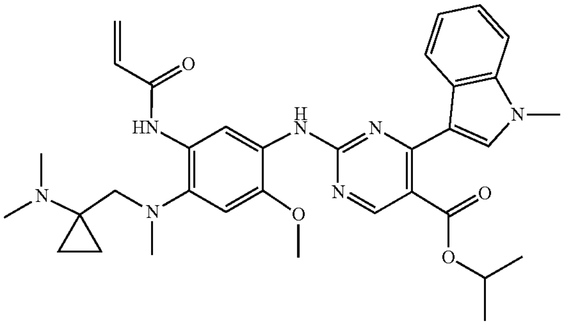 | MS + 1 = 612.3 |
| Example 42 | 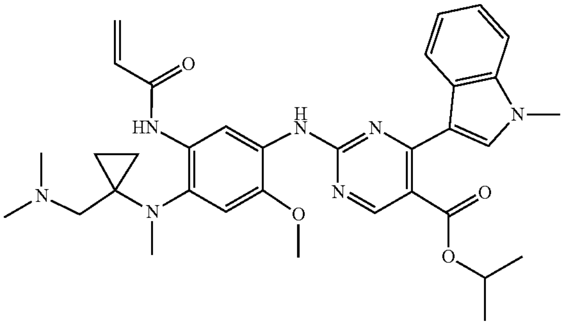 | MS + 1 = 612.2 |
| Example 43 | 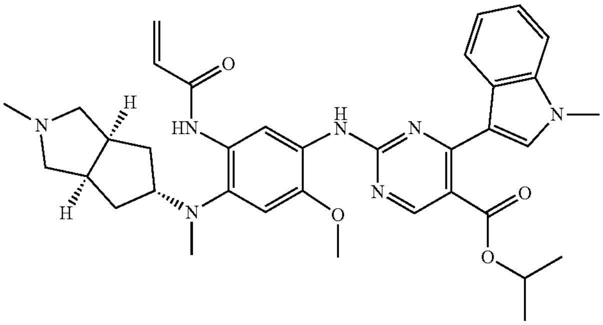 | MS + 1 = 638.3 |
| Example 44 | 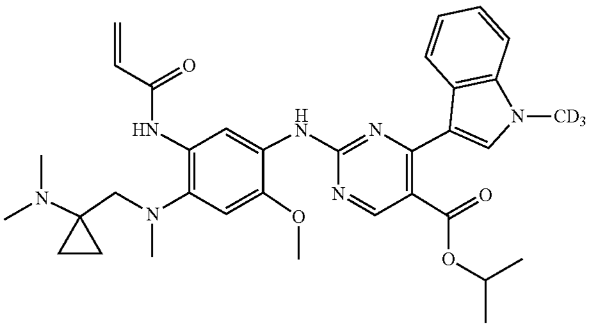 [SMILES: [2H]C([2H])([2H])n1cc(-c2nc(Nc3cc(NC(=O)C=C)c(N(C)CC4(N(C)C)CC4)cc3OC)ncc2C(=O)OC(C)C)c2ccccc21] | MS + 1 = 615.3 |

TABLE 3-continued
| Compounds of Examples 41 to 47 | | |
|---|---|---|
| Number | Structure | Characterization |
| Example 45 | 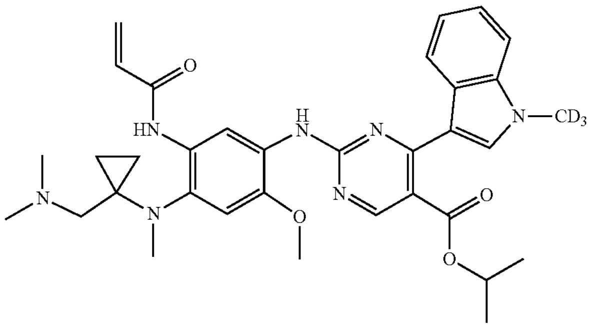 [SMILES: [2H]C([2H])([2H])n1cc(-c2nc(Nc3cc(NC(=O)C=C)c(N(C)C4(CN(C)C)CC4)cc3OC)ncc2C(=O)OC(C)C)c2ccccc21] | MS + 1 = 615.3 |
| Example 46 | 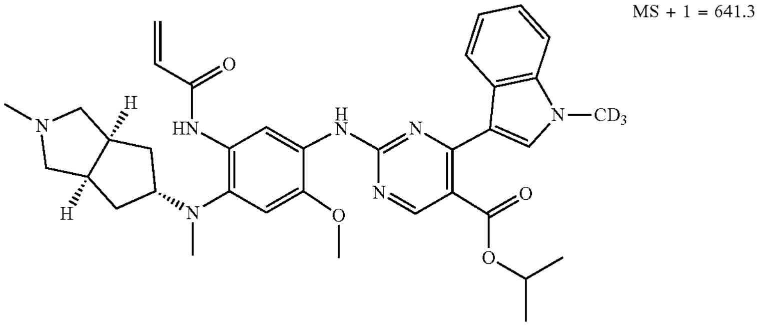 | MS + 1 = 641.3 |
| Example 47 | 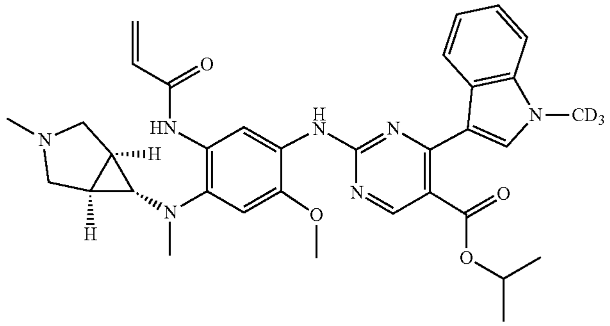 [SMILES: [2H]C([2H])([2H])n1cc(-c2nc(Nc3cc(NC(=O)C=C)c(N(C)[C@H]4[C@@H]5CN(C)C[C@@H]54)cc3OC)ncc2C(=O)OC(C)C)c2ccccc21] | MS + 1 = 613.2 |

II. Biological Experiment Part

1. Kinase Activity Assay

The kinase activity assay was used to screen the activities of the compounds prepared in the examples on EGFR exon 20 insertion mutant kinase at the ATP Km concentration, and Staurosporine and the compound (TAK788) with the optimal activity disclosed in WO2015195228A1 were used as control substances. The biological activity screening of the compounds was repeatedly determined at 10 concentrations.

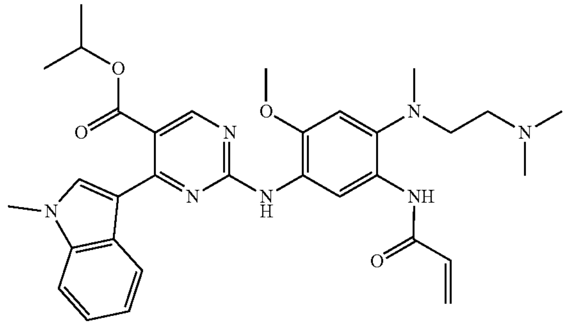

(TAK788)

1. Test Sample

Each sample was prepared respectively as a solution at a concentration of 10 mM.

2. Experimental Method (1) Basic Buffer Solution and Quench Buffer Solution were Prepared for Experimental Kinase 20 mM Hepes (pH 7.5), 10 mM MgCl2, 1 mM EGTA, 0.02% Brij35, 0.02 mg/ml BSA, 0.1 mM Na3VO4, 2 mM DTT, 1% DMSO.

(2) Compound was Prepared for Experimental Kinase

The test compound was dissolved to a specific concentration in 100% dimethyl sulfoxide. DMSO was assisted with Integra Viaflo Assist for (serial) dilution.

(3) Reaction Steps

Kinase was added to a freshly prepared basic reaction buffer solution, any required cofactor was added to the substrate solution.

EGFR exon 20 insertion mutant kinase was added to the substrate solution, gently mixed; compounds in 100% dimethyl sulfoxide were fed into a kinase reaction mixture using acoustic technology (Echo550; nanoliter range), incubated for 20 minutes at room temperature.

33P-ATP (specific activity 10 Ci/l) was added to the reaction mixture, reaction started, incubated for 2 hours at room temperature, radioactivity was detected using filter-binding method.

Kinase activity data were expressed as a percentage of remaining kinase activity in the test sample compared to a medium (dimethyl sulfoxide) reaction. IC50 values and curve fitting were obtained using Prism (GRAPHPAD software).

The obtained inhibitory activity IC50 (nM) values of the test samples on EGFR exon 20 insertion mutant kinase are shown in Table 4.

TABLE 4

Inhibitory activities of different compounds on EGFR exon 20 insertion mutant kinase

| Compound | A763_Y764insFHEA IC50 (nM) | D770-N771insNPG IC50 (nM) |
|---|---|---|
| Staurosporine | 160.4 | 46.9 |
| TAK788 | 4.19 | 0.731 |
| Example 3 | 6.07 | 1.48 |
| Example 4 | 15.3 | 2.79 |
| Example 6 | 9.00 | 1.38 |
| Example 7 | 5600 | 1190 |
| Example 9 | 10.4 | 1.83 |
| Example 10 | 36.4 | 7.66 |
| Example 11 | NA | 7360 |
| Example 12 | 2.27 | 0.30 |
| Example 13 | 61.1 | 169 |
| Example 14 | 44.6 | 10.1 |
| Example 17 | 22.7 | 7.47 |

(NA: No activity.)

As can be seen from Table 4, through the in vitro biological activity screening, with Staurosporine as the control substance, the compounds we used as the kinase inhibitors had good inhibitory ability on EGFR exon 20 insertion mutant kinase, and the inhibitory activities of most of the compounds were much higher than that of Staurosporine. Also, the activities were comparable to that of the compound with the optimal activity disclosed in WO2015195228A1. The activity of the compound of our Example 12 was 2 to 3 times that of the compound with the optimal activity disclosed in WO2015195228A1, which is highly expected to be further developed into a drug for adjusting EGFR exon 20 insertion mutant kinase activity or treating related diseases of EGFR exon 20 insertion mutant kinase.

2. Cell Proliferation Inhibitory Activity Test Experiment of EGFR Exon 20 Insertion Mutation:

1. Experimental Materials:

RPMI-1640, purchased from BI.

Fetal bovine serum, purchased from BI.

CellTiter-Glo®, purchased from Promega.

Dimethyl sulfoxide (DMSO), purchased from TCI.

Cells such as Ba/F3-FL-EGFR-V769-D770 ins ASV, Ba/F3-FL-EGFR-D77-N771 ins SVD, Ba/F3-FL-EGFR-H773-V774 ins NPH, Ba/F3-FL-EGFR-A763-Y764 ins FQEA, constructed by Hefei Precedo Pharmaceuticals Co., Ltd.

2. Experimental Steps:

2.1 Dilution and Administration of Compound

1000× compound mother liquor was prepared using DMSO, diluted to 20× final concentration using a culture medium, set aside.

2.2 Cell Seeding

Cells obtained after centrifugation were suspended with a certain amount of the culture medium and counted. The cell suspension solution was adjusted to a specified density using the culture medium, the diluted cell suspension solution was taken into a 96-well plate; 5 μl of 20× compound solution was added to each well of the 96-well plate, the content of DMSO in the final system was 0.1%; the 96-well plate was incubated for 72 h in a 5% CO2 cell incubator at 37° C.

2.3 Detection

The 96-well plate was brought to room temperature before detection, 50 μl of CellTiter-Glo® reagent was added to each well, the plate was read after being shaken for 2 minutes on a shaker and placed for 10 minutes at room temperature.

3. Data Analysis

Inhibition rate (Inh %) relative to control wells processed by a solvent (DMSO) was calculated using the following equation:

Inhibition rate (Inh %)=100−(RLU compound−RLU blank)/(RLU control−RLU blank)*100%

Data were analyzed using GraphPad 7.0 software, a dose-response curve was obtained by fitting the data, IC50 values were calculated, where A<5 nM, 5 nM≤B≤50 nM, C>50 nM, as shown in Table 5.

TABLE 5

Test results of cell proliferation inhibitory activities of different compounds on EGFR exon 20 insertion mutation

| Compound | Ba/F3-FL-EGFR IC50 (nM) V769-D770ins ASV | D77-N771ins SVD | H773-V774ins NPH | A763-Y764ins FQEA |
|---|---|---|---|---|
| AZD-9291 | B | B | B | B |
| Example 18 | A | A | A | A |
| Example 19 | C | — | — | — |
| Example 20 | C | — | — | — |
| Example 21 | A | — | — | — |
| Example 22 | A | — | — | — |
| Example 23 | A | A | A | A |
| Example 24 | A | A | A | A |
| Example 25 | A | B | B | A |
| Example 26 | A | A | A | A |
| Example 27 | B | — | — | — |
| Example 28 | C | — | — | — |
| Example 29 | B | A | B | A |
| Example 30 | C | — | — | — |
| Example 31 | A | — | — | — |
| Example 32 | B | — | — | — |
| Example 33 | A | A | A | A |
| Example 34 | A | A | B | A |
| Example 36 | A | A | A | A |
| Example 38 | A | — | — | — |
| Example 40 | A | A | A | A |
| Example 41 | A | A | A | A |
| Example 42 | A | — | — | — |
| Example 43 | A | — | — | — |
| Example 47 | A | A | A | A |

It can be seen from Table 5 that the compounds we synthesized had good inhibitory ability on EGFR exon 20 insertion mutation. The activities of most of the compounds were much higher than that of AZD9291. Compared with the activity of TAK-788, most of the compounds of the disclosure had higher activities. For example, the activity of our compound (Example 18) was around 2 times the activity of TAK-788 (see Table 6), which is highly expected to be further developed into a drug for adjusting EGFR exon 20 insertion mutation activity or treating related diseases of EGFR exon 20 insertion mutation.

TABLE 6

Comparison of cell proliferation inhibitory activities of different compounds

| Compound | Ba/F3-FL-EGFR IC50 (nM) V769-D770ins ASV | D77-N771ins SVD | H773-V774ins NPH | A763-Y764ins FQEA |
|---|---|---|---|---|
| TAK-788 | 4.0 | 3.9 | 3.6 | 3.3 |
| AZD-9291 | 24.6 | 41.4 | 38.7 | 13.7 |
| Example 18 | 1.9 | 2.8 | 2.8 | 1.8 |

3. Cell Proliferation Inhibitory Activity Test Experiments of Related EGFR Mutations:

1. Experimental Materials:

RPMI, purchased from Nanjing BioChannel Biotechnology Co., Ltd.

WST-8, purchased from Jinrui Meixiang.

Dimethyl sulfoxide (DMSO), purchased from Aikelab.

Ba/F3 (EGFRdel19/L858R/C797S), purchased from KYinno Biotechnology Co., Ltd.

PC9 (EGFRdel19) and H-1975 (EGFRL858R/T790M) cells, purchased from BeNa Culture Collection.

2. Experimental Steps:

Cell culture medium: RPMI containing 10% fetal bovine serum, 5 mM HEPES, and 2 mM glutamine.

Cell suspension solutions of Ba/F3 (EGFRdel19/L858R/C797S), PC9 (EGFRdel19), and H-1975 (EGFRL858R/T790M) were respectively diluted to 5000 cells/80 microliters, 1500 cells/80 microliters, and 4000 cells/80 microliters, added 80 microliters/well to a 96-well culture plate. Incubated overnight in a 5% carbon dioxide incubator at 37° C.

The compound was diluted to the required concentration in the culture medium at five times the final concentration. 20 microliters of the compound diluent was transferred to a culture plate containing 80 microliters of the cells incubated overnight, and continued to be incubated for 72 hours.

After 72 hours, 10 microliters of 6 mg/ml WST8 solution dissolved in a phosphate buffer solution was added, and incubated for 3 hours in 5% carbon dioxide at 37° C. A light absorption value at 450 nm was read and subtracted by an absorption value at 650 nm.

The obtained light absorption value was used to calculate cell viability according to the following equation:

Cell viability %=(OD determination value/OD drug-free cell)×100

IC50 of the % cell viability corresponding to the compound concentration was calculated with Prizm8.2 software, the results are shown in Table 7.

TABLE 7

| Cell proliferation inhibitory activity experiments of related EGFR mutations | | | |
|---|---|---|---|
| Cell line/$IC_{50}$ (nM) | TAK-788 | AZD-9291 | Example 18 |
| H-1975 (EGFRL858/T790M) | 101.4 | 20.19 | 91.16 |
| PC-9 (EGFRdel19) | 24.05 | 7.846 | 6.612 |
| Ba/F3 (EGFRdel19/L858/797s) | 2627 | 2704 | 3977 |

It can be seen from Table 7 that the cytostatic activity of Example 18 on H-1975 (EGFRL858/T790M) and C-9 (EGFRdel19) is not much different from osimertinib activity, and is even better than TAK788. Therefore, our compound also has a certain treatment effect on the treatment of related diseases caused by EGFR mutation.

The above description is only embodiments of the disclosure, and is not intended to limit the disclosure. Any equivalent transformation made by using the content of the description of the disclosure, or is directly or indirectly used in other relevant technical fields, shall be included in the protection scope of the disclosure as well.

What is claimed is:

1. A compound for inhibiting a kinase, wherein the compound is represented by Formula X' or a pharmaceutically acceptable salt thereof:

Formula X'

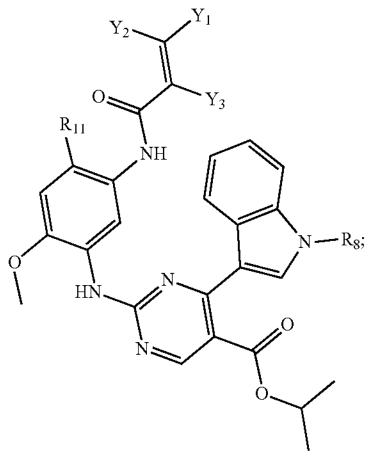

in Formula X', $R_8$ is selected from H, $C_{1-4}$ alkyl, deuterium of $C_{1-4}$ alkyl, or $C_{1-4}$ haloalkyl;

$Y_1$, $Y_2$, and $Y_3$ are each independently selected from H, D, halogen, $C_{1-4}$ haloalkyl, deuterium of $C_{1-4}$ alkyl, $-CH_2NR_{111}R_{112}$, or

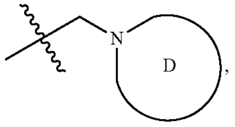, wherein D ring is 4-6 membered cycloalkylamino or 4-6 membered heterocycloalkylamino, the heterocycloalkylamino has 1 to 3 ring carbon atoms in cycloalkylamino that are substituted by heteroatoms selected from O, S, or N;

$R_{11}$ is selected from

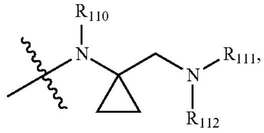

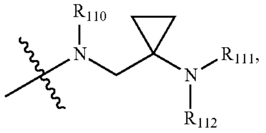

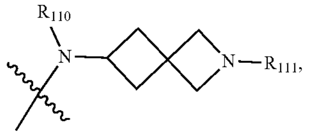

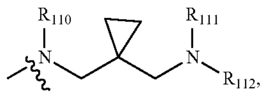

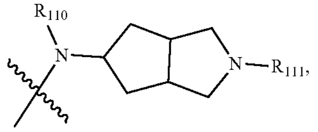

or

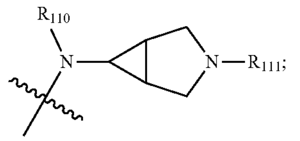

wherein $R_{110}$, $R_{111}$, $R_{112}$ are each independently selected from H, $C_{1-4}$ alkyl, deuterium of $C_{1-4}$ alkyl, or $C_{1-4}$ haloalkyl.

2. The compound for inhibiting the kinase according to claim 1, wherein the compound has following structural formulae:

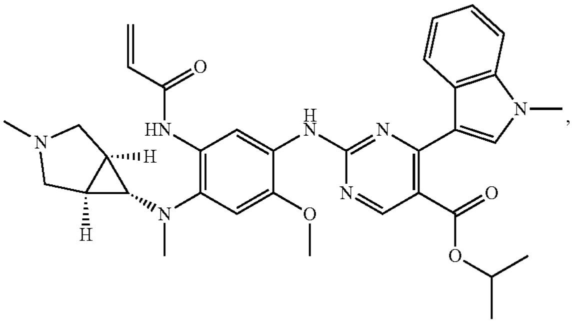

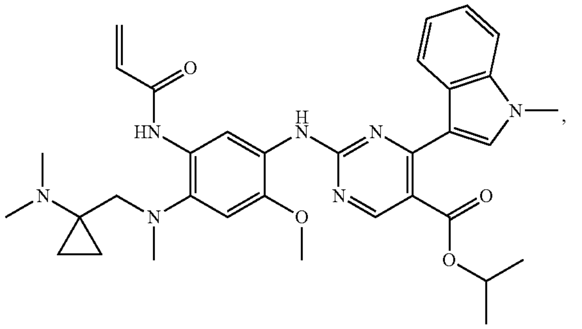

-continued
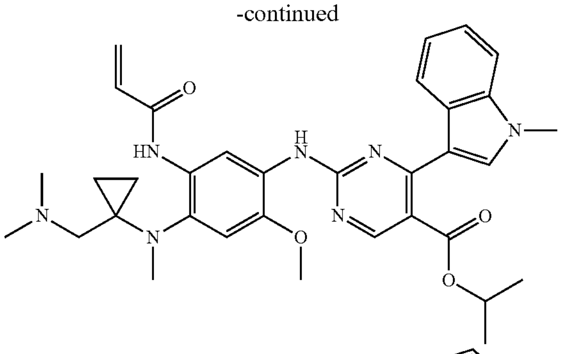
,
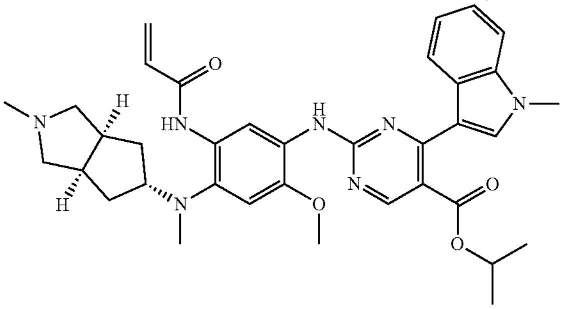
,
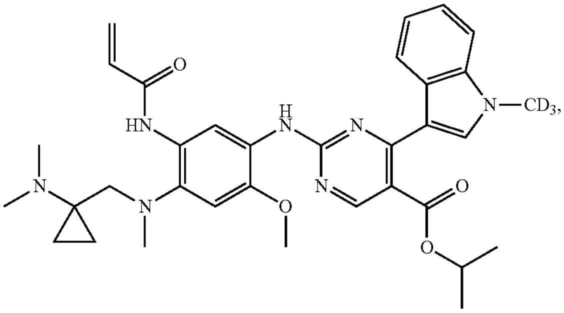
,
-continued
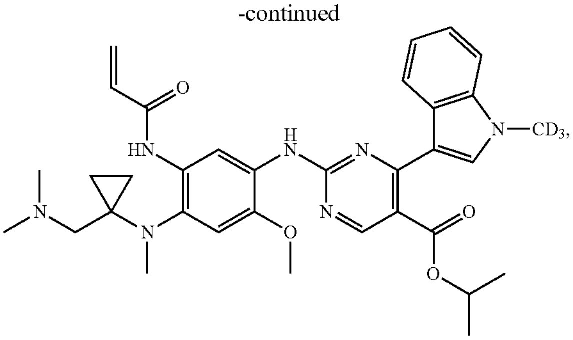
,
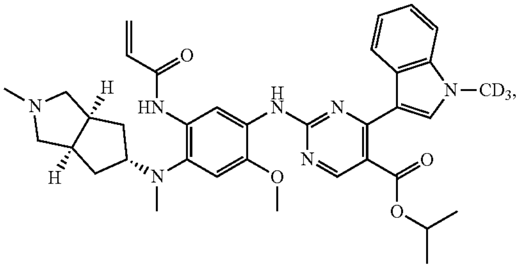
, or
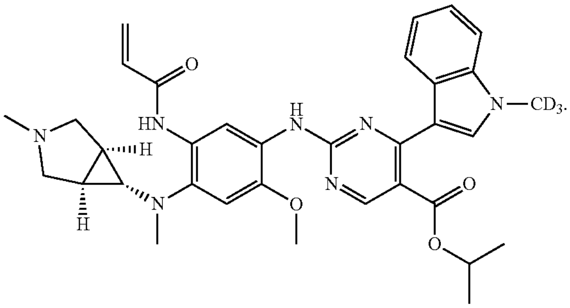
.
* * * * *